US005683999A

United States Patent [19]

Jadhav et al.

[11] Patent Number: 5,683,999

[45] Date of Patent: Nov. 4, 1997

[54] CYCLIC UREA HIV PROTEASE INHIBITORS

[75] Inventors: Prabhakar Kondaji Jadhav, Wilmington; Soo Sung Ko, Hockessin, both of Del.

[73] Assignee: The DuPont Merck Pharmaceutical Company, Wilmington, Del.

[21] Appl. No.: 613,554

[22] Filed: Mar. 11, 1996

Related U.S. Application Data

[63] Continuation-in-part of Ser. No. 406,240, Mar. 17, 1995, abandoned.

[51] Int. Cl.$^6$ .......................... C07D 243/04; A61K 31/55

[52] U.S. Cl. .............................................. 514/218; 540/492

[58] Field of Search ............................... 540/492; 514/218

[56] References Cited

FOREIGN PATENT DOCUMENTS

| | | | |
|---|---|---|---|
| 92 09297 | 6/1992 | WIPO | 514/218 |
| 92 21647 | 12/1992 | WIPO | 514/218 |
| 93 07128 | 4/1993 | WIPO | 514/218 |
| 94 08977 | 4/1994 | WIPO | 514/218 |
| 94 19329 | 9/1994 | WIPO | 514/218 |
| 94 22840 | 10/1994 | WIPO | 514/218 |

OTHER PUBLICATIONS

Lam et al., Science (1994) 263:380–384.

*Primary Examiner*—Robert T. Bond
*Attorney, Agent, or Firm*—Blair Q. Ferguson

[57] ABSTRACT

This invention relates to substituted cyclic ureas and derivatives thereof, including compounds of formula (II):

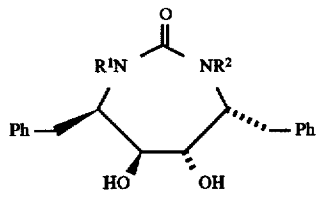

(II)

said compounds being useful as inhibitors of HIV protease. The present invention also relates to pharmaceutical compositions comprising such compounds and to method of using these compounds for the treatment HIV infection. The present invention also relates to the use of such compounds in processes for the identification of HIV protease inhibitors and for the inhibition or detection of HIV in a bodily fluid sample.

18 Claims, No Drawings

CYCLIC UREA HIV PROTEASE INHIBITORS

CROSS REFERENCE TO EARLIER FILED APPLICATION

This application is a continuation-in-part of U.S. patent application Ser. No. 08/406,240, filed Mar. 17, 1995, now abandoned. The disclosure of this earlier filed application is hereby incorporated herein by reference.

FIELD OF THE INVENTION

This invention relates to substituted cyclic ureas and derivatives thereof, including compounds of formula (II):

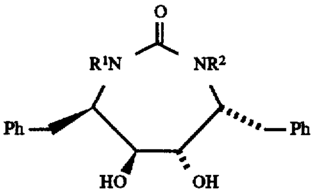

(II)

said compounds being useful as inhibitors of HIV protease. The present invention also relates to pharmaceutical compositions comprising such compounds and to methods of using these compounds for the treatment HIV infection. The present invention also relates to the use of such compounds in processes for the identification of HIV protease inhibitors and for the inhibition or detection of HIV in a bodily fluid sample.

BACKGROUND OF THE INVENTION

The genomes of retroviruses encode a protease that is responsible for the proteolytic processing of one or more polyprotein precursors such as the pol and gag gene products. Retroviral proteases most commonly process the gag precursor into the core proteins, and also process the pol precursor into reverse transcriptase (RT) and retroviral protease.

The correct processing of the precursor polyproteins by the retroviral protease is necessary for the assembly of the infectious virions. Protease-defective virus leads to the production of immature core forms which lack infectivity. Therefore, retroviral protease inhibition provides an attractive target for antiviral therapy.

Human immunodeficiency virus (HIV) type-1 (HIV-1) and type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

AIDS is characterized by a progressive depletion of T lymphocytes, particularly the helper-inducer subset having a CD4 surface antigen ($CD4^+$). $CD4^+$ lymphocytes are responsible for the induction of numerous functions of the human immune system.

No treatment is currently available to completely prevent or reverse the immunodeficiency of AIDS and ARC. In addition, many of the compounds currently used to treat AIDS cause adverse side effects including low platelet count, renal toxicity, and bone marrow cytopenia. Thus, there is a need for improved therapeutic agents for the treatment of HIV infection.

A number of compounds that interfere with viral replication have been developed to treat AIDS, including inhibitors of HIV reverse transcriptase (RT), such as nucleoside analogs including 3'-azido-3'-deoxythymidine (AZT, zidovidine) and 2',3'-dideoxy nucleosides such as 2',3'-dideoxyinosine (DDI, ddI) and 2',3'-dideoxycytidine (DDC, ddC). AZT is known to frequently cause adverse side effects, including causing bone marrow suppression resulting in anemia, leukopenia and thrombocytopenia. Also, AZT-resistant HIV strains have been observed in patients following AZT treatment.

Consequently, there is a continuing need for new effective and safe treatments for HIV infection and the associated HIV disease, including AIDS.

The aspartic acid protease encoded by HIV is critical for replication of the virus. HIV protease is responsible for specific cleavages of the viral gag/pol gene products, which are precursors of essential viral structural proteins and essential enzymes including RT, integrase, and the protease itself (Ratner et al., Nature 316:277–284 (1985); Schneider and Kent, Cell 54: 363–368 (1988); Darke et al., Biochem. Biophys. Res. Commun. 156:297–303 (1988)). Inhibition of HIV protease by inhibitor compounds during infection of cells in cell culture leads to a reduction in the amount of infectious virus particles produced.

PCT patent application WO 92/21647 discloses carbocyclic and heterocyclic HIV protease inhibitors.

PCT patent applications WO 93/07128 published Apr. 15, 1993 and WO 94/19329 published Sep. 1, 1994 disclose cyclic ureas as inhibitors of HIV protease.

The compounds of the invention are of low molecular weight and may, therefore, provide good oral absorption properties in mammals. The compounds of the present invention provide improved antiviral potency, including increased potency against various HIV mutants which are known to be significantly less susceptible to other known inhibitors of HIV protease.

SUMMARY OF THE INVENTION

This invention provides novel substituted cyclic urea compounds and derivatives thereof, of formula (I) (described below) which are useful as inhibitors of human immunodeficiency virus (HIV). The compounds of the present invention inhibit HIV protease and thereby inhibit HIV replication. The present invention also includes pharmaceutical compositions comprising such compounds of formula (I) and methods of using such compounds for the treatment of HIV infection in a patient.

Also included in the present invention are pharmaceutical kits comprising one or more containers containing pharmaceutical dosage units comprising a compound of formula (I), for the treatment of HIV infection.

The present invention also includes methods of inhibiting HIV or treating HIV infection by administering a compound of formula (I) in combination with one or more second therapeutic agents selected from other inhibitors of HIV and/or therapeutic agents for the treatment of HIV-mediated disease conditions.

The present invention includes methods of using such compounds for the detection and inhibition of HIV in a sample, including a bodily fluid sample, which containing HIV.

DETAILED DESCRIPTION OF THE INVENTION

This invention provides novel substituted cyclic urea compounds and derivatives thereof, of formula (I)

(described below) which are useful as inhibitors of human immunodeficiency virus (HIV). The compounds of the present invention inhibit HIV protease and thereby inhibit HIV replication. The present invention also includes pharmaceutical compositions comprising such compounds of formula (I) and methods of using such compounds for the treatment of HIV infection in a patient.

Also included in the present invention are pharmaceutical kits comprising one or more containers containing pharmaceutical dosage units comprising a compound of formula (I), for the treatment of HIV infection.

The present invention also includes methods of inhibiting HIV or treating HIV infection by administering a compound of formula (I) in combination with one or more second therapeutic agents selected from other inhibitors of HIV and/or therapeutic agents for the treatment of HIV-mediated disease conditions.

The present invention includes methods of using such compounds for the detection and inhibition of HIV in a sample, including a bodily fluid sample, which containing HIV.

[1] There is provided by this invention a compound of the formula (I):

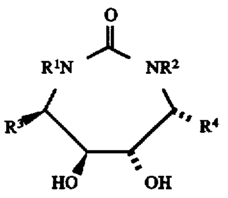

or a pharmaceutically acceptable salt form or prodrug form thereof wherein:

$R^1$ is $—CH_2—X—Y—Z$;

X is selected from:
- $C_1$–$C_4$ alkyl,
- aryl substituted with 0–2 $R^7$,
- $C_3$–$C_6$ cycloalkyl, or
- a heterocycle selected from the group consisting of pyridine, thiophene, furan, thiazole, indazole, thieno[2,3-c]pyrazole and thieno[3,2-c]pyrazole, said heterocycle being substituted with 0–2 $R^7$;

Y is selected from:
- $—(CH_2)_nO—$,
- $—(CH_2)_nS—$,
- $—(CH_2)_nNH—$,
- $—(CH_2)_nC(=O)NH—$,
- $—(CH_2)_nSO_2NH—$
- $—(CH_2)_mNHC(=O)—$,
- $—(CH_2)_nNHCO_2—$,
- $—(CH_2)_mOC(=O)NH—$,
- $—(CH_2)_nNHC(=O)NH—$,
- $—(CH_2)_nC(=NH)NH—$;

n is 0–2;

m is 1–2;

Z is selected from:
- 2-, 3-, or 4-pyridinyl, substituted with 0–1 $R^5$ and 0–1 $R^6$;
- 2-pyrimidinyl, substituted with 0–1 $R^5$ and 0–1 $R^6$;
- 2-pyrazinyl, substituted with 0–1 $R^5$ and 0–1 $R^6$;
- 4-pyrimidon-2-yl or 2-pyrimidon-4-yl, substituted with 0–1 $R^5$ and 0–1 $R^6$;
- 6H-1,3,4-thiadiazin-2-yl, substituted with 0–1 $R^5$ and 0–1 $R^6$;
- 5-uracilyl, substituted with 0–1 $R^5$ and 0–1 $R^6$;
- 2-, 3-, or 4-quinolinyl, substituted with 0–1 $R^5$ and 0–1 $R^6$;
- 1-, 3-, or 4-isoquinolinyl, substituted with 0–1 $R^5$ and 0–1 $R^6$;
- 5- or 6-coumarinyl, substituted with 0–1 $R^5$ and 0–1 $R^6$;
- 3-tetrahydrofuranyl, substituted with 0–1 $R^5$ and 0–1 $R^6$;
- 2- or 3-pyrrolidinyl, substituted with 0–1 $R^5$ and 0–1 $R^6$;
- 2-imidazolidon-4-yl, substituted with 0–1 $R^5$ and 0–1 $R^6$;
- or

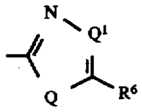
or
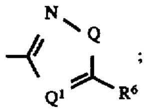
;

Q is O, S or NH;

$Q^1$ is $CR^5$ or N;

$R^2$ is selected from:
- $R^1$;
- $—CH_2—X—Y^1—Z^1$;
- hydrogen;
- ($C_3$–$C_6$ cycloalkyl)methyl substituted with 0–2 $R^7$;
- $C_1$–$C_6$ alkyl substituted with 0–2 $R^7$;
- $C_3$–$C_6$ alkenyl substituted with 0–2 $R^7$;
- $C_3$–$C_6$ alkynyl substituted with 0–2 $R^7$; benzyl substituted with 0–5 $R^9$;
- 2-naphthylmethyl substituted with 0–2 $R^9$;
- 2- or 3-thienylmethyl, 2- or 3-furanylmethyl, or 2-, 3- or 4-pyridinylmethyl, said thienyl, furanyl or pyridinyl being substituted with 0–2 $R^9$; or
- 5- or 6-indazolylmethyl, 5-benzotriazolylmethyl, 5-benzoxazolonylmethyl, 6-benzoxazolonylmethyl, 5-benzimidazolylmethyl, 5-benzoxazolylmethyl, or 5-benzisoxazolylmethyl, said indazolyl, benzimidazolyl, benzoxazolyl and benzisoxazolyl being substituted with 0–1 $R^{10}$;

$Y^1$ is selected from:
- $—(CH_2)_nO(CH_2)_m—$,
- $—(CH_2)_nS(CH_2)_m—$,
- $—(CH_2)_nNH(CH_2)_m—$,
- $—(CH_2)_nC(=O)NH(CH_2)_m—$,
- $—(CH_2)_nSO_2NH(CH_2)_m—$
- $—(CH_2)_mNHC(=O)(CH_2)_m—$,
- $—(CH_2)_nNHCO_2(CH_2)_m—$,
- $—(CH_2)_mOC(=O)NH(CH_2)_m—$,
- $—(CH_2)_nNHC(=O)NH(CH_2)_m—$, or
- $—(CH_2)_nC(=NH)NH(CH_2)_m—$;

$Z^1$ is selected from:
- hydrogen;
- $C_1$–$C_5$ alkyl substituted with 0–2 $R^7$;
- $C_2$–$C_5$ alkenyl substituted with 0–2 $R^7$;
- $C_2$–$C_5$ alkynyl substituted with 0–2 $R^7$;
- $C_3$–$C_6$ cycloalkyl substituted with 0–2 $R^7$;
- aryl substituted with 0–2 $R^9$;
- 2-, 3-, or 4-pyridinyl, substituted with 0–1 $R^5$ and 0–1 $R^6$;
- 2-pyrimidinyl, substituted with 0–1 $R^5$ and 0–1 $R^6$;
- 2-pyrazinyl, substituted with 0–1 $R^5$ and 0–1 $R^6$;
- 4-pyrimidon-2-yl or 2-pyrimidon-4-yl, substituted with 0–1 $R^5$ and 0–1 $R^6$;
- 6H-1,3,4-thiadiazin-2-yl, substituted with 0–1 $R^5$ and 0–1 $R^6$;

5-uracilyl, substituted with 0–1 $R^5$ and 0–1 $R^6$;

2-, 3-, or 4-quinolinyl, substituted with 0–1 $R^5$ and 0–1 $R^6$;

1-, 3-, or 4-isoquinolinyl, substituted with 0–1 $R^5$ and 0–1 $R^6$;

5- or 6-coumarinyl, substituted with 0–1 $R^5$ and 0–1 $R^6$;

3-tetrahydrofuranyl, substituted with 0–1 $R^5$ and 0–1 $R^6$;

2- or 3-pyrrolidinyl, substituted with 0–1 $R^5$ and 0–1 $R^6$;

2-imidazolidon-4-yl, substituted with 0–1 $R^5$ and 0–1 $R^6$;

or

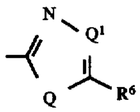
or
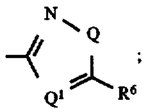
;

$R^3$ and $R^4$ are independently selected from:

benzyl, 4-fluorobenzyl, 2-pyrrolylmethyl, 3-methoxybenzyl, 4-methoxybenzyl, ethyl, isobutyl, cyclohexylmethyl, n-hexyl, 4-nitrobenzyl, 4-aminobenzyl, 3-hydroxybenzyl, 4-hydroxybenzyl, 4-benzyloxybenzyl, 4-thiomethylbenzyl, 2-thienylmethyl, 3-thienylmethyl, 2-thiazolylmethyl, 4-pyridylmethyl 3,4-methylenedioxybenzyl, 3,4-ethylenedioxybenzyl, 1,4-benzoxazin-6-yl-methyl, 4-N,N-dimethylaminobenzyl or 2-naphthylmethyl;

$R^5$ and $R^6$ are independently selected from:

hydrogen, halogen, —CN, —$NO_2$, —OH, —$CO_2R^8$, —$CONHR^8$, —$NR^{11}R^{12}$, —$SR^8$, —$SO_mR^{13}$, $C_1$–$C_4$ haloalkyl, $C_2$–$C_4$ haloalkoxy, $C_1$–$C_4$ alkoxy, $C_1$–$C_6$ alkyl, $C_2$–$C_4$ alkenyl, $C_2$–$C_4$ alkynyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, —CN, —$NO_2$, —$NR^{11}$ $R^{12}$, —$CF_3$, $C_1$–$C_4$ alkyl, $C_1$–$C_4$ alkoxy or —OH, or alternatively, $R^5$ and $R^6$, when substituents on adjacent carbons, can be taken together with the carbon atoms to which they are attached to form a 5–6 membered carbocyclic or heterocyclic ring system, said carbocyclic or heterocyclic ring system being optionally substituted with 1–3 groups independently selected from: Cl, F, Br, —CN, —$NO_2$, —$CF_3$, —$CO_2R^8$, —$COR^8$, —$OCOR^8$, —$NR^{11}R^{12}$, —$CONHR^8$, $C_1$–$C_4$ alkyl, $C_1$–$C_4$ alkoxy or —OH;

$R^7$ is selected from: hydrogen, halogen, —CN, —$NO_2$, —$OR^8$, $C_1$–$C_4$ haloalkyl, $C_2$–$C_4$ haloalkoxy, —$CO_2R^8$, —$COR^8$, —$CONHR^8$, —$NR^{11}$ $R^{12}$, —$OCOR^8$, $C_1$–$C_6$ alkyl, phenyl substituted with 0–2 $R^{10}$, or a 5- or 6-membered heterocycle containing 1 to 4 heteroatoms independently selected from oxygen, nitrogen or sulfur;

$R^8$ is hydrogen, $C_1$–$C_4$ alkyl, phenyl substituted with 0–2 $R^{10}$, or a 5- or 6-membered heterocycle containing 1 to 4 heteroatoms independently selected from oxygen, nitrogen or sulfur;

$R^9$ is selected from: $C_1$–$C_3$ alkyl, $OR^8$, $NR^{11}R^{12}$, hydroxymethyl, CN, F, Cl, Br, $CF_3$, —$CO_2R^8$, —$COR^8$, —$CONHR^{11}$, —CH(NOH), —C(=NOH)$CH_3$, —C(=NOH)$NH_2$, —NHC(=O)$NHR^{11}$, —NHC(O)$OR^{11}$, —$COH(R^8)_2$, methylenedioxy, ethylenedioxy, phenyl substituted with 0–2 $R^{10}$, or a 5- or 6-membered heterocycle containing 1 to 4 heteroatoms independently selected from oxygen, nitrogen or sulfur;

$R^{10}$ is selected from: $C_1$–$C_3$ alkyl, $OR^8$, $NR^{11}R^{12}$, F, Cl, Br, —$COR^8$, —$CO_2R^8$, —$CH_2OR^8$, or —$CH_2C(=O)R^8$;

$R^{11}$ is selected from: hydrogen or $C_1$–$C_4$ alkyl;

$R^{12}$ is selected from: hydrogen, $C_1$–$C_4$ alkyl, glycinyl, alanyl, alanyl-alanyl, phenylglycinyl, phenylalanyl or N-methylglycinyl, N,N-dimethylglycinyl;

$R^{13}$ is selected from: hydrogen, phenyl, benzyl, $C_1$–$C_6$ alkyl or $C_3$–$C_6$ alkoxyalkyl.

[2] The present invention includes compounds of formula (I), of formula (II):

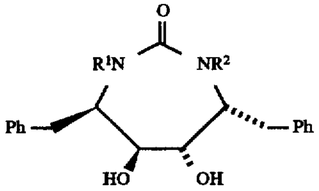
(II)

or a pharmaceutically acceptable salt form thereof, wherein:

$R^1$ is

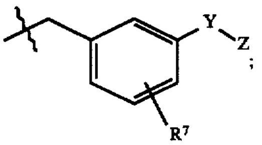
;

Y is selected from:

—$(CH_2)_nO$—,
—$(CH_2)_nS$—,
—$(CH_2)_nNH$—,
—$(CH_2)_nCONH$—,
—$(CH_2)_nSO_2NH$—
—$(CH_2)_nOCONH$—,
—$(CH_2)_nNHCONH$—,
—$(CH_2)_nC(=NH)NH$—;

n is 0–2;

m is 1–2;

Z is a heterocycle selected from:

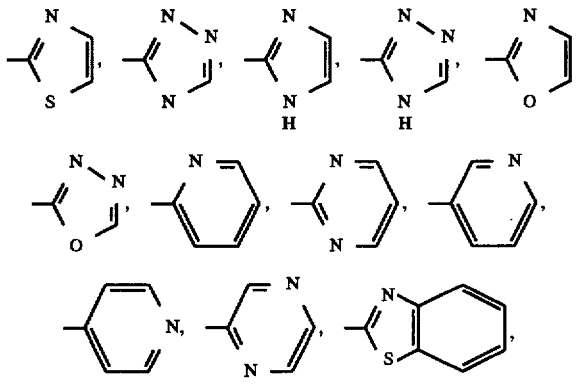

-continued

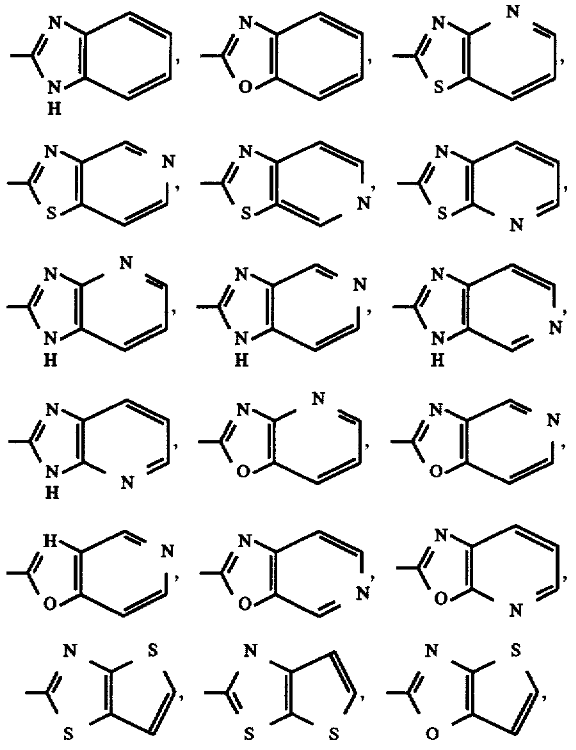

and

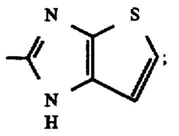

said heterocycle being substituted with 0–1 $R^5$ and 0–1 $R^6$;

$R^2$ is selected from:

$R^1$, $-CH_2-X-Y^1-Z$, cyclopropylmethyl, allyl, 3,3-dimethylallyl, 2-methylallyl, n-propyl, 3-methylbutyl, 2-methylpropyl, n-butyl, n-pentyl, iso-pentyl, 4,4,4-trifluorobutyl, 3-methoxypropyl, benzyl, 2-naphthylmethyl, 3-methoxybenzyl, 4-methoxybenzyl, 3-hydroxybenzyl, 4-hydroxybenzyl, 3-hydroxymethylbenzyl, 4-hydroxymethylbenzyl, 3-(2-hydroxy-isopropyl)benzyl, 3 -(hydroxypropyl)benzyl, 3-(1-hydroxy)ethylbenzyl, 3,5-dimethoxybenzyl, 3-nitrobenzyl, 3-acetylbenzyl, 3-cyanobenzyl, 3-aminobenzyl, 4-aminobenzyl, 3-N-ethylaminobenzyl, 3-N-butylaminobenzyl, 3-N,N-dimethylaminobenzyl, 3-N-propylaminobenzyl, 3-N,N-dipropylaminobenzyl, 3-N-methylaminobenzyl, 4-N-methylaminobenzyl, 4-N-ethylaminobenzyl, 4-N,N-dimethylaminobenzyl, 4-N-butylaminobenzyl, 3-(2-pyridylmethyl)aminobenzyl, 3-(carboethoxymethyl)aminobenzyl, 3-(ethoxycarbonyl)aminobenzyl, 3-amino-4-fluorobenzyl, 4-fluorobenzyl, 4-chlorobenzyl, 3-azido-4-fluoro-benzyl, 3-trifluorobenzyl, 2,4-difluorobenzyl, 3-formaldoximebenzyl, cyclopentylmethyl, 3-carbomethoxybenzyl, 3-carboxybenzyl, 3-N-methylaminocarbonylbenzyl, 3-glycylaminobenzyl, 3-N,N-dimethylaminocarbonylbenzyl, 3-N,N-diethylaminobenzyl, 3-alanylaminobenzyl, 3-(L-alanyl-L-alanyl)aminobenzyl, 3-phenylalanylaminobenzyl, 3-(N-methylglycyl)aminobenzyl, 3-($H_2NC(=NOH)$)benzyl, 3-($CH_3C(=NOH)$)benzyl, 3-(2-pyridyl)benzyl, 5-benzimidazolylmethyl, 5-benzotriazolylmethyl, 5-indazolylmethyl, 6-indazolylmethyl, 2-amino-5-benzoxazolylmethyl, 3-amino-5-benzisoxazolylmethyl, 3-amino-5-indazolylmethyl, 3-methylamino-5-indazolylmethyl, 3-ethylamino-5-indazolylmethyl, 3-methyl-5-indazolylmethyl, 3-methoxy-5-indazolylmethyl, 3-chloro-5-indazolylmethyl, 3,4-methylenedioxybenzyl, 3,4-ethylenedioxybenzyl, 3,4-dihydroxybenzyl, 2-pyridinylmethyl, 2-furanylmethyl, 3-furanylmethyl, 5-bromo-3-furanylmethyl, 1-phenyl-4-pyrazoylmethyl, 3-(1-pyrazolyl)benzyl, 2-thienylmethyl, 3-pyridinylmethyl, 2-pyridinylethyl, 3-pyridinylethyl, 4-pyridinylethyl, 6-hydroxymethyl-3-pyridyl-methyl, 6-chloro-3-pyridyl-methyl, 5-benzoxazolylmethyl, 5-thizolylmethyl, 5-thiazolylethyl 2-methyl-4-thiazolylmethyl or 3-thienylmethyl;

$Y^1$ is selected from:

$-(CH_2)_nO(CH_2)_m-$,
$-(CH_2)_nS(CH_2)_m-$,
$-(CH_2)_nNH(CH_2)_m-$,
$-(CH_2)_nCONH(CH_2)_m-$,
$-(CH_2)_nSO_2{}^{NH}(CH_2)_m-$,
$-(CH_2)_nOCONH(CH_2)_m-$,
$-(CH_2)_nNHCONH(CH_2)_m-$,
$-(CH_2)_nC(=NH)NH(CH_2)_m-$;

$R^5$ and $R^6$ are independently selected from:

hydrogen, halogen, $NO_2$, CN, $CF_3$, $C_1$–$C_4$ alkoxy, $C_1$–$C_6$ alkyl, or phenyl, said phenyl being optionally substituted with 1–3 groups selected independently from: Cl, F, Br, CN, $NO_2$, $CF_3$, $OCH_3$ or OH;

$R^7$ is selected from: hydrogen, halogen, —CN, $-NO_2$, —OH, $CF_3$, $OCH_3$, $CO_2H$, $CO_2R^8$, $COR^8$ or $C_1$–$C_6$ alkyl; $R^8$ is H or $C_1$–$C_4$ alkyl.

[3] Preferred compounds of the present invention include compounds of formula (II), or a pharmaceutically acceptable salt or prodrug form thereof, wherein:

$R^1$ is

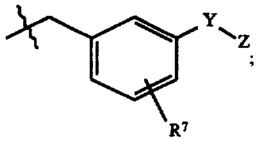

Y is $-(CH_2)_nO-$ or $-(CH_2)_nCONH-$;

n is O;

m is 1–2;

Z is a heterocycle selected from:

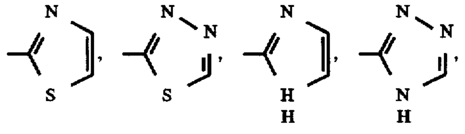

-continued

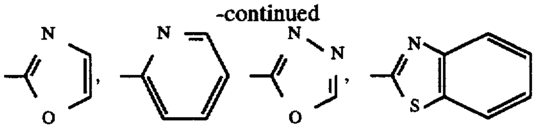

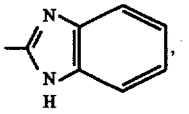

and

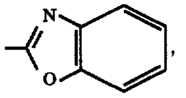

said heterocycle substituted with 0–1 $R^5$ and 0–1 $R^6$;

$R^2$ is selected from:

$R^1$, $—CH_2—X—Y^1—Z$, cyclopropylmethyl, 3,3-dimethylallyl, 2-methylallyl, 3-methylbutyl, 2-methylpropyl, n-butyl, n-pentyl, iso-pentyl, 4,4,4-trifluorobutyl, 3-methoxypropyl, benzyl, 2-naphthylmethyl, 3-methoxybenzyl, 4-methoxybenzyl, 3-hydroxybenzyl, 4-hydroxybenzyl, 3-hydroxymethylbenzyl, 4-hydroxymethylbenzyl, 3-(2-hydroxy-isopropyl) benzyl, 3-(hydroxypropyl)benzyl, 3-(1-hydroxy) ethylbenzyl, 3-acetylbenzyl, 3-cyanobenzyl, 3-aminobenzyl, 4-aminobenzyl, 3-N-ethylaminobenzyl, 3-N-butylaminobenzyl, 3-N,N-dimethylaminobenzyl, 3-N -propylaminobenzyl, 3-N,N -dipropylaminobenzyl, 3-N -methylaminobenzyl, 4-N-methylaminobenzyl, 4-N-ethylaminobenzyl, 4-N,N-dimethylaminobenzyl, 4-N-butylaminobenzyl, 3-(2-pyridylmethyl) aminobenzyl, 3-(carboethoxymethyl)aminobenzyl, 3-(ethoxycarbonyl)aminobenzyl, 3-amino-4-fluorobenzyl, 4-fluorobenzyl, 4-chlorobenzyl, 3-azido-4-fluoro-benzyl, 3-trifluorobenzyl, 2,4-difluorobenzyl, 3-formaldoximebenzyl, cyclopentylmethyl, 3-carbomethoxybenzyl, 3-carboxybenzyl, 3-N-methylaminocarbonylbenzyl, 3-glycylaminobenzyl, 3-N,N-dimethylaminocarbonylbenzyl, 3-N,N-diethylaminobenzyl, 3-alanylaminobenzyl, 3-(L-alanyl-L-alanyl)aminobenzyl, 3-phenylalanylaminobenzyl, 3-(N-methylglycyl) aminobenzyl, 3-($H_2NC(=NOH)$)benzyl, 3-($CH_3C(=NOH)$)benzyl, 3-(2-pyridyl)benzyl, 5-benzimidazolylmethyl, 5-benzotriazolylmethyl, 5-indazolylmethyl, 6-indazolylmethyl, 2-amino-5-benzoxazolylmethyl, 3-amino-5-benzisoxazolylmethyl, 3-amino-5-indazolylmethyl, 3-methylamino-5-indazolylmethyl, 3-ethylamino-5-indazolylmethyl, 3-methyl-5-indazolylmethyl, 3-methoxy-5-indazolylmethyl, 3-chloro-5-indazolylmethyl, 3,4-methylenedioxybenzyl, 3,4-ethylenedioxybenzyl, 3,4-dihydroxybenzyl, 2-pyridinylmethyl, 2-furanylmethyl, 3-furanylmethyl, 5-bromo-3-furanylmethyl, 1-phenyl-4-pyrazoylmethyl, 3-(1-pyrazolyl)benzyl, 2-thienylmethyl, 3-pyridinylmethyl, 2-pyridinylethyl, 3-pyridinylethyl, 4-pyridinylethyl, 6-hydroxymethyl-3-pyridyl-methyl, 6-chloro-3-pyridyl-methyl, 5-benzoxazolylmethyl, 5-thizolylmethyl, 5-thiazolylethyl 2-methyl-4-thiazolylmethyl or 3-thienylmethyl;

$Y^1$ is selected from:

$—(CH_2)_nO(CH_2)_m—$, $—(CH_2)_nCONH(CH_2)_m—$;

$R^5$ and $R^6$ are independently selected from: halogen, $NO_2$, CN, $CF_3$, $C_1$–$C_6$ alkyl, or phenyl, said phenyl being optionally substituted with 1–3 groups independently selected from: Cl, F, Br, CN, $NO_2$, $CF_3$, $OCH_3$ or OH; and $R^7$ is selected from: hydrogen, halogen, —CN, $—NO_2$, —OH, $CF_3$, $OCH_3$, or $C_1$–$C_6$ alkyl.

[4] Preferred compounds of the present invention include compounds of formula (II), or a pharmaceutically acceptable salt or prodrug form thereof, wherein:

$R^1$ is

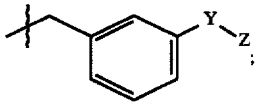

;

Y is —CONH—;

Z is selected from:

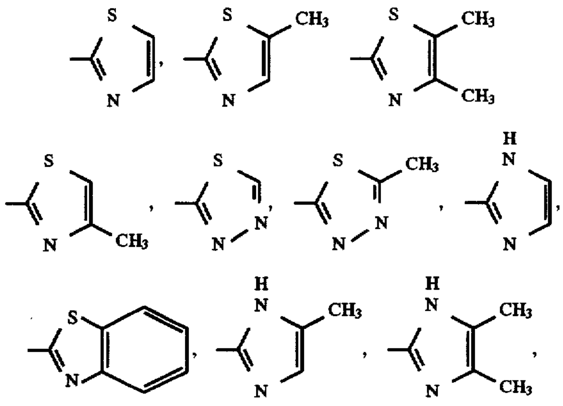

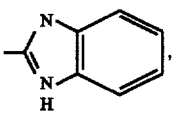

, or

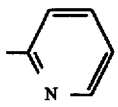

;

$R^2$ is selected from:

$R^1$, cyclopropylmethyl, 3,3-dimethylallyl, 2-methylallyl, 3-methylbutyl, 2-methylpropyl, n-butyl, n-pentyl, iso-pentyl, 3-methoxypropyl, benzyl, 3-(2-hydroxy-isopropyl)benzyl, 3-acetylbenzyl, 3-aminobenzyl, 4-aminobenzyl, 3-N-ethylaminobenzyl, 3-N,N-dimethylaminobenzyl, 3-N-methylaminobenzyl, 4-N-methylaminobenzyl, 3-hydroxymethylbenzyl, 4-hydroxymethylbenzyl, 2-naphthylmethyl, 3-(2-pyridylmethyl)aminobenzyl, 3-amino-4-fluoro-benzyl, 4-fluorobenzyl, 4-chlorobenzyl, 3-trifluorobenzyl, -3-glycylaminobenzyl, 3-alanylaminobenzyl, 3-(L-alanyl-L-alanyl) aminobenzyl, 3-phenylalanylaminobenzyl, 3-(N-methylglycyl)aminobenzyl, 3-(2-pyridyl)benzyl, 5-indazolylmethyl, 3-amino-5-indazolylmethyl, 3-methylamino-5-indazolylmethyl, 3-methyl-5-indazolylmethyl, 3,4-methylenedioxybenzyl, 3,4-ethylenedioxybenzyl, 3-furanylmethyl, 3-(1-pyrazolyl)benzyl, 3-pyridinylmethyl or 3-thienylmethyl.

[5] Preferred compounds of the present invention include compounds of formula (I), or a pharmaceutically acceptable salt or prodrug form thereof, selected from:

the compound of formula (I) wherein $R^3$ and $R^4$ are isobutyl, $R^1$ and $R^2$ are 3-(2-thiazolylaminocarbonyl) phenylmethyl;

the compound of formula (I) wherein $R^3$ and $R^4$ are 4-fluorobenzyl, $R^1$ and $R^2$ are 3-(2-thiazolylaminocarbonyl)phenylmethyl;

the compound of formula (I) wherein $R^3$ and $R^4$ are 3-methoxybenzyl, $R^1$ and $R^2$ are 3-(2-thiazolylaminocarbonyl)phenylmethyl;

the compound of formula (I) wherein $R^3$ and $R^4$ are 3-methoxybenzyl, $R^1$ is cyclopropylmethyl and $R^2$ is (2-thiazolylaminocarbonyl)phenylmethyl;

the compound of formula (I) wherein $R^3$ and $R^4$ are 4-methoxybenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ is benzyl and $R^2$ is (2-thiazolylaminocarbonyl)phenylmethyl;

the compound of formula (I) wherein $R^3$ and $R^4$ are 4-methoxybenzyl, $R^1$ 2-naphthylmethyl and $R^2$ is (2-thiazolylaminocarbonyl)phenylmethyl;

the compound of formula (I) wherein $R^3$ and $R^4$ are 4-hydroxybenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ is benzyl and $R^2$ is (2-thiazolylaminocarbonyl)phenylmethyl;

the compound of formula (I) wherein $R^3$ and $R^4$ are 4-(2-morpholinylethoxy)benzyl, $R^1$ and $R^2$ are 3-(2-thiazolylaminocarbonyl)phenylmethyl;

the compound of formula (I) wherein $R^3$ and $R^4$ are 4-methylthiobenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ and $R^2$ are 3-(2-imidazolylaminocarbonyl)phenylmethyl;

the compound of formula (I) wherein $R^3$ and $R^4$ are 4-methoxybenzyl, $R^1$ and $R^2$ are 3-(2-benzothiazolylaminocarbonyl)phenylmethyl;

the compound of formula (I) wherein $R^3$ and $R^4$ are isobutyl, $R^1$ and $R^2$ are 3-(2-imidazolylaminocarbonyl)phenylmethyl;

the compound of formula (I) wherein $R^3$ and $R^4$ are 4-fluorobenzyl, $R^1$ and $R^2$ are 3-(2-imidazolylaminocarbonyl)phenylmethyl;

the compound of formula (I) wherein $R^3$ and $R^4$ are 3-methoxybenzyl, $R^1$ and $R^2$ are 3-(2-imidazolylaminocarbonyl)phenylmethyl;

the compound of formula (I) wherein $R^3$ and $R^4$ are 3-methoxybenzyl, $R^1$ is cyclopropylmethyl and $R^2$ is (2-imidazolylaminocarbonyl)phenylmethyl;

the compound of formula (I) wherein $R^3$ and $R^4$ are 4-methoxybenzyl, $R^1$ is benzyl and $R^2$ is (2-imidazolylaminocarbonyl)phenylmethyl;

the compound of formula (I) wherein $R^3$ and $R^4$ are 4-methoxybenzyl, $R^1$ 2-naphthylmethyl and $R^2$ is (2-imidazolylaminocarbonyl)phenylmethyl;

the compound of formula (I) wherein $R^3$ and $R^4$ are 4-hydroxybenzyl, $R^1$ and $R^2$ are 3-(2-imidazolylaminocarbonyl)phenylmethyl;

the compound of formula (I) wherein $R^3$ and $R^4$ are 4-(2-morpholinylethoxy)benzyl, $R^1$ and $R^2$ are 3-(2-imidazolylaminocarbonyl)phenylmethyl;

the compound of formula (I) wherein $R^3$ and $R^4$ are 4-methylthiobenzyl, $R^1$ and $R^2$ are 3-(2-imidazolylaminocarbonyl)phenylmethyl.

Preferred compounds of the present invention include compounds, or a pharmaceutically acceptable salt form or prodrug form thereof, selected from:

the compound of formula (II) wherein $R^1$ is 3-(2-thiazolylaminocarbonyl)phenylmethyl and $R^2$ is 3-(2-thiazolylaminocarbonyl)phenylmethyl;

the compound of formula (II) wherein $R^1$ is 3-(4-methyl-2-thiazolylaminocarbonyl)phenylmethyl and $R^2$ is 3-(4-methyl-2-thiazolylaminocarbonyl)phenylmethyl;

the compound of formula (II) wherein $R^1$ is 3-(1,3,4-thiadiazol-2-ylaminocarbonyl)phenylmethyl and $R^2$ is 3-(1,3,4-thiadiazol-2-ylaminocarbonyl)phenylmethyl;

the compound of formula (II) wherein $R^1$ is 3-(5-methyl-1,3,4-thiadiazol-2-ylaminocarbonyl)phenylmethyl and $R^2$ is 3-(5-methyl-1,3,4-thiadiazol-2-ylaminocarbonyl)phenylmethyl;

the compound of formula (II) wherein $R^2$ is 3-(5-t-butyl-1,3,4-thiadiazol-2-ylaminocarbonyl)phenylmethyl and $R^2$ is 3-(5-t-butyl-1,3,4-thiadiazol-2-ylaminocarbonyl)phenylmethyl;

the compound of formula (II) wherein $R^1$ is 3-(5-methyl-2-thiazolylaminocarbonyl)phenylmethyl and $R^2$ is 3-(5-methyl-2-thiazolylaminocarbonyl)phenylmethyl;

the compound of formula (II) wherein $R^1$ is 3-(4,5-dimethyl-2-thiazolylaminocarbonyl)phenylmethyl and $R^2$ is 3-(4,5-dimethyl-2-thiazolylaminocarbonyl)phenylmethyl;

the compound of formula (II) wherein $R^1$ is 3-(2-imidazolylaminocarbonyl)phenylmethyl and $R^2$ is 3-(2-imidazolylaminocarbonyl)phenylmethyl;

the compound of formula (II) wherein $R^1$ is 3-(2-pyridylaminocarbonyl)phenylmethyl and $R^2$ is 3-(2-pyridylaminocarbonyl)phenylmethyl;

the compound of formula (II) wherein $R^1$ is 3-(2-benzothiazolylaminocarbonyl)phenylmethyl and $R^2$ is 3-(2-benzothiazolylaminocarbonyl)phenylmethyl;

the compound of formula (II) wherein $R^1$ is 3-(2-benzimidazolylaminocarbonyl)phenylmethyl and $R^2$ is 3-(2-benzimidazolylaminocarbonyl)phenylmethyl;

the compound of formula (II) wherein $R^1$ is 3-(2-thiazolyloxy)phenylmethyl and $R^2$ is 3-(2-thiazolyloxy)phenylmethyl;

the compound of formula (II) wherein $R^1$ is 3-(2-pyridinyloxy)phenylmethyl and $R^2$ is 3-(2-pyridinyloxy)phenylmethyl;

the compound of formula (II) wherein $R^1$ is 3-[(3-methyl-2-pyridinyl)aminocarbonyl]phenylmethyl and $R^2$ is 3-[(3-methyl-2-pyridinyl)aminocarbonyl]phenylmethyl;

the compound of formula (II) wherein $R^1$ is 3-[(4-methyl-2-pyridinyl)aminocarbonyl]phenylmethyl and $R^2$ is 3-[(4-methyl-2-pyridinyl)aminocarbonyl]phenylmethyl;

the compound of formula (II) wherein $R^1$ is 3-[(5-methyl-2-pyridinyl)aminocarbonyl]phenylmethyl and $R^2$ is 3-[(5-methyl-2-pyridinyl)aminocarbonyl]phenylmethyl;

the compound of formula (II) wherein $R^1$ is 3-[(6-methyl-2-pyridinyl)aminocarbonyl]phenylmethyl and $R^2$ is 3-[(6-methyl-2-pyridinyl)aminocarbonyl]phenylmethyl;

the compound of formula (II) wherein $R^1$ is cyclopropylmethyl and $R^2$ is 3-(2-thiazolylaminocarbonyl)phenylmethyl;

the compound of formula (II) wherein $R^1$ is n-butyl and $R^2$ is 3-(2-thiazolylaminocarbonyl)phenylmethyl;

the compound of formula (II) wherein $R^1$ is benzyl and $R^2$ is 3-(2-thiazolylaminocarbonyl)phenylmethyl;

the compound of formula (II) wherein $R^1$ is 2-naphthylmethyl and $R^2$ is 3-(2-thiazolylaminocarbonyl)phenylmethyl;

the compound of formula (II) wherein $R^1$ is (3-n-butylaminobenzyl and $R^2$ is 3-(2-thiazolylaminocarbonyl)phenylmethyl;

the compound of formula (II) wherein $R^1$ is 3-aminobenzyl and $R^2$ is 3-(2-thiazolylaminocarbonyl)phenylmethyl;

the compound of formula (II) wherein $R^1$ is 4-aminobenzyl and $R^2$ is 3-(2-thiazolylaminocarbonyl)phenylmethyl;

the compound of formula (II) wherein $R^1$ is 4-N-methylaminobenzyl and $R^2$ is 3-(2-thiazolylaminocarbonyl)phenylmethyl;

the compound of formula (II) wherein $R^1$ is 3-N-methylaminobenzyl and $R^2$ is 3-(2-thiazolylaminocarbonyl)phenylmethyl;

the compound of formula (II) wherein $R^1$ is 3-N-methylaminobenzyl and $R^2$ is 3-(2-thiazolylaminocarbonyl)phenylmethyl;

the compound of formula (II) wherein $R^1$ is 3-N,N-dimethylaminobenzyl and $R^2$ is 3-(2-thiazolylaminocarbonyl)phenylmethyl;

the compound of formula (II) wherein $R^1$ is 5-indazolylmethyl and $R^2$ is 3-(2-thiazolylaminocarbonyl)phenylmethyl;

the compound of formula (II) wherein $R^1$ is 3-amino-5-indazolylmethyl and $R^2$ is 3-(2-thiazolylaminocarbonyl)phenylmethyl;

the compound of formula (II) wherein $R^1$ is 3-methyl-5-indazolylmethyl and $R^2$ is 3-(2-thiazolylaminocarbonyl)phenylmethyl;

the compound of formula (II) wherein $R^1$ is 3,4-methylenedioxybenzyl and $R^2$ is 3-(2-thiazolylaminocarbonyl)phenylmethyl;

the compound of formula (II) wherein $R^1$ is 3-pyridinylmethyl and $R^2$ is 3-(2-thiazolylaminocarbonyl)phenylmethyl;

the compound of formula (II) wherein $R^1$ is 3-furanylmethyl and $R^2$ is 3-(2-thiazolylaminocarbonyl)phenylmethyl;

the compound of formula (II) wherein $R^1$ is 3-thienylmethyl and $R^2$ is 3-(2-thiazolylaminocarbonyl)phenylmethyl;

the compound of formula (II) wherein $R^1$ is cyclopropylmethyl and $R^2$ is 3-(4-methyl-2-thiazolylaminocarbonyl)phenylmethyl the compound of formula (II) wherein $R^1$ is n-butyl and $R^2$ is 3-(4-methyl-2-thiazolylaminocarbonyl)phenylmethyl;

the compound of formula (II) wherein $R^1$ is benzyl and $R^2$ is 3-(4-methyl-2-thiazolylaminocarbonyl)phenylmethyl;

the compound of formula (II) wherein $R^1$ is 2-naphthylmethyl and $R^2$ is 3-(4-methyl-2-thiazolylaminocarbonyl)phenylmethyl;

the compound of formula (II) wherein $R^1$ is (3-n-butylamino)benzyl and $R^2$ is 3-(4-methyl-2-thiazolylaminocarbonyl)phenylmethyl;

the compound of formula (II) wherein $R^1$ is 3-aminobenzyl and $R^2$ is 3-(4-methyl-2-thiazolylaminocarbonyl)phenylmethyl;

the compound of formula (II) wherein $R^1$ is 4-aminobenzyl and $R^2$ is 3-(4-methyl-2-thiazolylaminocarbonyl)phenylmethyl;

the compound of formula (II) wherein $R^1$ is 4-N-methylaminobenzyl and $R^2$ is 3-(4-methyl-2-thiazolylaminocarbonyl)phenylmethyl;

the compound of formula (II) wherein $R^1$ is 3-N-methylaminobenzyl and $R^2$ is 3-(4-methyl-2-thiazolylaminocarbonyl)phenylmethyl;

the compound of formula (II) wherein $R^1$ is 3-N-ethylaminobenzyl and $R^2$ is 3-(4-methyl-2-thiazolylaminocarbonyl)phenylmethyl;

the compound of formula (II) wherein $R^1$ is 3-N,N-dimethylaminobenzyl and $R^2$ is 3-(4-methyl-2-thiazolylaminocarbonyl)phenylmethyl;

the compound of formula (II) wherein $R^1$ is 5-indazolylmethyl and $R^2$ is 3-(4-methyl-2-thiazolylaminocarbonyl)phenylmethyl;

the compound of formula (II) wherein $R^1$ is 3-amino-5-indazolylmethyl and $R^2$ is 3-(4-methyl-2-thiazolylaminocarbonyl)phenylmethyl;

the compound of formula (II) wherein $R^1$ is 3-methyl-5-indazolylmethyl and $R^2$ is 3-(4-methyl-2-thiazolylaminocarbonyl)phenylmethyl;

the compound of formula (II) wherein $R^1$ is 3,4-methylenedioxybenzyl and $R^2$ is 3-(4-methyl-2-thiazolylaminocarbonyl)phenylmethyl;

the compound of formula (II) wherein $R^1$ is 3-pyridinylmethyl and $R^2$ is 3-(4-methyl-2-thiazolylaminocarbonyl)phenylmethyl;

the compound of formula (II) wherein $R^1$ is 3-furanylmethyl and $R^2$ is 3-(4-methyl-2-thiazolylaminocarbonyl)phenylmethyl;

the compound of formula (II) wherein $R^1$ is 3-thienylmethyl and $R^2$ is 3-(4-methyl-2-thiazolylaminocarbonyl)phenylmethyl;

the compound of formula (II) wherein $R^1$ is cyclopropylmethyl and $R^2$ is 3-(1,3,4-thiadiazol-2-ylaminocarbonyl)phenylmethyl;

the compound of formula (II) wherein $R^1$ is n-butyl and $R^2$ is 3-(1,3,4-thiadiazol-2-ylaminocarbonyl)phenylmethyl;

the compound of formula (II) wherein $R^1$ is benzyl and $R^2$ is 3-(1,3,4-thiadiazol-2-ylaminocarbonyl)phenylmethyl;

the compound of formula (II) wherein $R^1$ is 2-naphthylmethyl and $R^2$ is 3-(1,3,4-thiadiazol-2-ylaminocarbonyl)phenylmethyl;

the compound of formula (II) wherein $R^1$ is (3-n-butylamino)benzyl and $R^2$ is 3-(1,3,4-thiadiazol-2-ylaminocarbonyl)phenylmethyl;

the compound of formula (II) wherein $R^1$ is 3-aminobenzyl and $R^2$ is 3-(1,3,4-thiadiazol-2-ylaminocarbonyl)phenylmethyl;

the compound of formula (II) wherein $R^1$ is 4-aminobenzyl and $R^2$ is 3-(1,3,4-thiadiazol-2-ylaminocarbonyl)phenylmethyl;

the compound of formula (II) wherein $R^1$ is 4-N-methylaminobenzyl and $R^2$ i s 3-(1,3,4-thiadiazol-2-ylaminocarbonyl)phenylmethyl;

the compound of formula (II) wherein $R^1$ is 3-N-methylaminobenzyl and $R^2$ is 3-(1,3,4-thiadiazol-2-ylaminocarbonyl)phenylmethyl;

the compound of formula (II) wherein $R^1$ is 3-N-ethylaminobenzyl and $R^2$ is 3-(1,3,4-thiadiazol-2-ylaminocarbonyl)phenylmethyl;

the compound of formula (II) wherein $R^1$ is 3-N,N-dimethylaminobenzyl and $R^2$ is 3-(1,3,4-thiadiazol-2-ylaminocarbonyl)phenylmethyl;

the compound of formula (II) wherein $R^1$ is 5-indazolylmethyl and $R^2$ is 3-(1,3,4-thiadiazol-2-ylaminocarbonyl)phenylmethyl;

the compound of formula (II) wherein $R^1$ is 3-amino-5-indazolylmethyl and $R^2$ is 3-(1,3,4-thiadiazol-2-ylaminocarbonyl)phenylmethyl;

the compound of formula (II) wherein $R^1$ is 3-methyl-5-indazolylmethyl and $R^2$ is 3-(1,3,4-thiadiazol-2-ylaminocarbonyl)phenylmethyl;

the compound of formula (II) wherein $R^1$ is 3,4-methylenedioxybenzyl and $R^2$ is 3-(1,3,4-thiadiazol-2-ylaminocarbonyl)phenylmethyl;

the compound of formula (II) wherein $R^1$ is 3-pyridinylmethyl and $R^2$ is 3-(1,3,4-thiadiazol-2-ylaminocarbonyl)phenylmethyl;

the compound of formula (II) wherein $R^1$ is 3-furanylmethyl and $R^2$ is 3-(1,3,4-thiadiazol-2-ylaminocarbonyl)phenylmethyl;

the compound of formula (II) wherein $R^1$ is 3-thienylmethyl and $R^2$ is 3-(1,3,4-thiadiazol-2-ylaminocarbonyl)phenylmethyl;

the compound of formula (II) wherein $R^1$ is cyclopropylmethyl and $R^2$ is 3-(5-methyl-1,3,4-thiadiazol-2-ylaminocarbonyl)phenylmethyl;

the compound of formula (II) wherein $R^1$ is n-butyl and $R^2$ is 3-(5-methyl-1,3,4-thiadiazol-2-ylaminocarbonyl)phenylmethyl;

the compound of formula (II) wherein $R^1$ is benzyl and $R^2$ is 3-(5-methyl-1,3,4-thiadiazol-2-ylaminocarbonyl)phenylmethyl;

the compound of formula (II) wherein $R^1$ is 2-naphthylmethyl and $R^2$ is 3-(5-methyl-1,3,4-thiadiazol-2-ylaminocarbonyl)phenylmethyl;

the compound of formula (II) wherein $R^1$ is (3-n-butylamino)benzyl and $R^2$ is 3-(5-methyl-1,3,4-thiadiazol-2-ylaminocarbonyl)phenylmethyl;

the compound of formula (II) wherein $R^1$ is 3-aminobenzyl and $R^2$ is 3-(5-methyl-1,3,4-thiadiazol-2-ylaminocarbonyl)phenylmethyl;

the compound of formula (II) wherein $R^1$ is 4-aminobenzyl and $R^2$ is 3-(5-methyl-1,3,4-thiadiazol-2-ylaminocarbonyl)phenylmethyl;

the compound of formula (II) wherein $R^1$ is 4-N-methylaminobenzyl and $R^2$ is 3-(5-methyl-1,3,4-thiadiazol-2-ylaminocarbonyl)phenylmethyl;

the compound of formula (II) wherein $R^1$ is 3-N-methylaminobenzyl and $R^2$ is 3-(5-methyl-1,3,4-thiadiazol-2-ylaminocarbonyl)phenylmethyl;

the compound of formula (II) wherein $R^1$ is 3-N-ethylaminobenzyl and $R^2$ is 3-(5-methyl-1,3,4,-thiadiazol-2-ylaminocarbonyl)phenylmethyl;

the compound of formula (II) wherein $R^1$ is 3-N,N-dimethylaminobenzyl and $R^2$ is 3-(5-methyl-1,3,4-thiadiazol-2-ylaminocarbonyl)phenylmethyl;

the compound of formula (II) wherein $R^1$ is 5-indazolylmethyl and $R^2$ is 3-(5-methyl-1,3,4-thiadiazol-2-ylaminocarbonyl)phenylmethyl;

the compound of formula (II) wherein $R^1$ is 3-amino-5-indazolylmethyl and $R^2$ is 3-(5-methyl-1,3,4-thiadiazol-2-ylaminocarbonyl)phenylmethyl;

the compound of formula (II) wherein $R^1$ is 3-methyl-5-indazolylmethyl and $R^2$ is 3-(5-methyl-1,3,4-thiadiazol-2-ylaminocarbonyl)phenylmethyl;

the compound of formula (II) wherein $R^1$ is 3,4-methylenedioxybenzyl and $R^2$ is 3-(5-methyl-1,3,4-thiadiazol-2-ylaminocarbonyl)phenylmethyl;

the compound of formula (II) wherein $R^1$ is 3-pyridinylmethyl and $R^2$ is 3-(5-methyl-1,3,4-thiadiazol-2-ylaminocarbonyl)phenylmethyl;

the compound of formula (II) wherein $R^1$ is 3-furanylmethyl and $R^2$ is 3-(5-methyl-1,3,4-thiadiazol-2-ylaminocarbonyl)phenylmethyl;

the compound of formula (II) wherein $R^1$ is 3-thienylmethyl and $R^2$ is 3-(5-methyl-1,3,4-thiadiazol-2-ylaminocarbonyl)phenylmethyl;

the compound of formula (II) wherein $R^1$ is cyclopropylmethyl and $R^2$ is 3-(5-t-butyl-1,3,4-thiadiazol-2-ylaminocarbonyl)phenylmethyl;

the compound of formula (II) wherein $R^1$ is n-butyl and $R^2$ is 3-(5-t-butyl-1,3,4-thiadiazol-2-ylaminocarbonyl)phenylmethyl;

the compound of formula (II) wherein $R^1$ is benzyl and $R^2$ is 3-(5-t-butyl-1,3,4-thiadiazol-2-ylaminocarbonyl)phenylmethyl;

the compound of formula (II) wherein $R^1$ is 2-naphthylmethyl and $R^2$ is 3-(5-t-butyl-1,3,4-thiadiazol-2-ylaminocarbonyl)phenylmethyl;

the compound of formula (II) wherein $R^1$ is n-butylaminobenzyl and $R^2$ is 3-(5-t-butyl-1,3,4-thiadiazol-2-ylaminocarbonyl)phenylmethyl;

the compound of formula (II) wherein $R^1$ is 3-aminobenzyl and $R^2$ is 3-(5-t-butyl-1,3,4-thiadiazol-2-ylaminocarbonyl)phenylmethyl;

the compound of formula (II) wherein $R^1$ is 4-aminobenzyl and $R^2$ is 3-(5-t-butyl-1,3,4-thiadiazol-2-ylaminocarbonyl)phenylmethyl;

the compound of formula (II) wherein $R^1$ is 4-N-methylaminobenzyl and $R^2$ is 3-(5-t-butyl-1,3,4-thiadiazol-2-ylaminocarbonyl)phenylmethyl;

the compound of formula (II) wherein $R^1$ is 3-N-methylaminobenzyl and $R^2$ is 3-(5-t-butyl-1,3,4-thiadiazol-2-ylaminocarbonyl)phenylmethyl;

the compound of formula (II) wherein $R^1$ is 3-N-ethylaminobenzyl and $R^2$ is 3-(5-t-butyl-1,3,4-thiadiazol-2-ylaminocarbonyl)phenylmethyl;

the compound of formula (II) wherein $R^1$ is 3-N,N-dimethylaminobenzyl and $R^2$ is 3-(5-t-butyl-1,3,4-thiadiazol-2-ylaminocarbonyl)phenylmethyl;

the compound of formula (II) wherein $R^1$ is 5-indazolylmethyl and $R^2$ is 3-(5-t-butyl-1,3,4-thiadiazol-2-ylaminocarbonyl)phenylmethyl;

the compound of formula (II) wherein $R^1$ is 3-amino-5-indazolylmethyl and $R^2$ is 3-(5-t-butyl-1,3,4-thiadiazol-2-ylaminocarbonyl)phenylmethyl;

the compound of formula (II) wherein $R^1$ is 3-methyl-5-indazolylmethyl and $R^2$ is 3-(5-t-butyl-1,3,4-thiadiazol-2-ylaminocarbonyl)phenylmethyl;

the compound of formula (II) wherein $R^1$ is 3,4-methylenedioxybenzyl and $R^2$ is 3-(5-t-butyl-1,3,4-thiadiazol-2-ylaminocarbonyl)phenylmethyl;

the compound of formula (II) wherein $R^1$ is 3-pyridinylmethyl and $R^2$ is 3-(5-t-butyl-1,3,4-thiadiazol-2-ylaminocarbonyl)phenylmethyl;

the compound of formula (II) wherein $R^1$ is 3-furanylmethyl and $R^2$ is 3-(5-t-butyl-1,3,4-thiadiazol-2-ylaminocarbonyl)phenylmethyl;

the compound of formula (II) wherein $R^1$ is 3-thienylmethyl and $R^2$ is 3-(5-t-butyl-1,3,4-thiadiazol-2-ylaminocarbonyl)phenylmethyl;

the compound of formula (II) wherein $R^1$ is cyclopropylmethyl and $R^2$ is 3-(5-methyl-2-thiazolylaminocarbonyl)phenylmethyl;

the compound of formula (II) wherein $R^1$ is n-butyl and $R^2$ is 3-(5-methyl-2-thiazolylaminocarbonyl)phenylmethyl;

the compound of formula (II) wherein $R^1$ is benzyl and $R^2$ is 3-(5-methyl-2-thiazolylaminocarbonyl)phenylmethyl;

the compound of formula (II) wherein $R^1$ is 2-naphthylmethyl and $R^2$ is 3-(5-methyl-2-thiazolylaminocarbonyl)phenylmethyl;

the compound of formula (II) wherein $R^1$ is (3-n-butylamino)benzyl and $R^2$ is 3-(5-methyl-2-thiazolylaminocarbonyl)phenylmethyl;

the compound of formula (II) wherein $R^1$ is 3-aminobenzyl and $R^2$ is 3-(5-methyl-2-thiazolylaminocarbonyl)phenylmethyl;

the compound of formula (II) wherein $R^1$ is 4-aminobenzyl and $R^2$ is 3-(5-methyl-2-thiazolylaminocarbonyl)phenylmethyl;

the compound of formula (II) wherein $R^1$ is 4-N-methylaminobenzyl and $R^2$ is 3-(5-methyl-2-thiazolylaminocarbonyl)phenylmethyl;

the compound of formula (II) wherein $R^1$ is 3-N-methylaminobenzyl and $R^2$ is 3-(5-methyl-2-thiazolylaminocarbonyl)phenylmethyl;

the compound of formula (II) wherein $R^1$ is 3-N-ethylaminobenzyl and $R^2$ is 3-(5-methyl-2-thiazolylaminocarbonyl)phenylmethyl;

the compound of formula (II) wherein $R^1$ is 3-N,N-dimethylaminobenzyl and $R^2$ is 3-(5-methyl-2-thiazolylaminocarbonyl)phenylmethyl;

the compound of formula (II) wherein $R^1$ is 5-indazolylmethyl and $R^2$ is 3-(5-methyl-2-thiazolylaminocarbonyl)phenylmethyl;

the compound of formula (II) wherein $R^1$ is 3-amino-5-indazolylmethyl and $R^2$ is 3-(5-methyl-2-thiazolylaminocarbonyl)phenylmethyl;

the compound of formula (II) wherein $R^1$ is 3-methyl-5-indazolylmethyl and $R^2$ is 3-(5-methyl-2-thiazolylaminocarbonyl)phenylmethyl;

the compound of formula (II) wherein $R^1$ is 3,4-methylenedioxybenzyl and $R^2$ is 3-(5-methyl-2-thiazolylaminocarbonyl)phenylmethyl;

the compound of formula (II) wherein $R^1$ is 3-pyridinylmethyl and $R^2$ is 3-(5-methyl-2-thiazolylaminocarbonyl)phenylmethyl;

the compound of formula (II) wherein $R^1$ is 3-furanylmethyl and $R^2$ is 3-(5-methyl-2-thiazolylaminocarbonyl)phenylmethyl;

the compound of formula (II) wherein $R^1$ is 3-thienylmethyl and $R^2$ is 3-(5-methyl-2-thiazolylaminocarbonyl)phenylmethyl;

the compound of formula (II) wherein $R^1$ is cyclopropylmethyl and $R^2$ is 3-(4,5-dimethyl-2-thiazolylaminocarbonyl)phenylmethyl;

the compound of formula (II) wherein $R^1$ is n-butyl and $R^2$ is 3-(4,5-dimethyl-2-thiazolylaminocarbonyl)phenylmethyl;

the compound of formula (II) wherein $R^1$ is benzyl and $R^2$ is 3-(4,5-dimethyl-2-thiazolylaminocarbonyl)phenylmethyl;

the compound of formula (II) wherein $R^1$ is 2-naphthylmethyl and $R^2$ is 3-(4,5-dimethyl-2-thiazolylaminocarbonyl)phenylmethyl;

the compound of formula (II) wherein $R^1$ is n-butylaminobenzyl and $R^2$ is 3-(4,5-dimethyl-2-thiazolylaminocarbonyl)phenylmethyl;

the compound of formula (II) wherein $R^1$ is 3-aminobenzyl and $R^2$ is 3-(4,5-dimethyl-2-thiazolylaminocarbonyl)phenylmethyl;

the compound of formula (II) wherein $R^1$ is 4-aminobenzyl and $R^2$ is 3-(4,5-dimethyl-2-thiazolylaminocarbonyl)phenylmethyl;

the compound of formula (II) wherein $R^1$ is 4-N-methylaminobenzyl and $R^2$ is 3-(4,5-dimethyl-2-thiazolylaminocarbonyl)phenylmethyl;

the compound of formula (II) wherein $R^1$ is 3-N-methylaminobenzyl and $R^2$ is 3-(4,5-dimethyl-2-thiazolylaminocarbonyl)phenylmethyl;

the compound of formula (II) wherein $R^1$ is 3-N-ethylaminobenzyl and $R^2$ is 3-(4,5-dimethyl-2-thiazolylaminocarbonyl)phenylmethyl;

the compound of formula (II) wherein $R^1$ is 3-N,N-dimethylaminobenzyl and $R^2$ is 3-(4,5-dimethyl-2-thiazolylaminocarbonyl)phenylmethyl;

the compound of formula (II) wherein $R^1$ is 5-indazolylmethyl and $R^2$ is 3-(4,5-dimethyl-2-thiazolylaminocarbonyl)phenylmethyl;

the compound of formula (II) wherein $R^1$ is 3-amino-5-indazolylmethyl and $R^2$ is 3-(4,5-dimethyl-2-thiazolylaminocarbonyl)phenylmethyl;

the compound of formula (II) wherein $R^1$ is 3-methyl-5-indazolylmethyl and $R^2$ is 3-(4,5-dimethyl-2-thiazolylaminocarbonyl)phenylmethyl;

the compound of formula (II) wherein $R^1$ is 3,4-methylenedioxybenzyl and $R^2$ is 3(4,5-dimethyl-2-thiazolylaminocarbonyl)phenylmethyl;

the compound of formula (II) wherein $R^1$ is 3-pyridinylmethyl and $R^2$ is 3-(4,5-dimethyl-2-thiazolylaminocarbonyl)phenylmethyl;

the compound of formula (II) wherein $R^1$ is 3-furanylmethyl and $R^2$ is 3-(4,5-dimethyl-2-thiazolylaminocarbonyl)phenylmethyl;

the compound of formula (II) wherein $R^1$ is 3-thienylmethyl and $R^2$ is 3-(4,5-dimethyl-2-thiazolylaminocarbonyl)phenylmethyl;

the compound of formula (II) wherein $R^1$ is cyclopropylmethyl and $R^2$ is 3-(2-imidazolylaminocarbonyl)phenylmethyl;

the compound of formula (II) wherein $R^1$ is n-butyl and $R^2$ is 3-(2-imidazolylaminocarbonyl)phenylmethyl;

the compound of formula (II) wherein $R^1$ is n-pentyl and $R^2$ is 3-(2-imidazolylaminocarbonyl)phenylmethyl;

the compound of formula (II) wherein $R^1$ is 3-methylbutyl and $R^2$ is 3-(2-imidazolylaminocarbonyl)phenylmethyl;

the compound of formula (II) wherein $R^1$ is 2-methylpropyl and $R^2$ is 3-(2-imidazolylaminocarbonyl)phenylmethyl;

the compound of formula (II) wherein $R^1$ is benzyl and $R^2$ is 3-(2-imidazolylaminocarbonyl)phenylmethyl;

the compound of formula (II) wherein $R^1$ is 2-naphthylmethyl and $R^2$ is 3-(2-imidazolylaminocarbonyl)phenylmethyl;

the compound of formula (II) wherein $R^1$ is (3-n-butylamino)benzyl and $R^2$ is 3-(2-imidazolylaminocarbonyl)phenylmethyl;

the compound of formula (II) wherein $R^1$ is 3-aminobenzyl and $R^2$ is 3-(2-imidazolylaminocarbonyl)phenylmethyl;

the compound of formula (II) wherein $R^1$ is 4-aminobenzyl and $R^2$ is 3-(2-imidazolylaminocarbonyl)phenylmethyl;

the compound of formula (II) wherein $R^1$ is 4-N-methylaminobenzyl and $R^2$ is 3-(2-imidazolylaminocarbonyl)phenylmethyl;

the compound of formula (II) wherein $R^1$ is 3-N-methylaminobenzyl and $R^2$ is 3-(2-imidazolylaminocarbonyl)phenylmethyl;

the compound of formula (II) wherein $R^1$ is 3-N-ethylaminobenzyl and $R^2$ is 3-(2-imidazolylaminocarbonyl)phenylmethyl;

the compound of formula (II) wherein $R^1$ is 3-N,N-dimethylaminobenzyl and $R^2$ is 3-(2-imidazolylaminocarbonyl)phenylmethyl;

the compound of formula (II) wherein $R^1$ is 5-indazolylmethyl and $R^2$ is 3-(2-imidazolylaminocarbonyl)phenylmethyl;

the compound of formula (II) wherein $R^1$ is 3-amino-5-indazolylmethyl and $R^2$ is 3-(2-imidazolylaminocarbonyl)phenylmethyl;

the compound of formula (II) wherein $R^1$ is 3-methyl-5-indazolylmethyl and $R^2$ is 3-(2-imidazolylaminocarbonyl)phenylmethyl;

the compound of formula (II) wherein $R^1$ is 3,4-methylenedioxybenzyl and $R^2$ is 3-(2-imidazolylaminocarbonyl)phenylmethyl;

the compound of formula (II) wherein $R^1$ is 3-pyridinylmethyl and $R^2$ is 3-(2-imidazolylaminocarbonyl)phenylmethyl;

the compound of formula (II) wherein $R^1$ is 3-furanylmethyl and $R^2$ is 3-(2-imidazolylaminocarbonyl)phenylmethyl;

the compound of formula (II) wherein $R^1$ is 3-thienylmethyl and $R^2$ is 3-(2-imidazolylaminocarbonyl)phenylmethyl;

the compound of formula (II) wherein $R^1$ is cyclopropylmethyl and $R^2$ is 3-(2-pyridylaminocarbonyl)phenylmethyl;

the compound of formula (II) wherein $R^1$ is n-butyl and $R^2$ is 3-(2-pyridylaminocarbonyl)phenylmethyl;

the compound of formula (II) wherein $R^1$ is benzyl and $R^2$ is 3-(2-pyridylaminocarbonyl)phenylmethyl;

the compound of formula (II) wherein $R^1$ is 2-naphthylmethyl and $R^2$ is 3-(2-pyridylaminocarbonyl)phenylmethyl;

the compound of formula (II) wherein $R^1$ is (3-n-butylamino)benzyl and $R^2$ is 3-(2-pyridylaminocarbonyl)phenylmethyl;

the compound of formula (II) wherein $R^1$ is 3-aminobenzyl and $R^2$ is 3-(2-pyridylaminocarbonyl)phenylmethyl;

the compound of formula (II) wherein $R^1$ is 4-aminobenzyl and $R^2$ is 3-(2-pyridylaminocarbonyl)phenylmethyl;

the compound of formula (II) wherein $R^1$ is 4-N-methylaminobenzyl and $R^2$ is 3-(2-pyridylaminocarbonyl)phenylmethyl;

the compound of formula (II) wherein $R^1$ is 3-N-methylaminobenzyl and $R^2$ is 3-(2-pyridylaminocarbonyl)phenylmethyl;

the compound of formula (II) wherein $R^1$ is 3-N-ethylaminobenzyl and $R^2$ is 3-(2-pyridylaminocarbonyl)phenylmethyl;

the compound of formula (II) wherein $R^1$ is 3-N,N-dimethylaminobenzyl and $R^2$ is 3-(2-pyridylaminocarbonyl)phenylmethyl;

the compound of formula (II) wherein $R^1$ is 5-indazolylmethyl and $R^2$ is 3-(2-pyridylaminocarbonyl)phenylmethyl;

the compound of formula (II) wherein $R^1$ is 3-amino-5-indazolylmethyl and $R^2$ is 3-(2-pyridylaminocarbonyl)phenylmethyl;

the compound of formula (II) wherein $R^1$ is 3-methyl-5-indazolylmethyl and $R^2$ is 3-(2-pyridylaminocarbonyl)phenylmethyl;

the compound of formula (II) wherein $R^1$ is 3,4-methylenedioxybenzyl and $R^2$ is 3-(2-pyridylaminocarbonyl)phenylmethyl;

the compound of formula (II) wherein $R^1$ is 3-pyridinylmethyl and $R^2$ is 3-(2-pyridylaminocarbonyl)phenylmethyl;

the compound of formula (II) wherein $R^1$ is 3-furanylmethyl and $R^2$ is 3-(2-pyridylaminocarbonyl)phenylmethyl;

the compound of formula (II) wherein $R^1$ is 3-thienylmethyl and $R^2$ is 3-(2-pyridylaminocarbonyl)phenylmethyl;

the compound of formula (II) wherein $R^1$ is cyclopropylmethyl and $R^2$ is 3-(2-benzothiazolylaminocarbonyl)phenylmethyl;

the compound of formula (II) wherein $R^1$ is n-butyl and $R^2$ is 3-(2-benzothiazolylaminocarbonyl)phenylmethyl;

the compound of formula (II) wherein $R^1$ is benzyl and $R^2$ is 3-(2-benzothiazolylaminocarbonyl)phenylmethyl;

the compound of formula (II) wherein $R^1$ is 2-naphthylmethyl and $R^2$ is 3-(2-benzothiazolylaminocarbonyl)phenylmethyl;

the compound of formula (II) wherein $R^1$ is (3-n-butylamino)benzyl and $R^2$ is 3-(2-benzothiazolylaminocarbonyl)phenylmethyl;

the compound of formula (II) wherein $R^1$ is 3-aminobenzyl and $R^2$ is 3-(2-benzothiazolylaminocarbonyl)phenylmethyl;

the compound of formula (II) wherein $R^1$ is 4-aminobenzyl and $R^2$ is 3-(2-benzothiazolylaminocarbonyl)phenylmethyl;

the compound of formula (II) wherein $R^1$ is 4-N-methylaminobenzyl and $R^2$ is 3-(2-benzothiazolylaminocarbonyl)phenylmethyl;

the compound of formula (II) wherein $R^1$ is 3-N-methylaminobenzyl and $R^2$ is 3-(2-benzothiazolylaminocarbonyl)phenylmethyl;

the compound of formula (II) wherein $R^1$ is 3-N-ethylaminobenzyl and $R^2$ is 3-(2-benzothiazolylaminocarbonyl)phenylmethyl;

the compound of formula (II) wherein $R^1$ is 3-N,N-dimethylaminobenzyl and $R^2$ is 3-(2-benzothiazolylaminocarbonyl)phenylmethyl;

the compound of formula (II) wherein $R^1$ is 5-indazolylmethyl and $R^2$ is 3-(2-benzothiazolylaminocarbonyl)phenylmethyl;

the compound of formula (II) wherein $R^1$ is 3-amino-5-indazolylmethyl and $R^2$ is 3-(2-benzothiazolylaminocarbonyl)phenylmethyl;

the compound of formula (II) wherein $R^1$ is 3-methyl-5-indazolylmethyl and $R^2$ is 3-(2-benzothiazolylaminocarbonyl)phenylmethyl;

the compound of formula (II) wherein $R^1$ is 3,4-methylenedioxybenzyl and $R^2$ is 3-(2-benzothiazolylaminocarbonyl)phenylmethyl;

the compound of formula (II) wherein $R^1$ is 3-pyridinylmethyl and $R^2$ is 3-(2-benzothiazolylaminocarbonyl)phenylmethyl;

the compound of formula (II) wherein $R^1$ is 3-furanylmethyl and $R^2$ is 3-(2-benzothiazolylaminocarbonyl)phenylmethyl;

the compound of formula (II) wherein $R^1$ is 3-thienylmethyl and $R^2$ is 3-(2-benzothiazolylaminocarbonyl)phenylmethyl;

the compound of formula (II) wherein $R^1$ is cyclopropylmethyl and $R^2$ is 3-(2-benzimidazolylaminocarbonyl)phenylmethyl;

the compound of formula (II) wherein $R^1$ is n-butyl and $R^2$ is 3-(2-benzimidazolylaminocarbonyl)phenylmethyl;

the compound of formula (II) wherein $R^1$ is benzyl and $R^2$ is 3-(2-benzimidazolylaminocarbonyl)phenylmethyl;

the compound of formula (II) wherein $R^1$ is 2-naphthylmethyl and $R^2$ is 3-(2-benzimidazolylaminocarbonyl)phenylmethyl;

the compound of formula (II) wherein $R^1$ is (3-n-butylamino)benzyl and $R^2$ is 3-(2-benzimidazolylaminocarbonyl)phenylmethyl;

the compound of formula (II) wherein $R^1$ is 3-aminobenzyl and $R^2$ is 3-(2-benzimidazolylaminocarbonyl)phenylmethyl;

the compound of formula (II) wherein $R^1$ is 4-aminobenzyl and $R^2$ is 3-(2-benzimidazolylaminocarbonyl)phenylmethyl;

the compound of formula (II) wherein $R^1$ is 4-N-methylaminobenzyl and $R^2$ is 3-(2-benzimidazolylaminocarbonyl)phenylmethyl;

the compound of formula (II) wherein $R^1$ is 3-N-methylaminobenzyl and $R^2$ is 3-(2-benzimidazolylaminocarbonyl)phenylmethyl;

the compound of formula (II) wherein $R^1$ is 3-N-ethylaminobenzyl and $R^2$ is 3-(2-benzimidazolylaminocarbonyl)phenylmethyl;

the compound of formula (II) wherein $R^1$ is 3-N,N-dimethylaminobenzyl and $R^2$ is 3-(2-benzimidazolylaminocarbonyl)phenylmethyl;

the compound of formula (II) wherein $R^1$ is 5-indazolylmethyl and $R^2$ is 3-(2-benzimidazolylaminocarbonyl)phenylmethyl;

the compound of formula (II) wherein $R^1$ is 3-amino-5-indazolylmethyl and $R^2$ is 3-(2-benzimidazolylaminocarbonyl)phenylmethyl;

the compound of formula (II) wherein $R^1$ is 3-methyl-5-indazolylmethyl and $R^2$ is 3-(2-benzimidazolylaminocarbonyl)phenylmethyl;

the compound of formula (II) wherein $R^1$ is 3,4-methylenedioxybenzyl and $R^2$ is 3-(2-benzimidazolylaminocarbonyl)phenylmethyl;

the compound of formula (II) wherein $R^1$ is 3-pyridinylmethyl and $R^2$ is 3-(2-benzimidazolylaminocarbonyl)phenylmethyl;

the compound of formula (II) wherein $R^1$ is 3-furanylmethyl and $R^2$ is 3-(2-benzimidazolylaminocarbonyl)phenylmethyl;

the compound of formula (II) wherein $R^1$ is 3-thienylmethyl and $R^2$ is 3-(2-benzimidazolylaminocarbonyl)phenylmethyl;

the compound of formula (II) wherein $R^1$ is cyclopropylmethyl and $R^2$ is 3-(2-thiazolyloxy)phenylmethyl;

the compound of formula (II) wherein $R^1$ is n-butyl and $R^2$ is 3-(2-thiazolyloxy)phenylmethyl;

the compound of formula (II) wherein $R^1$ is benzyl and $R^2$ is 3-(2-thiazolyloxy)phenylmethyl;

the compound of formula (II) wherein $R^1$ is 2-naphthylmethyl and $R^2$ is 3-(2-thiazolyloxy)phenylmethyl;

the compound of formula (II) wherein $R^1$ is (3-n-butylamino)benzyl and $R^2$ is 3-(2-thiazolyloxy)phenylmethyl;

the compound of formula (II) wherein $R^1$ is 3-aminobenzyl and $R^2$ is 3-(2-thiazolyloxy)phenylmethyl;

the compound of formula (II) wherein $R^1$ is 4-aminobenzyl and $R^2$ is 3-(2-thiazolyloxy)phenylmethyl;

the compound of formula (II) wherein $R^1$ is 4-N-methylaminobenzyl and $R^2$ is 3-(2-thiazolyloxy)phenylmethyl;

the compound of formula (II) wherein $R^1$ is 3-N-methylaminobenzyl and $R^2$ is 3-(2-thiazolyloxy)phenylmethyl;

the compound of formula (II) wherein $R^1$ is 3-N-ethylaminobenzyl and $R^2$ is 3-(2-thiazolyloxy)phenylmethyl;

the compound of formula (II) wherein $R^1$ is 3-N,N-dimethylaminobenzyl and $R^2$ is 3-(2-thiazolyloxy)phenylmethyl;

the compound of formula (II) wherein $R^1$ is 5-indazolylmethyl and $R^2$ is 3-(2-thiazolyloxy)phenylmethyl;

the compound of formula (II) wherein $R^1$ is 3-amino-5-indazolylmethyl and $R^2$ is 3-(2-thiazolyloxy)phenylmethyl;

the compound of formula (II) wherein $R^1$ is 3-methyl-5-indazolylmethyl and $R^2$ is 3-(2-thiazolyloxy)phenylmethyl;

the compound of formula (II) wherein $R^1$ is 3,4-methylenedioxybenzyl and $R^2$ is 3-(2-thiazolyloxy)phenylmethyl;

the compound of formula (II) wherein $R^1$ is 3-pyridinylmethyl and $R^2$ is 3-(2-thiazolyloxy)phenylmethyl;

the compound of formula (II) wherein $R^1$ is 3-furanylmethyl and $R^2$ is 3-(2-thiazolyloxy)phenylmethyl;

the compound of formula (II) wherein $R^1$ is 3-thienylmethyl and $R^2$ is 3-(2-thiazolyloxy) phenylmethyl;

the compound of formula (II) wherein $R^1$ is cyclopropylmethyl and $R^2$ is 3-[(3-methyl-2-pyridinyl) aminocarbonyl]phenylmethyl;

the compound of formula (II) wherein $R^1$ is n-butyl and $R^2$ is 3-[(3-methyl-2-pyridinyl)aminocarbonyl] phenylmethyl;

the compound of formula (II) wherein $R^1$ is benzyl and $R^2$ is 3-[(3-methyl-2-pyridinyl)aminocarbonyl] phenylmethyl;

the compound of formula (II) wherein $R^1$ is 2-naphthylmethyl and $R^2$ is 3-[(3-methyl-2-pyridinyl) aminocarbonyl]phenylmethyl;

the compound of formula (II) wherein $R^1$ is (3-n-butylamino)benzyl and $R^2$ is 3-[(3-methyl-2-pyridinyl) aminocarbonyl]phenylmethyl;

the compound of formula (II) wherein $R^1$ is 3-aminobenzyl and $R^2$ is 3-[(3-methyl-2-pyridinyl) aminocarbonyl]phenylmethyl;

the compound of formula (II) wherein $R^1$ is 4-aminobenzyl and $R^2$ is 3-[(3-methyl-2-pyridinyl) aminocarbonyl]phenylmethyl;

the compound of formula (II) wherein $R^1$ is 4-N-methylaminobenzyl and $R^2$ is 3-[(3-methyl-2-pyridinyl)aminocarbonyl]phenylmethyl;

the compound of formula (II) wherein $R^1$ is 3-N-methylaminobenzyl and $R^2$ is 3-[(3-methyl-2-pyridinyl)aminocarbonyl]phenylmethyl;

the compound of formula (II) wherein $R^1$ is 3-N-ethylaminobenzyl and $R^2$ is 3-[(3-methyl-2-pyridinyl) aminocarbonyl]phenylmethyl;

the compound of formula (II) wherein $R^1$ is 3-N,N-dimethylaminobenzyl and $R^2$ is 3-[(3-methyl-2-pyridinyl)aminocarbonyl]phenylmethyl;

the compound of formula (II) wherein $R^1$ is 5-indazolylmethyl and $R^2$ is 3-[(3-methyl-2-pyridinyl) aminocarbonyl]phenylmethyl;

the compound of formula (II) wherein $R^1$ is 3-amino-5-indazolylmethyl and $R^2$ is 3-[(3-methyl-2-pyridinyl) aminocarbonyl]phenylmethyl;

the compound of formula (II) wherein $R^1$ is 3-methyl-5-indazolylmethyl and $R^2$ is 3-[(3-methyl-2-pyridinyl) aminocarbonyl]phenylmethyl;

the compound of formula (II) wherein $R^1$ is 3,4-methylenedioxybenzyl and 3-[(3-methyl-2-pyridinyl) aminocarbonyl]phenylmethyl;

the compound of formula (II) wherein $R^1$ is 3-pyridinylmethyl and $R^2$ is 3-[(3-methyl-2-pyridinyl) aminocarbonyl]phenylmethyl;

the compound of formula (II) wherein $R^1$ is 3-furanylmethyl and $R^2$ is 3-[(3-methyl-2-pyridinyl) aminocarbonyl]phenylmethyl;

the compound of formula (II) wherein $R^1$ is 3-thienylmethyl and $R^2$ is 3-[(3-methyl-2-pyridinyl) aminocarbonyl]phenylmethyl;

the compound of formula (II) wherein $R^1$ is cyclopropylmethyl and $R^2$ is 3-(2-pyridinyloxy)phenylmethyl;

the compound of formula (II) wherein $R^1$ is n-butyl and $R^2$ is 3-(2-pyridinyloxy)phenylmethyl;

the compound of formula (II) wherein $R^1$ is benzyl and $R^2$ is 3-(2-pyridinyloxy)phenylmethyl;

the compound of formula (II) wherein $R^1$ is 2-naphthylmethyl and $R^2$ is 3-(2-pyridinyloxy) phenylmethyl;

the compound of formula (II) wherein $R^1$ is (3-n-butylamino)benzyl and $R^2$ is 3-(2-pyridinyloxy) phenylmethyl;

the compound of formula (II) wherein $R^1$ is 3-aminobenzyl and $R^2$ is 3-(2-pyridinyloxy) phenylmethyl;

the compound of formula (II) wherein $R^1$ is 4-aminobenzyl and $R^2$ is 3-(2-pyridinyloxy) phenylmethyl;

the compound of formula (II) wherein $R^1$ is 4-N-methylaminobenzyl and $R^2$ is 3-(2-pyridinyloxy) phenylmethyl;

the compound of formula (II) wherein $R^1$ is 3-N-methylaminobenzyl and $R^2$ is 3-(2-pyridinyloxy) phenylmethyl;

the compound of formula (II) wherein $R^1$ is 3-N-ethylaminobenzyl and $R^2$ is 3-(2-pyridinyloxy) phenylmethyl;

the compound of formula (II) wherein $R^1$ is 3-N,N-dimethylaminobenzyl and $R^2$ is 3-(2-pyridinyloxy) phenylmethyl;

the compound of formula (II) wherein $R^1$ is 5-indazolylmethyl and $R^2$ is 3-(2-pyridinyloxy) phenylmethyl;

the compound of formula (II) wherein $R^1$ is 3-amino-5-indazolylmethyl and $R^2$ is 3-(2-pyridinyloxy) phenylmethyl;

the compound of formula (II) wherein $R^1$ is 3-methyl-5-indazolylmethyl and $R^2$ is 3-(2-pyridinyloxy) phenylmethyl;

the compound of formula (II) wherein $R^1$ is 3,4-methylenedioxybenzyl and $R^2$ is 3-(2-pyridinyloxy) phenylmethyl;

the compound of formula (II) wherein $R^1$ is 3-pyridinylmethyl and $R^2$ is 3-(2-pyridinyloxy) phenylmethyl;

the compound of formula (II) wherein $R^1$ is 3-furanylmethyl and $R^2$ is 3-(2-pyridinyloxy) phenylmethyl;

the compound of formula (II) wherein $R^1$ is 3-thienylmethyl and $R^2$ is 3-(2-pyridinyloxy) phenylmethyl;

the compound of formula (II) wherein $R^1$ is cyclopropylmethyl and $R^2$ is 3-[(4-methyl-2-pyridinyl) aminocarbonyl]phenylmethyl;

the compound of formula (II) wherein $R^1$ is n-butyl and $R^2$ is 3-[(4-methyl-2-pyridinyl)aminocarbonyl] phenylmethyl;

the compound of formula (II) wherein $R^1$ is benzyl and $R^2$ is 3-[(4-methyl-2-pyridinyl)aminocarbonyl] phenylmethyl;

the compound of formula (II) wherein $R^1$ is 2-naphthylmethyl and $R^2$ is 3-[(4-methyl-2-pyridinyl) aminocarbonyl]phenylmethyl;

the compound of formula (II) wherein $R^1$ is (3-n-butylamino)benzyl and $R^2$ is 3-[(4-methyl-2-pyridinyl) aminocarbonyl]phenylmethyl;

the compound of formula (II) wherein $R^1$ is 3-aminobenzyl and $R^2$ is 3-[(4-methyl-2-pyridinyl) aminocarbonyl]phenylmethyl;

the compound of formula (II) wherein $R^1$ is 4-aminobenzyl and $R^2$ is 3-[(4-methyl-2-pyridinyl) aminocarbonyl]phenylmethyl;

the compound of formula (II) wherein $R^1$ is 4-N-methylaminobenzyl and $R^2$ is 3-[(4-methyl-2-pyridinyl)aminocarbonyl]phenylmethyl;

the compound of formula (II) wherein $R^1$ is 3-N-methylaminobenzyl and $R^2$ is 3-[(4-methyl-2-pyridinyl)aminocarbonyl]phenylmethyl;

the compound of formula (II) wherein $R^1$ is 3-N-ethylaminobenzyl and $R^2$ is 3-[(4-methyl-2-pyridinyl) aminocarbonyl]phenylmethyl;

the compound of formula (II) wherein $R^1$ is 3-N,N-dimethylaminobenzyl and $R^2$ is 3-[(4-methyl-2-pyridinyl)aminocarbonyl]phenylmethyl;

the compound of formula (II) wherein $R^1$ is 5-indazolylmethyl and $R^2$ is 3-[(4-methyl-2-pyridinyl) aminocarbonyl]phenylmethyl;

the compound of formula (II) wherein $R^1$ is 3-amino-5-indazolylmethyl and $R^2$ is 3-[(4-methyl-2-pyridinyl) aminocarbonyl]phenylmethyl;

the compound of formula (II) wherein $R^1$ is 3-methyl-5-indazolylmethyl and $R^2$ is 3-[(4-methyl-2-pyridinyl) aminocarbonyl]phenylmethyl;

the compound of formula (II) wherein $R^1$ is 3,4-methylenedioxybenzyl and $R^2$ is 3-[(4-methyl-2-pyridinyl)aminocarbonyl]phenylmethyl;

the compound of formula (II) wherein $R^1$ is 3-pyridinylmethyl and $R^2$ is 3-[(4-methyl-2-pyridinyl) aminocarbonyl]phenylmethyl;

the compound of formula (II) wherein $R^1$ is 3-furanylmethyl and $R^2$ is 3-[(4-methyl-2-pyridinyl) aminocarbonyl]phenylmethyl;

the compound of formula (II) wherein $R^1$ is 3-thienylmethyl and $R^2$ is 3-[(4-methyl-2-pyridinyl) aminocarbonyl]phenylmethyl;

the compound of formula (II) wherein $R^1$ is cyclopropylmethyl and $R^2$ is 3-[(5-methyl-2-pyridinyl) aminocarbonyl]phenylmethyl;

the compound of formula (II) wherein $R^1$ is n-butyl and $R^2$ is 3-[(5-methyl-2-pyridinyl)aminocarbonyl] phenylmethyl;

the compound of formula (II) wherein $R^1$ is benzyl and $R^2$ is 3-[(5-methyl-2-pyridinyl)aminocarbonyl] phenylmethyl;

the compound of formula (II) wherein $R^1$ is 2-naphthylmethyl and $R^2$ is 3-[(5-methyl-2-pyridinyl) aminocarbonyl]phenylmethyl;

the compound of formula (II) wherein $R^1$ is (3-n-butylamino)benzyl and $R^2$ is 3-[(5-methyl-2-pyridinyl) aminocarbonyl]phenylmethyl;

the compound of formula (II) wherein $R^1$ is 3-aminobenzyl and $R^2$ is 3-[(5-methyl-2-pyridinyl) aminocarbonyl]phenylmethyl;

the compound of formula (II) wherein $R^1$ is 4-aminobenzyl and $R^2$ is 3-[(5-methyl-2-pyridinyl) aminocarbonyl]phenylmethyl;

the compound of formula (II) wherein $R^1$ is 4-N-methylaminobenzyl and $R^2$ is 3-[(5-methyl-2-pyridinyl)aminocarbonyl]phenylmethyl;

the compound of formula (II) wherein $R^1$ is 3-N-methylaminobenzyl and $R^2$ is 3-[(5-methyl-2-pyridinyl)aminocarbonyl]phenylmethyl;

the compound of formula (II) wherein $R^1$ is 3-N-ethylaminobenzyl and $R^2$ is 3-[(5-methyl-2-pyridinyl) aminocarbonyl]phenylmethyl;

the compound of formula (II) wherein $R^1$ is 3-N,N-dimethylaminobenzyl and $R^2$ is 3-[(5-methyl-2-pyridinyl)aminocarbonyl]phenylmethyl;

the compound of formula (II) wherein $R^1$ is 5-indazolylmethyl and $R^2$ is 3-[(5-methyl-2-pyridinyl) aminocarbonyl]phenylmethyl;

the compound of formula (II) wherein $R^1$ is 3-amino-5-indazolylmethyl and $R^2$ is 3-[(5-methyl-2-pyridinyl) aminocarbonyl]phenylmethyl;

the compound of formula (II) wherein $R^1$ is 3-methyl-5-indazolylmethyl and $R^2$ is 3-[(5-methyl-2-pyridinyl) aminocarbonyl]phenylmethyl;

the compound of formula (II) wherein $R^1$ is 3,4-methylenedioxybenzyl and $R^2$ is 3-[(5-methyl-2-pyridinyl)aminocarbonyl]phenylmethyl;

the compound of formula (II) wherein $R^1$ is 3-pyridinylmethyl and $R^2$ is 3-[(5-methyl-2-pyridinyl) aminocarbonyl]phenylmethyl;

the compound of formula (II) wherein $R^1$ is 3-furanylmethyl and $R^2$ is 3-[(5-methyl-2-pyridinyl) aminocarbonyl]phenylmethyl;

the compound of formula (II) wherein $R^1$ is 3-thienylmethyl and $R^2$ is 3-[(5-methyl-2-pyridinyl) aminocarbonyl]phenylmethyl;

the compound of formula (II) wherein $R^1$ is cyclopropylmethyl and $R^2$ is 3-[(6-methyl-2-pyridinyl) aminocarbonyl]phenylmethyl;

the compound of formula (II) wherein $R^1$ is n-butyl and $R^2$ is 3-[(6-methyl-2-pyridinyl)aminocarbonyl] phenylmethyl;

the compound of formula (II) wherein $R^1$ is benzyl and $R^2$ is 3-[(6-methyl-2-pyridinyl)aminocarbonyl] phenylmethyl;

the compound of formula (II) wherein $R^1$ is 2-naphthylmethyl and $R^2$ is 3-[(6-methyl-2-pyridinyl) aminocarbonyl]phenylmethyl;

the compound of formula (II) wherein $R^1$ is (3-n-butylamino)benzyl and $R^2$ is 3-[(6-methyl-2-pyridinyl) aminocarbonyl]phenylmethyl;

the compound of formula (II) wherein $R^1$ is 3-aminobenzyl and $R^2$ is 3-[(6-methyl-2-pyridinyl) aminocarbonyl]phenylmethyl;

the compound of formula (II) wherein $R^1$ is 4-aminobenzyl and $R^2$ is 3-[(6-methyl-2-pyridinyl) aminocarbonyl]phenylmethyl;

the compound of formula (II) wherein $R^1$ is 4-N-methylaminobenzyl and $R^2$ is 3-[(6-methyl-2-pyridinyl)aminocarbonyl]phenylmethyl;

the compound of formula (II) wherein $R^1$ is 3-N-methylaminobenzyl and $R^2$ is 3-[(6-methyl-2-pyridinyl)aminocarbonyl]phenylmethyl;

the compound of formula (II) wherein $R^1$ is 3-N-ethylaminobenzyl and $R^2$ is 3-[(6-methyl-2-pyridinyl) aminocarbonyl]phenylmethyl;

the compound of formula (II) wherein $R^1$ is 3-N,N-dimethylaminobenzyl and $R^2$ is 3-[(6-methyl-2-pyridinyl)aminocarbonyl]phenylmethyl;

the compound of formula (II) wherein $R^1$ is 5-indazolylmethyl and $R^2$ is 3-[(6-methyl-2-pyridinyl) aminocarbonyl]phenylmethyl;

the compound of formula (II) wherein $R^1$ is 3-amino-5-indazolylmethyl and $R^2$ is 3-[(6-methyl-2-pyridinyl)aminocarbonyl]phenylmethyl;

the compound of formula (II) wherein $R^1$ is 3-methyl-5-indazolylmethyl and $R^2$ is 3-[(6-methyl-2-pyridinyl)aminocarbonyl]phenylmethyl;

the compound of formula (II) wherein $R^1$ is 3,4-methylenedioxybenzyl and $R^2$ is 3-[(6-methyl-2-pyridinyl)aminocarbonyl]phenylmethyl;

the compound of formula (II) wherein $R^1$ is 3-pyridinylmethyl and $R^2$ is 3-[(6-methyl-2-pyridinyl)aminocarbonyl]phenylmethyl;

the compound of formula (II) wherein $R^1$ is 3-furanylmethyl and $R^2$ is 3-[(6-methyl-2-pyridinyl)aminocarbonyl]phenylmethyl;

the compound of formula (II) wherein $R^1$ is 3-thienylmethyl and $R^2$ is 3-[(6-methyl-2-pyridinyl)aminocarbonyl]phenylmethyl.

The present invention also provides a pharmaceutical composition comprising a pharmaceutically acceptable carrier and a therapeutically effective amount of a compound of formula (I) as described above.

In the present invention it has been discovered that the compounds of formula (I) above are useful as inhibitors of HIV protease and similar retroviral proteases, and for the inhibition of HIV and the treatment of HIV infection and similar retrovirus infections.

The present invention also provides methods for the treatment of HIV infection comprising administering to a host infected with HIV a pharmaceutically or therapeutically effective or acceptable amount of a compound of formula (I) as described above. By therapeutically effective amount, it is meant an amount of a compound of the present invention effective to inhibit HIV infection or treat the symptoms of infection in a host.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral replication and/or HIV protease, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV protease, the compounds of the present invention may also be useful as diagnostic reagents in diagnostic assays for the detection of HIV protease. Thus, inhibition of the protease activity in an assay (such as the assays described herein) by a compound of the present invention would be indicative of the presence of HIV protease and HIV virus.

The present invention also provides a method of treating HIV infection in a mammal comprising administering to the mammal a therapeutically effective amount of a combination of: (i) an HIV protease inhibitor compound of formula (I); and (ii) an HIV reverse transcriptase inhibitor.

The administration of a cyclic HIV protease inhibitor of formula (I) (component (i)) in combination with an HIV reverse transciptase (RT) inhibitor (component (ii)) may provide a synergistic effect in inhibiting the replication of HIV. Thus, the HIV inhibitory effects of the compound of formula (I) administered in combination with the RT inhibitor may be greater than the additive effect of each agent when administered alone. The combination treatment using a compound of formula (I) in combination with a RT inhibitor permits the use of lower doses of each component, with reduced adverse, toxic effects of each component. A lower dosage minimizes the potential of side effects of the compounds, thereby providing an increased margin of safety relative to the margin of safety for each component when used as a single agent. In view of the toxicity associated with the presently approved therapies for HIV, such as AZT, the present invention provides an important advantage over current therapies for HIV.

By "administered in combination" or "combination" when referring to component (i) and component (ii) of the present invention, it is meant that the components are administered concurrently to the cell or mammal being treated. When administered in combination each component may be administered at the same time or sequentially in any order at different points in time. Thus, component (i) and component (ii) may be administered separately but sufficiently closely in time so as to provide the desired HIV inhibitory effect.

This invention also includes pharmaceutical kits comprising or consisting essentially of a pharmaceutical composition comprising the cyclic HIV protease inhibitor compounds of formula (I) together with a pharmaceutical composition comprising an HIV RT inhibitor, and to methods of using such pharmaceutical kits for the inhibition of HIV and treatment of HIV infection.

This invention also includes combination products comprising pharmaceutical compositions comprising a cyclic HIV protease inhibitor compound of formula (I) in physical combination or in a single dosage unit with an HIV RT inhibitor, to pharmaceutical kits containing these combination products, and to methods of using these combination products for the inhibition of HIV and treatment of HIV infection.

HIV reverse transcriptase (RT) inhibitors useful in the method, combination products, and pharmaceutical kits of the present invention include, but are not limited to: nucleoside analogs, such as 3'-azido-3'-deoxythymidine (AZT, zidovidine), 2',3'-dideoxyinosine (DDI, ddI), 2',3'-dideoxycytidine (DDC, ddC), d4T, and 3TC; and non-nucleoside RT inhibitors,such as TIBO derivatives; BI-RG-587 and derivatives thereof; nevirapine; L-697,661 and derivatives thereof; LY 73497; Ro 18,893; L-743,726 and derivatives thereof; and L-738,272 and derivatives thereof.

The preparation of L-743,726 and derivatives thereof is disclosed in European patent application Publication Number 582,455.

The preparation of L-738,272 and derivatives thereof is disclosed in European Patent Application Number 93201232.1

The preparation of AZT is described by Chu et al., Tetrahedron Letters 29:5349 (1988). AZT is available commercially as "Retrovir®", for which the product information, including dosage and administration, is given in Physicians' Desk Reference, 46th Edition, 1992, pp. 802–808.

The preparation of DDI is described by Webb et al. in Nucleosides Nucleotides 7, 147 (1988).

The preparation of DDC is described by Horwitz et al. in J. Org. Chem. 32:817 (1967).

The preparation of TIBO derivatives is described by Pauwels et al. in Nature 343:470 (1990).

The preparation of BI-RG-587 is described by Merluzzi et al. in Science 250:1411 (1990).

The preparation of L-697,661 and derivatives thereof is described by Goldman et al. in Proc. Natl. Acad. Sci. USA 88:6863 (1991).

The preparation and RT inhibitory activity of d4T is described by Mansuri et al. in J. Med. Chem. 32:461 (1989).

The preparation of 3TC is described by Storer et al. in Nucleosides Nucleotides 12:225 (1993).

The disclosures of all of the references cited herein are hereby incorporated herein by reference in their entirety.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, but not limited to, $R^1$, $R^5$, $R^7$, $R^9$, m, n etc.) occurs more than one time in any constituent or in formula (I) or (II), or any other formula herein, its definition on each occurrence is independent of its definition at every other occurrence. Thus, for example, if a group is shown to be substituted with 0–2 $R^9$, then said group may optionally be substituted with up to two $R^9$ and $R^9$ at each occurrence is selected independently from the defined list of possible $R^9$. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example $—C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula I. Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl) aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocycles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, or isatinoyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, thiazolyl, 1,3,4-thiadiazolyl, oxazolyl, 1,3,4-oxadiazolyl, benzothiazolyl, benzotriazolyl, benzisoxazolyl, or benzoxazolinyl.

When a bond to a substituent is shown to cross the bond connecting two atoms in a ring, then such substituent may be bonded to any atom on the ring. When a substituent is listed without indicating the atom via which such substituent is bonded to the rest of the compound of formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of formula (I) via any atom in such piperazinyl, piperidinyl, tetrazolyl group. Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, the term "amine protecting group" means any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

As used herein, the term "hydroxy protecting group" (or "O-protected") refers to any group known in the art of organic synthesis for the protection of hydroxyl groups. As used herein, the term "hydroxy protecting group reagent" refers to any reagent known in the art of organic synthesis for the protection of hydroxy groups which may be reacted with an hydroxy to provide an hydroxy group protected with an hydroxy protecting group. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Hydroxy protecting groups also include diol protecting groups, including cyclic acetal protecting groups. As used herein "cyclic acetal protecting group" includes any protecting group known in the art of organic synthesis for the protection of 1,2-diol group through formation of a cyclic acetal or cyclic ketal group. Such protecting groups include, but are not limited to, those listed in Greene and Wuts, "Protective Groups in Organic Synthesis", John Wiley & Sons, New York (1991), the disclosure of which is hereby incorporated by reference. Examples of such cyclic acetal 1,2-diol protecting groups are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, and methoxymethylene acetal. Such ketal rings or ketal protecting groups are well known in the art of organic synthesis and typically include, for example, substituted or unsubstituted carbocyclic diethers, dithioethers, mixed ethers, enol ethers or ketones.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts of the compounds of formula (I) include the conventional non-toxic salts or the quaternary ammonium salts of the compounds of formula (I) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula (I) which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below.

The compounds of the present invention may be synthesized using the general synthetic procedures described below. Each of the references cited below are hereby incorporated herein by reference.

The compounds of the present invention are prepared by modifications of the procedures disclosed for the synthesis of cyclic urea HIV protease inhibitors in PCT Patent Applications WO 93/07128 published Apr. 15, 1993 and WO 94/19329 published Sep. 1, 1994, and in copending commonly assigned U.S. patent application U.S. Ser. No. 08/197,630 filed Feb. 16, 1994. The disclosure of these references is incorporated herein by reference.

Compounds of formula I wherein Y is $-(CH_2)_nCONH-$, are prepared from carboxylic acids of formula (III)

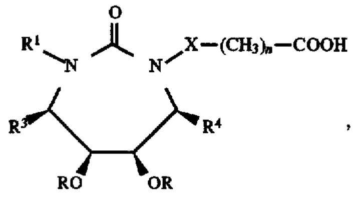

(III)

R = Protecting group wherein $R^1$ can be $-X(CH_2)_nCOOH$ or as defined above for compounds of formula I; $R^3$, $R^4$ and X are as defined above for compounds of formula I; and R is a hydroxyl or diol protecting group, by condensation with appropriately substituted 2-aminoheteroaryls to form an amide. The condensation is carried out using any of the many methods for the formation of amide bonds known to one skilled in the art of organic synthesis. These methods include but are not limited to use of standard coupling procedures such as the azide method, mixed carbonic acid anhydride (isobutyl chloroformate) method, carbodiimide (dicyclohexylcarbodiimide (DCC), diisopropylcarbodiimide, or 1-(3-dimethylaminopropyl)-3-ethylcarbodiimide hydrochloride (EDC)) method, active ester (p-nitrophenyl ester, N-hydroxysuccinic imido ester) method, carbonyldiimidazole method, or phosphorus reagents such as BOP-Cl. Some of these methods (especially the carbodiimide) can be enhanced by the addition of 1-hydroxybenzotriazole. Alternatively the desired amides can be prepared by conversion of acid (IIIc) to the corresponding acid chloride and treatment of the acyl chloride with a 2-aminoheteroaryl in the presence of a base. Methods for conversion of carboxylic acids to acid chlorides are described in (March, Adv. Org. Chem. 1985, p. 1146, J. Wiley & Son, USA) and include, for example, treatment of the acid with oxalyl chloride in the presence of a catalytic amount of N,N'-dimethylformamide.

Illustrative examples of the synthesis of compounds of the present invention by the above methods are depicted in Schemes 1 and 2 below.

Scheme 1
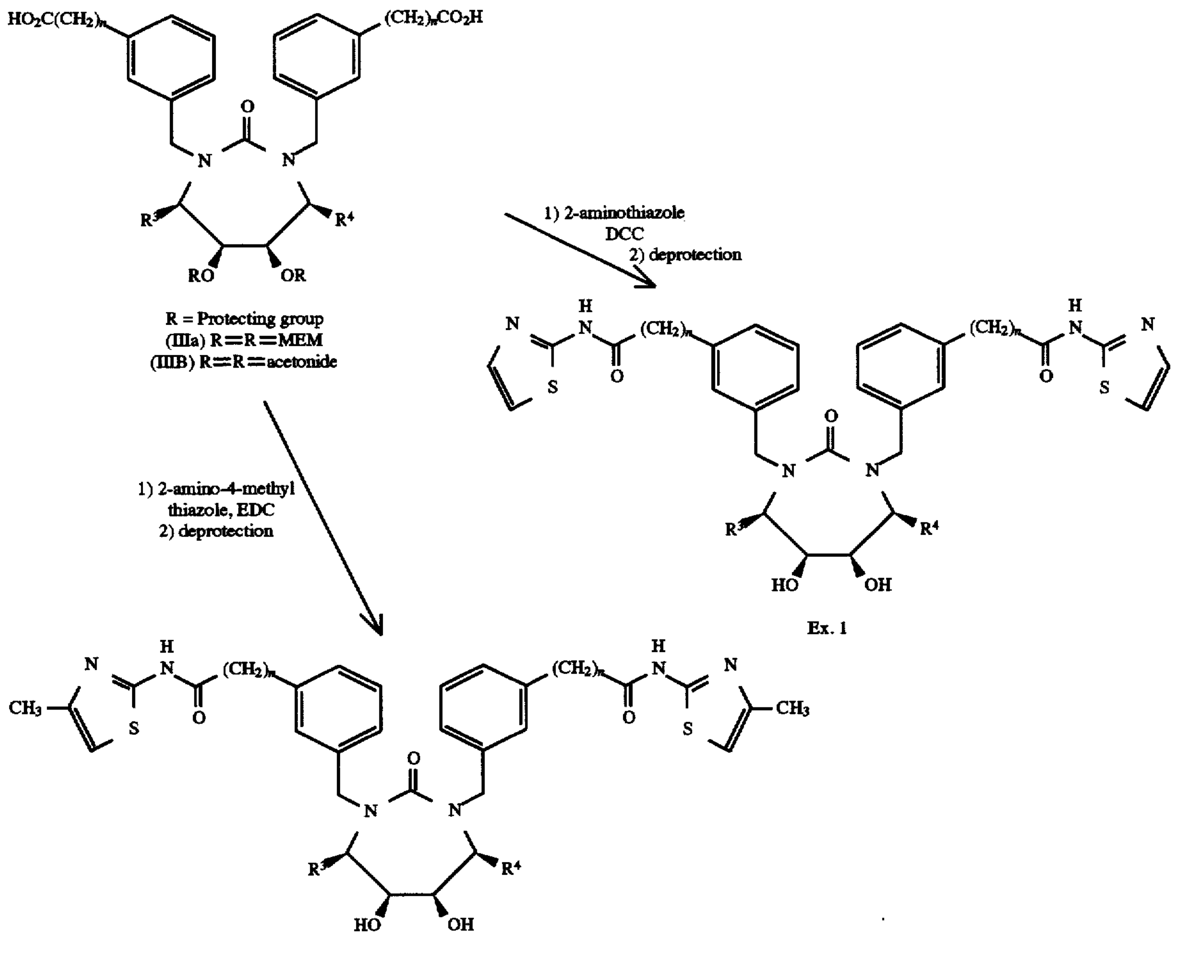
Ex. 1
Ex. 2
Scheme 2
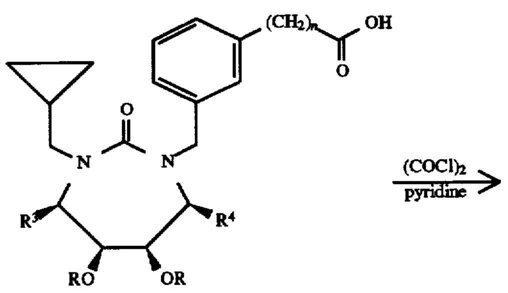
R = protecting group
(IIIc) R=R=acetonide
-continued
Scheme 2
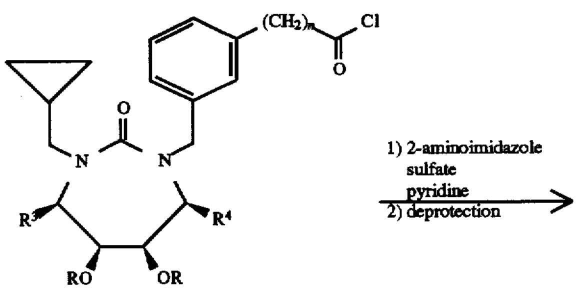
IV -continued Scheme 2

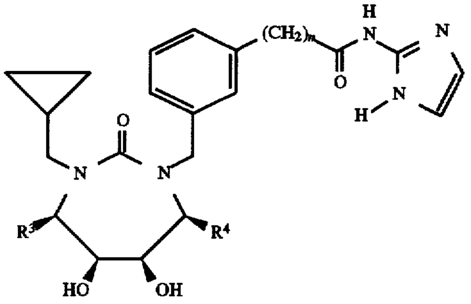

Ex. 39

Compounds of formula I wherein Y is —$(CH_2)_nO$— or —$(CH_2)_nN$—, may be prepared by reaction of an appropriate alcohol or amine of formula (IV):

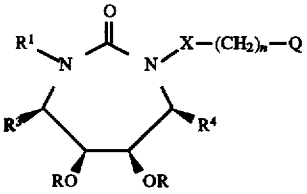

(V)

R = Protecting group
Q = OH or $NH_2$ wherein $R^1$ can be —$X(CH_2)_nQ$ or as defined above for compounds of formula I; $R^3$, $R^4$ and X are as defined above for compounds of formula I; R is a hydroxyl or diol protecting group, and Q is —OH or —$NH_2$, with a bromoheteroaryl in the presence of a strong base, such as sodium hydride as shown in Scheme 3.

Scheme 3

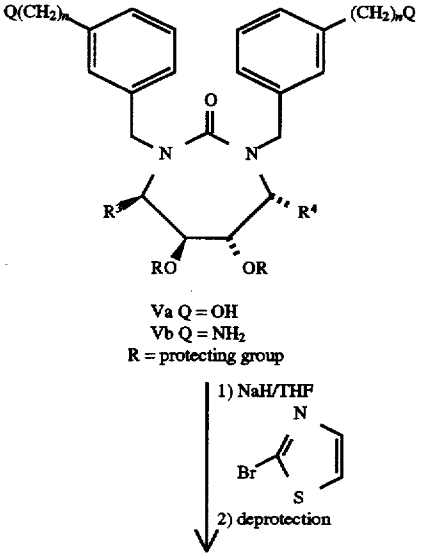

Va Q = OH
Vb Q = $NH_2$
R = protecting group

-continued

Scheme 3

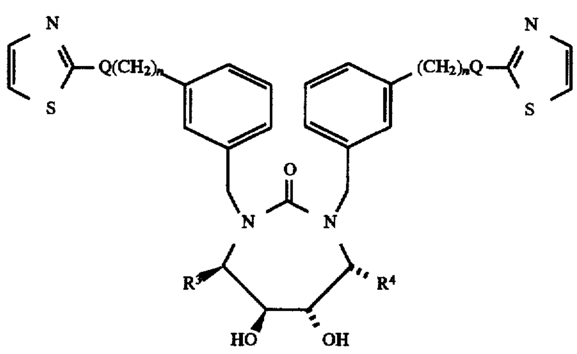

VIa Q = O
VIb Q = NH

Compounds of formula I wherein Y is —$(CH_2)_nOCONH$— or —$(CH_2)_nNHCONH$—, may also be prepared from alcohols or amines of formula (IVa) and (IVb), respectively, as outlined in Scheme 4. Activation of a compound of formula (IVa) or (IVb) with phenylchloroformate in the presence of triethylamine followed by treatment of the intermediates 4a and 4b, with an aminoheteroaryl provides the desired carbamates 4c or ureas 4d, respectively.

Scheme 4

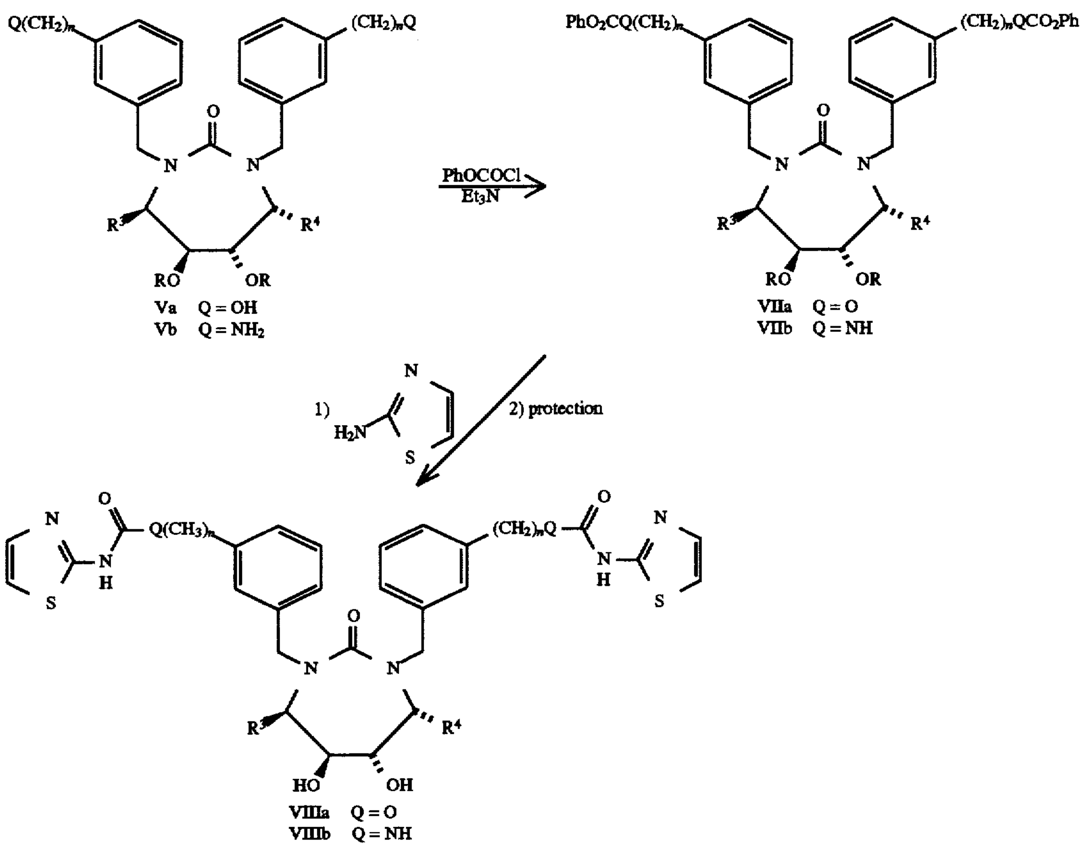

Va Q = OH
Vb Q = $NH_2$
VIIa Q = O
VIIb Q = NH
VIIIa Q = O
VIIIb Q = NH

Compounds of formula I wherein Y is $-(CH_2)_nC(=NH)NH-$, are obtained from nitriles of formula (V) using the reaction sequence shown in Scheme 5. A suitably protected nitrile (Va) is converted by standard conditions via the imidate to the corresponding formamidine (5a) which is treated with sodium hydride and a 2-bromoheteroaryl to provide 5b after deprotection.

Scheme 5

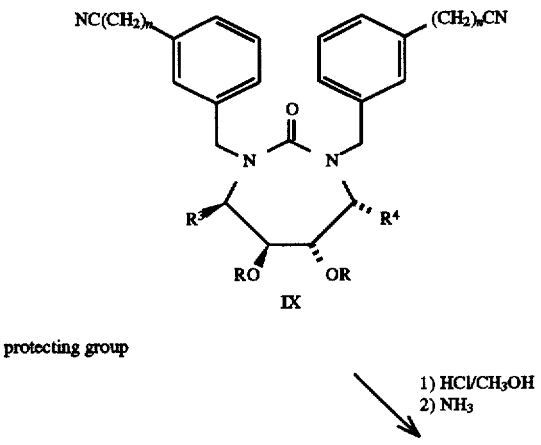

IX

R = protecting group

-continued
Scheme 5

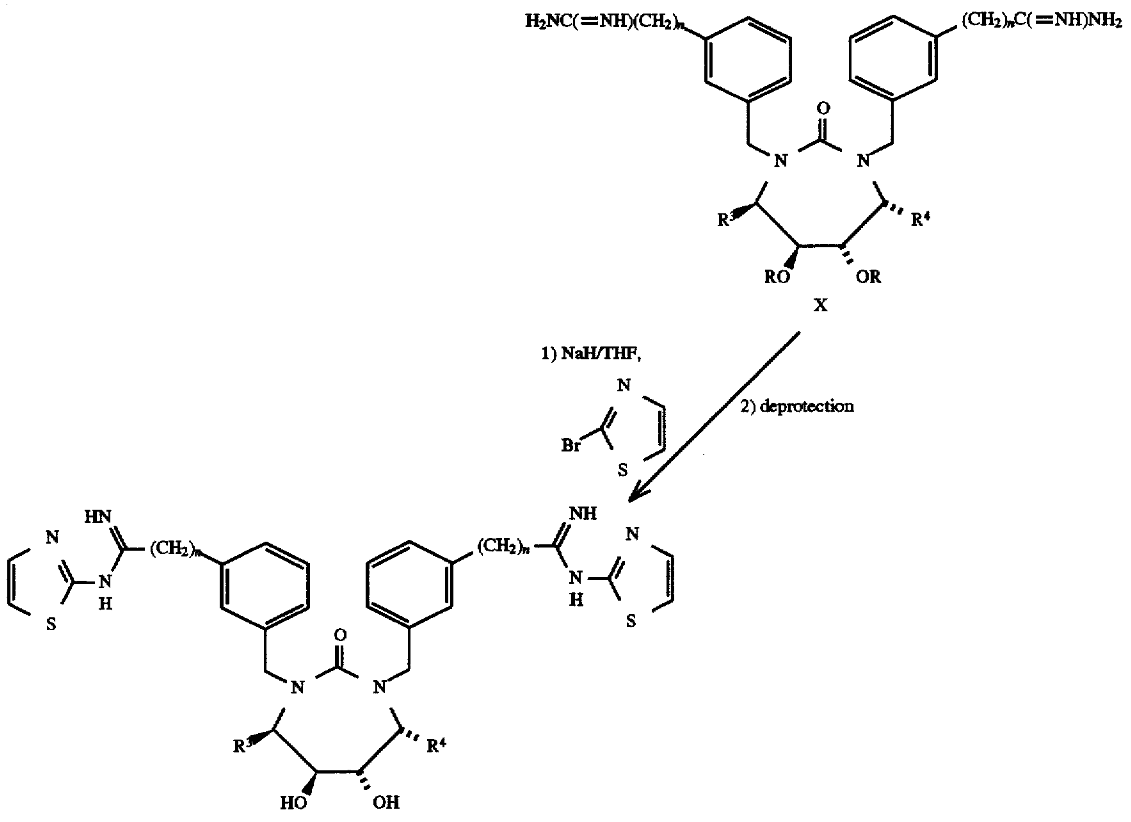

X

XI

The compounds of this invention and their preparation can be further understood by the following procedures and examples, which are intended to exemplify but not to limit the present invention.

EXAMPLE 1

A solution of diacid (IIIa, R=R=MEM) (1.08 g, 1.4 mmol) and 1-hydroxybenzotriazole (570 mg, 4.2 mmol) of in DMF (10 mL) was cooled in a 0° C. ice bath and 2-aminothiazole (421 mg, 4.2 mmol) was added. To the resulting solution was added a solution of 1,3-dicyclohexylcarbodiimide (1.15 g, 5.6 mmol) in DMF (6 mL). The reaction mixture was stirred at room temperature for 16 hours, diluted with ethyl acetate and filtered over celite. The solution was washed with water(2×), sat'd. sodium bicarbonate, and finally water again. The solution was the then dried over magnesium sulfate, filtered, and concentrated in vacuo. The residue was purified using flash chromatography (2:3 Hexane/EtOAc followed by 1:8 $MeOH:CHCl_3$) to elute 1.2 g of the bis MEM-protected amide as a white solid.

A solution of the bis MEM-protected intermediate (1.2 g) in methanol (6 mL) was treated with 4N HCl in dioxane (6 mL). The mixture was stirred at room temperature for 18 hours and then poured into 75 mL chloroform. The organic layer was washed with sat'd. sodium bicarbonate. The inorganic layer was extracted with chloroform (2×75 mL). The combined organic layers were dried over magnesium sulfate, filtered, and concentrated in vacuo. The residue was purified by flash chromatography using first chloroform, followed by 1% MeOH:CHCl3, 2%, and finally 4% to elute the diol 1 (880 mg, 82.0% yield from III) as a white solid. $^1H$ NMR (DMSO-$d_6$; ppm) δ12.655 (s, 1H, HNCO), 8.007 (2H, d, 8Hz), 7.956 (2H, S), 7.562–6.903 (m, 18H), 5.179 (s, 2H), 4.651 (s, 2H, 14 Hz), 3.564 (s, 2H), 3.070 (d, 2H, 14H), 2.977 (d, 2H, 12H), 2.506 (t, 2H, 12H); 13C NMR (DMSO-$d_6$; ppm), 164.857, 160.976, 158.743, 139.987, 138.990, 137.507, 133.122, 132.170, 129.159, 129.086, 128.582, 128.161, 126.935, 126.028, 113.772, 70.284, 66.549, 55.629, 32.187, FAB HRMS Calc: 759.242337; Found: 759.240694.

EXAMPLE 2

A solution of diacid (IIIb, R=R=acetonide) (5.0 g. 0.0079 m), 1-hydroxybenzotriazole hydrate (2.13 g. 0.0158 m), and N,N-dimethylformamide (20 mL) was stirred at room temperature. To this was added 2-amino-4-methylthiazole (2.7 g. 0.0236m), 1-(3-dimethylaminopropyl)-3-ethylcarbodiimide hydrochloride (6.04 g 0.0315 m), triethylamine (3.19 g. 0.0315 m) and N,N-dimethylformamide (40 mL) as rinse. The reaction mixture was allowed to stir at room temperature overnight. The reaction mixture was poured into a separatory funnel containing distilled water, then extracted three times with ethyl acetate. The ethyl acetate layer was washed with hydrochloric acid (0.2N), saturated sodium bicarbonate, water, and brine then dried over magnesium sulfate. The ethyl acetate solution was filtered and evaporated and the residue purified by flash chromatography to provide the acetonide protected amide (5 gm, 76.5% yield).

A solution of intermediate acetonide-protected product (5.00 g. 0.006 m), tetrahydrofuran (300 mL), and conc.

hydrochloric acid (5 mL) was stirred overnight at room temperature. The reaction mixture was poured into a separatory funnel containing saturated sodium bicarbonate and extracted with ethyl acetate. The ethyl acetate was washed with saturated sodium bicarbonate, water and brine, then dried over magnesium sulfate. The magnesium sulfate was filtered, the solution evaporated and the residue purified by flash chromatography using methanol/chloroform as the mobile phase to provide the desired diol 2 (2.34 g (51% yield) 1H NMR (DMSO-$d_6$; ppm) δ12.6 (s, 2H), 8.307–6.801 (m, 20H), 5.192 (s, 2H), 4.662 (d, 2H, 14 Hz), 3.399 (s, 2H), 3.084 (s, 2H, 14 Hz), 2.993 (d, 2H, 13 Hz), 2.750 (t, 2H, 13 Hz); 13C NMR (DMSO-D6; ppm) 164.827, 161.018, 158.216, 146.468, 140.049, 139.042, 133.164, 132.294, 129.226, 129.107, 128.631, 128.219, 126.901, 126.086, 108.075, 70.331, 66.632, 55.708, 32.221, 16.774; FAB HRMS Calc: 787.273638; Found: 787.274268.

EXAMPLE 60

A solution of compound IIIc (R=R=acetonide) (3.0 g, 4.3 mmol) and pyridine (1.29 g, 16.2 mmol) in benzene (30 mL) was cooled in a 0° C. ice bath. The mixture was treated dropwise with 2.0M oxalyl chloride in dichloromethane (32.4 mL, 16.2 mL). A precipitate forms immediately and after the addition was complete the mixture was stirred at room temperature for 18 hours. The solvents and excess oxalyl chloride were removed in vacuo to afford acid chloride IV. This acid chloride intermediate was dissolved in pyridine (15 mL) and treated with 2-aminoimidazole sulfate (1.704g (, 12.9 mmol) and the mixture stirred at room temperature for 18 hours. This mixture was diluted with ethyl acetate and washed twice with water. The residue after removal of solvent was dissolved in a mixture of methanol (10 mL) and 4M HCl in dioxane (10 mL) was added to the above solution and the contents stirred at room temperature for 18 hours. The mixture was diluted with ethyl acetate and washed with sat. sodium bicarbonate. The residue after removal of solvent was purified by flash chromatography (100 g silica gel) using 1:1 EtOAc:Hexane followed by 10:1:10 EtOAc:EtOH:Hexane to elute 1.145 g (50.4% recovery) white solid which was identified as methyl ester of IIIc (R=R=H). The second component of the mixture was eluted with 1% MeOH in CHCl3 followed by 2% and finally 5% to afford 711 mg (28.5% yield) of desired deprotected amide 39 (Ex. 39) as off-white solid. $^1$H NMR ($CDCl_3$; ppm) δ7.858–6.765 (m, 17H), 4.772 (d, 1H, 14.3 Hz), 3.713 (s, 2H) 4.605 (m, 2H) 3.126 (m, 5H); 13C NMR ($CDCl_3$; ppm); 167.359, 161.993, 142.480, 139.394, 138.607, 133.745, 132.985, 129.166, 128.672, 128.352, 126.731, 126.264, 117.629, 117.602, 117.492, 117.446, 70.500, 66.260, 55.959, 32.417; FAB HRMS Calc: 580.292380, Found: 580.291255.

EXAMPLES 500, 501 and 502

Compounds of formula I wherein X is thiophene, are obtained as illustrated in Schemes 6 and 7 and in the following experimental procedures.

Scheme 6

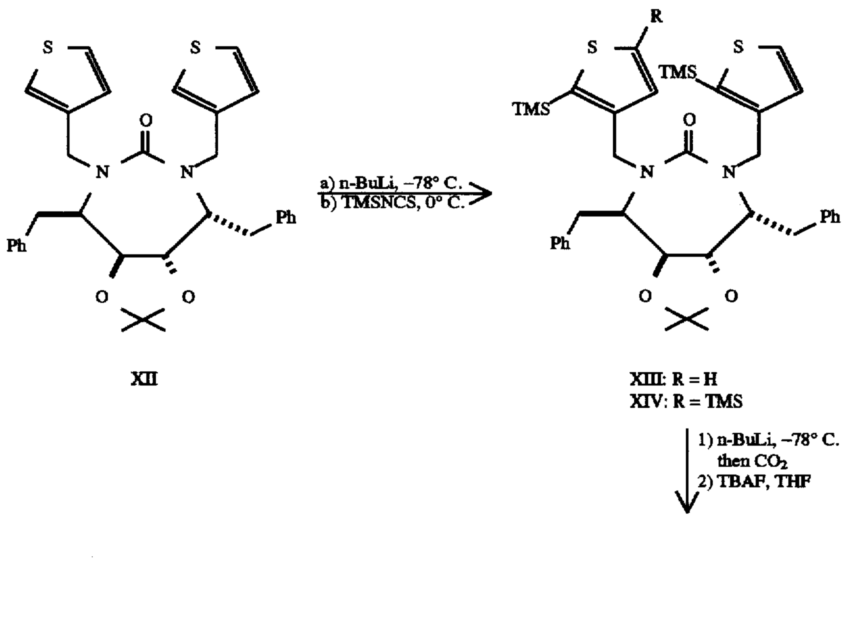

XII

XIII: R = H
XIV: R = TMS

-continued

Scheme 6

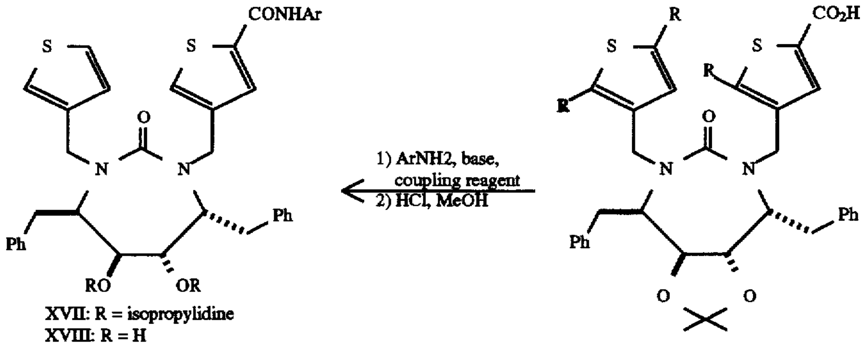

XVII: R = isopropylidine
XVIII: R = H

XV: R = TMS
XVI: R = H

Scheme 7

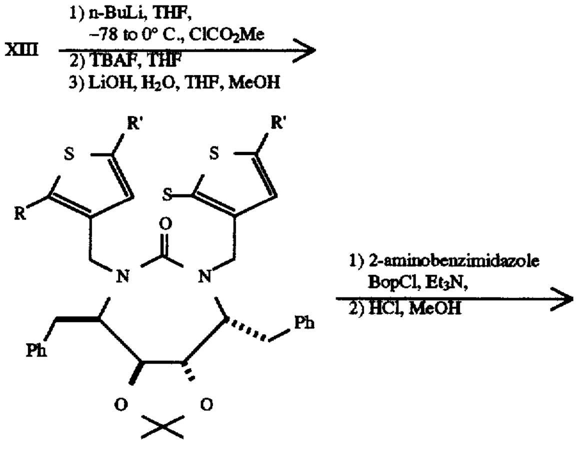

XIX: R = TMS, R' = Me
XX: R = H, R' = Me
XXI: R = R' = H

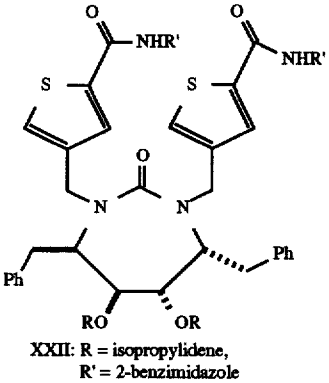

XXII: R = isopropylidene,
R' = 2-benzimidazole
XXIII: R = H,
R' = 2-benzimidazole

EXAMPLE 500

Trisilylated thiophene XIV and disilylated thiophene XIII

To a stirred, cooled (−78° C.) solution of 1.60 g(2.86 mmol) of thiophene I in 10 mL of THF was added 2.6 mL(6.5 mmol) of a 2.5M solution of n-BuLi in hexanes. The solution was stirred 15 min. warming to 0° C. and then re-cooled to −78° C. The solution was treated with 1.27 mL(9.0 mmol) of trimethylsilylisothiocyanate, and stirring was continued for 30 min while the solution warmed to 0° C. The mixture was poured into 1N HCl and extracted with ether. The organic extract was dried ($MgSO_4$), concentrated under reduced pressure, and chromatographed on silica gel. Gradient elution with ether-hexanes afforded, after evaporation of solvents, 1.70 g(84%) of XIII and 0.22 g(10%) of XIV. $^1H$ NMR(300 MHz, $CDCl_3$) δXIII: 7.44(d, 1H); 7.20–7.33(m, 4H); 7.12(d, 2H); 5.16(d, 1H); 4.08(br. s, 1H); 3.80–3.86(m, 1H); 3.45(d, 1H); 2.97–3.10(m, 2H); 1.40(s, 3H); 0.16(s, 9H). III:7.45(d, 1H); 7.38(s, 1H); 7.20–7.33 (m, 7H); 7.11 (d, 4H); 5.19 (d, 1H); 5.11 (d, 1H); 4.07–4.11(m, 2H); 4.78–4.88(m, 2H); 3.46(d, 1H); 3.41(d, 1h); 2.98–3.12 (m, 4H); 1.40(s, 3H); 1.48(s, 3H); 0.19(s, 9H); 0.18(s, 9H); 0.17(s, 9H).

Thiophene acid XVI

To a stirred, cooled(−78° C.) solution of 0.21 g(0.27 mmol) of thiophene XIV in 4 mL of THF was added 0.21 mL(0.52 mmol) of n-BuLi in hexanes. The solution was stirred 15 min. warming to ambient temperature, re-cooled to −78° C., and quenched with a large excess of dry ice. The solution was warmed to 0° C. with stirring over 10 min and poured into water. The mixture was extracted with EtOAc, and the organic extract was dried($MgSO_4$) and concentrated under reduced pressure to afford an oil. The crude acid was dissolved in 5 mL of THF and treated with 2 mL of 1M tetra-(n-butylammonium fluoride) (TBAF) in THF. The solution was stirred 16 h and poured into water. The mixture was extracted with EtOAc, and the organic extract was washed with brine, dried($MgSO_4$), and concentrated under reduced pressure to give an oil. Chromatography on silica gel(elution with 1:1 EtOAc-hexanes) afforded, after removal of solvent and lyophilizatrion from benzene, 93 mg(59%) of acid XVI as a powder. Mass spectrum($NH_3$-DCI): 603((M+H)$^+$, 20%), 620((M+NH4)$^+$, 100%).

Carboxamide XVIIIa (Example 500)

To a stirred solution of 10 mg(0.1 mmol) of 2-aminopyridine, 30 mg (0.05 mmol) of acid V, and 10 mg(0.1 mmol) of 4-dimethylaminopyridine in 2 mL of $CH_2Cl_2$ was added 28 mL (0.2 mmol) of triethylamine followed by 25 mg (0.1 mmol) of bis(2-oxo-3-oxazolidinyl) phosphinic chloride (Bop-Cl). The suspension was stirred 16 h and poured into a mixture of brine and 0.1M aq. HCl. The mixture was extracted with ether, and the organic extract was washed with aq. $NaHCO_3$ then brine. The solution was dried ($MgSO_4$) and concentrated to afford an oil. The crude amide was dissolved in 6 mL of MeOH and treated with 0.1 mL of con. aq. HCl. The solution was stirred 1 h at ambient temperature and then poured into aq. $NaHCO_3$. The mixture was extracted with EtOAc, and the organic extract was washed with brine, dried($MgSO_4$), and concentrated under reduced pressure. Lyophilization from benzene afforded 30 mg(90%) of SF651 as a white powder. Mass spectrum($NH_3$-DCI): 639($(M+H)^+$, 100%), 656($(M+NH_4)^+$, 40%).

Carboxamide XVIIIb (Example 501)

To a stirred suspension of 26 mg(0.2 mmol) of 2-aminoimidazole sulfate, 52 mL(0.3 mmol) of diisopropylethylamine, and 50 mg(0.083 mmol) of acid XVI in 2 mL of DMF was added 88 mg(0.2 mmol) of BOP. The solution was stirred 16 h and poured into water. The mixture was extracted with EtOAc, and the extract was dried ($MgSO_4$) and concentrated under reduced pressure. The crude product was dissolved in 2 mL of methanol and treated with 0.1 mL of con. aq. HCl. The solution was stirred 16 h, poured into water, and extracted with ethyl acetate. The organic extract was dried($MgSO_4$) and concentrated under reduced pressure to afford a glass. The crude product was chromatographed on silica gel(gradient elution with 2 to 5% methanol in dichloromethane) to afford, after removal of solvent and lyophilization, 7 mg(13%) of carboxamide SF653 as a white powder. Mass spectrum($NH_3$-DCI): 628( $(M+H)^+$, 100%).

EXAMPLE 502

Diester XIX

To a stirred, cooled(−78° C.) solution of 1.41 g(2.0 mmol) of thiophene IIa in 10 mL of THF was added 1.6 mL(4.0 mmol) of 2.5M n-BuLi in hexanes. The solution was stirred 10 min., warming to 0° C., then re-cooled to −78° C. The solution was treated with 0.39 mL(5 mmol) of methyl chloroformate, warmed to ambient temperature, and poured into 0.5N aq. HCl. The mixture was extracted with ether, and the organic extract was washed with brine, dried($MgSO_4$), and concentrated under reduced pressure. The crude diester was chromatographed on silica gel(elution with 3:1 hexanes-ether) to afford, after removal of solvent, 0.95 g(58%) of diester XIX. $^1H$ NMR($CDCl_3$, 300 MHz) δ7.87(s, 1H); 7.08–7.30(m, 5H); 4.15(ABq, 2H, $J_{AB}$=15 Hz, dn=480 Hz); 4.19(br. s, 1H); 3.85(m, 1H); 3.75(s, 3H); 2.90–3.12(m, 2H); 1.45(s, 3H); 0.20(s, 9H).

Thiophene XX

To a stirred solution of 0.95 g(1.16 mmol) of silane XIX in 10 mL of THF was added 4 mL(4 mmol) of 1M TBAF in THF. The solution was stirred 2 h and poured into water. The mixture was extracted with 1:1 ether-ethyl acetate, and the organic extract was washed(brine), dried($MgSO_4$), and concentrated under reduced pressure. The crude product was chromatographed on silica gel(elution with 3:1 ether-hexanes) to afford, after removal of solvent, 0.54 g(69%) of thiophene XX. Mass spectrum($NH_3$-DCI): 692($(M+H)^+$, 100%).

Diacid XXI

To a stirred solution of 0.49 g(0.73 mmol) of diester XX in 15 mL of THF was added 0.3 g of $LiOH.H_2O$ in 15 mL of water. The mixture was treated with methanol (~5 mL) to give a single phase. The solution was stirred 16 h, brought to reflux for 5 min., then cooled. The solution was poured into ether and washed once with water and twice with dilute aq. $K_2CO_3$. The combined aqueous washings were acidified with con. aq. HCl, and the resulting mixture was extracted twice with EtOAc. The combined organic extracts were washed(brine), dried($MgSO_4$), and concentrated under reduced pressure to afford 0.39 g(83%) of diacid XXI as a white solid. $^1H$ NMR($CDCl_{3,\ 300}$ MHz) δ7.69(d, 1H, J=1.5 Hz); 7.30(d, 1H, J=1.5 Hz); 7.18–7.29(m, 3H); 7.00(d, 2H); 4.00(ABq, 2H, $J_{AB}$=15 Hz, dn=400 Hz); 3.97 (br. s, 1H); 3.81(m, 1H); 2.7–3.0(m, 2H); 1.42 (s, 3H).

Carboxamide XVIII (Example 502)

To a stirred solution of 40 mg(0.3 mmol) of 2-aminobenzimidazole, 65 mg (0.1 mmol) of diacid XXI 25 mg(0.25 mmol) of 4-dimethylaminopyridine and 0.5 mL of DMF in 2 mL of $CH_2Cl_2$ was added 83 mL (0.6 mmol) of triethylamine followed by 64 mg (0.25 mmol) of bis(2-oxo-3 -oxazolidinyl)phosphinic chloride (Bop-Cl). The suspension was stirred 68 h and poured into 0.1M aq. HCl. The mixture was extracted with EtOAc, and the organic extract was washed with aq. $NaNCO_3$, then water, then brine. The solution was dried ($MgSO_4$) and concentrated to afford an oil. The crude amide was dissolved in 6 mL of MeOH and treated with 0.1 mL of con. aq. HCl. The solution was stirred 1 h at ambient temperature and then poured into aq. $NaHCO_3$. The mixture was extracted with EtOAc, and the organic extract was washed with brine, dried($MgSO_4$), and concentrated under reduced pressure. The crude carboxamide was chromatographed on silica gel(gradient elution with dichloromethane and increasing amounts of methanol) to give a glass. Lyophilization from benzene afforded 49 mg(58%) of SF654 as a white powder. Mass spectrum($NH_3$-DCI): 419($(M+2H)^{++}$, 100%).

Using the above techniques and others known to one skilled in the art of organic chemistry, the compounds shown in the Tables below can also be prepared.

Utility

The compounds of this invention possess retroviral protease inhibitory activity, in particular, HIV inhibitory activity, as demonstrated, for example, by their activity in the assays described below. The compounds of formula (I) possess HIV protease inhibitory activity and are therefore useful as antiviral agents for the treatment of HIV infection and associated diseases.

The compounds of formula (I) possess HIV protease inhibitory activity and are effective as inhibitors of HIV growth. The protease inhibitory activity of the compounds of the present invention is demonstrated using standard assays of protease activity, for example, using the assay described below for assaying inhibitors of HIV protease activity. The ability of the compounds of the present invention to inhibit viral growth or infectivity is demonstrated in standard assay of viral growth or infectivity, for example, using the assays described below. The compounds of the present invention can be demonstrated to inhibit HIV-protease activity in vivo using the HIV-1 Protease Transgenic Mouse animal model described in PCT Application Publication Number WO 94/19329. The compounds of the present invention can also be demonstrated to exhibit in vivo HIV inhibitory activity using the HIV-1/CEM Mouse Xenotransplant animal model described in PCT Application Publication Number WO 94/19329. The HIV inhibitory activity of the presently claimed compounds in the tests described below provides evidence that the presently claims compounds are useful for the treatment of HIV infection in humans.

The compounds of the present invention also possess important non-therapeutic utilities for the detection and inhibition of HIV.

Since the compounds of the present invention inhibit HIV growth and infectivity, they may be used as HIV antivirals for the inhibition of HIV ex vivo in a biological sample which contains HIV or is suspected to contain HIV or to be exposed to HIV. Thus, the compounds of the present invention can be used to inhibit HIV present in body fluid samples, for example, a serum or semen sample which contains, or is suspected of containing, HIV. The samples can be treated, for example, in a method similar to those described below for the HIV RNA Assay or the HIV Yield Reduction Cell Assay.

In addition, the compounds of the present invention can be utilized as standard or reference compounds for use in procedures for the screening for agents which inhibit viral replication and/or HIV protease. Thus, the compounds according to the present invention can be used as positive controls of inhibitory activity in such assays and as a quality control standard. The assays can be performed, for example, as described below under the HIV Protease Inhibition Assay, the HIV RNA Assay, or the HIV Yield Reduction Cell Assay. The compounds of the present invention can be provided in a commercial kit or container comprising a compound of this invention, for use as such standard or reference compounds in pharmaceutical research.

In addition, since the compounds of the present invention exhibit selectivity for HIV protease, the compounds of the present claims can also be used as diagnostic reagents in diagnostic assays for the detection of HIV protease. Thus, inhibition of the protease activity in an assay (such as the assays described herein) by a compound of the present invention is indicative of the presence of HIV protease and, consequently, HIV virus. Alternatively, as will be readily appreciated by one of skill in the art, in view of the high affinity and specificity for HIV protease of the compounds of the present invention, such compounds could also be used in diagnostic assays based on measurement of the binding of such compounds to HIV protease.

As used herein "μg" denotes microgram, "mg" denotes milligram, "g" denotes gram, "μL" denotes microliter, "mL" denotes milliliter, "L" denotes liter, "nM" denotes nanomolar, "pM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 1 mM for the inhibition of HIV protease or HIV viral growth or infectivity. Preferred compounds of the present invention inhibit HIV protease with a $K_i$ value of ≦1 nM and inhibit virus with an $IC_{90}$ value of ≦0.05 μg/mL.

HIV Protease Inhibition Assay

Materials

Protease: Inclusion bodies of *E. coli* harboring plasmid containing plasmid T1718R with a synthetic gene coding for a single-chain tethered dimer of HIV protease were prepared as described in Cheng et al. (Proc. Natl. Acad. Sci. USA, 87, 9660–9664, 1990). Active protease was prepared as described therein by extraction with 67% acetic acid, dilution 33-fold with water, dialysis against water and then against a refolding buffer consisting of 20 mM MES, 1 mM dithiothreitol and 10% glycerol. Protease was stored as a stock preparation at 10 μM in refolding buffer.

Substrate: Peptide of sequence: aminobenzoyl-Ala-Thr-His-Gln-Val-Tyr-phe($NO_2$)-Val-Arg-Lys-Ala containing p-nitrophenylalanine, was prepared by solid phase synthesis as previously described Cheng et al. (Proc. Natl. Acad. Sci. USA, 87, 9660–9664, 1990). Stock solutions of 2 mM substrate were prepared in DMSO.

Inhibitory compounds were dissolved in sufficient DMSO to make 3 mM stock solutions. All further dilutions were prepared in "assay buffer": 1M NaCl, 50 mM MES, pH 5.5, 1 mM EDTA, 1 mM DTT, 20% glycerol.

Reactions

Enzyme reaction: In a 2 mL screw-cap centrifuge tube were added 50 μl protease (final concentration 0.25 nM) and 0.1 mL inhibitory compound (final concentration 0.1–12, 500). After 15 min preincubation at room temperature, the reaction was started with the addition of 0.05 mL substrate (final concentration 5 μM). Incubation was carried out at 30 C. for 1 hr. The reaction was stopped with 1 mL 0.1M ammonium hydroxide.

HPLC measurement of product formation: The product (aminobenzoyl-Ala-Thr-His-Gln-Val-TYr) was separated from substrate on a Pharmacia MonoQ anion exchange column. The injection volume was 0.2 mL. The mobile phases were A (20 mM trisHCl, pH 9.0, 0.02% sodium azide, 10% acetonitrile) and B (20 mM tris HCl, pH 9.0, 0.02% sodium azide, 0.5M ammonium formate, 10% acetonitrile). The mobile phases were pumped at 1 mL/min, with a gradient from 0 to 30% B in 5 min, 100% B for 4 min to wash the column, and a re-equilibration for 4 min. The retention time of the product was 3.6 min. Detection with a Shimadzu model RF535 fluorescence monitor was at 330 nm (excitation) and 430 (emission). The Ki was calculated from the formula:

Ki=I/(((Km+S−FA*S)/(FA*Km))−1); where I=inhibitory concentration, S=substrate concentration, FA=fractional activity=cm peak height with inhibitor/cm peak height without inhibitor, and Km=Michaelis constant=20 μM.

HIV RNA Assay

DNA Plasmids and in vitro RNA transcripts

Plasmid pDAB 72 containing both gag and pol sequences of $BH_{10}$ (bp 113–1816) cloned into PTZ 19R was prepared according to Erickson-Viitanen et al., AIDS Research and Human Retroviruses (1989) 5:577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored a −70° C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, Tet. Lett. (1989) 30:6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCTTCT 3') was complementary to nucleotides 950–973 of HXB2. All nucleotide positions are those of the GenBank Genetic Sequence Data Bank as accessed through the Genetics Computer Group Sequence Analysis Software Package (Devereau, Nucleic Acids Research (1984) 12:387). The reporter probes were prepared as 0.5 μM stocks in 2× SSC (0.3M NaCl, 0.03M sodium citrate), 0.05M Tris pH 8.8, 1 mg/mL BSA. The biotinylated capture probes were prepared as 100 μM stocks in water.

Streptavidin coated plates

Nunc-immunomodule microtiter plate strips were coated by addition of 200 μL of streptavidin (30 μg/mL, Scripps, La Jolla, Calif.) in freshly prepared 10 mM sodium carbonate (pH 9.6). Plates were incubated overnight at 4° C. Streptavidin solution was aspirated from the wells and a blocking buffer composed of phosphate buffered saline (PBS), 20 mg/mL bovine serum albumin (crystalline, nuclease and protease free, Calbiochem) and 100 mg/mL lactose (Sigma) was added to the plates for 3 hrs at room temperature. Blocking buffer was removed from the wells, which were allowed to dry overnight at room temperature and subsequently stored at 4° C. in zip lock bags with desiccant. For the majority of the compound evaluation experiments, streptavidin coated plates were obtained from DuPont Biotechnology Systems (Boston, Mass.).

Cells and virus stocks

MT-2, CEM, and $H_9$ cells were maintained in RPMI 1640 supplemented with 5% fetal calf serum (FCS), 2 mM L-glutamine and 50 μg/mL gentamycin, all from Gibco. Laboratory strains of HIV-1 (RF, MN and IIIB) were propagated in $H_9$ cells in the same medium. Virus stocks were prepared approximately 1 month after acute infection of $H_9$ cells by clarification of the tissue culture medium and storage of aliquots at −70° C. Infectious titers of HIV-1(RF) stocks were 1–3×$10^7$ PFU (plaque forming units)/mL as measured by plaque assay on MT-2 cells (see below). Each aliquot of virus stock used for infection was thawed only once. In some cases, infected $H_9$ cells were shifted to Dulbecco's modified Eagle's medium 3–10 days before collection of virus in order to generate virus stocks in medium with low biotin content. Clinical isolates of HIV that had been passaged once in MT-2 cells were used to infect fresh MT-2 cells in RPMI medium. Three days after infection, cells were pelleted, resuspended and culture continued in Dulbecco's modified Eagle's medium as above. Virus stocks of clinical isolates were prepared 10–15 days after infection when cytopathic effects were apparent in the culture.

For evaluation of antiviral efficacy, cells to be infected were subcultured one day prior to infection. On the day of infection, cells were resuspended at 5×$10^5$ cells/mL in RPMI 1640, 5% FCS for bulk infections or at 2×$10^6$/mL in either Dulbecco's modified Eagles medium, or RPMI 1640 medium minus biotin (Gibco, custom formulation) with 5% FCS for infection in microtiter plates. Virus was added and culture continued for 3 days at 37° C. In some experiments, virus was removed after an initial adsorption period.

Preparation of HIV-1 infected cell lysates

HIV-1 infected cells were pelleted by centrifugation. After removal of the supernatant the cells were resuspended at a concentration of 1×$10^7$ cells/mL in 5M guanidinium isothiocyanate solution (GED: 5M guanidinium isothiocyanate (Sigma), 0.1M EDTA, 10% dextran sulfate). Alternately, cells grown in biotin free tissue culture medium were mixed with 5M GED to a final concentration of 3M guanidinium isothiocyanate, 0.06M EDTA and 6% dextran sulfate.

HIV RNA assay

Cell lysates or purified RNA in 3M or 5M GED were mixed with 5M GED and capture probe to a final guanidinium isothiocyanate concentration of 3M and a final biotin oligonucleotide concentration of 30 nM. Hybridization was carried out in sealed microfuge tubes or in sealed U bottom 96 well tissue culture plates (Nunc or Costar) for 16–20 hours at 37° C. RNA hybridization reactions were diluted three-fold with deionized water to a final guanidinium isothiocyanate concentration of 1M and aliquots (150 μL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 μl of a hybridization cocktail containing 4× SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 μL of 0.2 mM 4-methylumbelliferyl phosphate (MUBP, JBL Scientific) in buffer δ(2.5M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate based compound evaluation in HIV-1 infected MT-2 cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 μL) were added to a final concentration of 5×$10^5$ per mL (1×$10^5$ per well). Cells were incubated with compounds for 30 minutes at 37° C. in a $CO_2$ incubator. For evaluation of antiviral potency, an appropriate dilution of HIV-1 (RF) virus stock (50 μL) was added to culture wells containing cells and dilutions of the test compounds. The final volume in each well was 200 μL. Eight wells per plate were left uninfected with 50 μn of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5M GED containing biotinylated capture probe was added to the settled cells and remaining medium in each well to a final concentration of 3M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×$10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective protease inhibitor should be less than 10% of the level achieved in an uninhibited infection.

For antiviral potency tests, all manipulations in microtiter plates, following the initial addition of 2× concentrated compound solution to a single row of wells, were performed using a Perkin Elmer/Cetus ProPette.

HIV Yield Reduction Cell Assay

Materials: MT-2, a human T-cell line, was cultured in RPMI medium supplemented with 5% (v/v) heat inactivated fetal calf serum (FCS), L-glutamine and gentamycin. Human immunodeficiency virus strains, HIV (3B) and HIV (RF) were propagated in H-9 cells in RPMI with 5% FCS. Poly-L-lysine (Sigma) coated cell culture plates were prepared according to the method of Harada et al., Science (1985) 229:563–566. MTT, 3-(4,5-dimethyl-thiazol-2yl)-2,5-diphenyltetrazolium bromide, was obtained from Sigma.

Method: Test compounds were dissolved in dimethylsulfoxide to 5 mg/mL and serially diluted into RPMI medium to ten times the desired final concentration. MT-2 cells ($5\times10^5$/mL) in 2.3 mL were mixed with 0.3 mL of the appropriate test compound solution and allowed to sit for 30 minutes at room temperature. HIV (3B) or HIV (RF) (~$5\times10^5$ plaque forming units/mL) in 0.375 mL was added to the cell and compound mixtures and incubated for one hour at 36° C. The mixtures were centrifuged at 1000 rpm for 10 minutes and the supernatants containing unattached virus were discarded. The cell pellets were suspended in fresh RPMI containing the appropriate concentrations of test compound and placed in a 36° C., 4% $CO_2$ incubator. Virus was allowed to replicate for 3 days. Cultures were centrifuged for 10 minutes at 1000 rpm and the supernatants containing cell free progeny virus were removed for plaque assay.

The virus titers of the progeny virus produced in the presence or absence of test compounds were determined by plaque assay. Progeny virus suspensions were serially diluted in RPMI and 1.0 mL of each dilution was added to 9 mL of MT-2 cells in RPMI. Cells and virus were incubated for 3 hours at 36° C. to allow for efficient attachment of the virus to cells. Each virus and cell mixture was aliquoted equally to two wells of a six well poly-L-lysine coated culture plate and incubated overnight at 36° C., 4% $CO_2$. Liquid and unattached cells were removed prior to the addition of 1.5 mL of RPMI with 0.75% (w/v) Seaplaque agarose (FMC Corp.) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/mL was added. The plates were incubated overnight at 36° C. Clear plaques on a purple background were counted and the number of plaque forming units of virus was calculated for each sample. The antiviral activity of test compounds was determined by the percent reduction in the virus titer with respect to virus grown in the absence of any inhibitors.

The tested compounds of the present invention exhibit HIV protease and HIV virus inhibitory activity in the assays described above.

TABLE 1

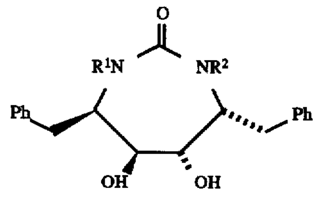

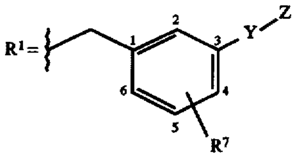

| Ex. No. | $R^2$ | Y | Z | $R^7$ | MS | MP |
|---|---|---|---|---|---|---|
| 1 | $R^1$ | —CONH— | 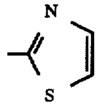 | H | 759 | |
| 2 | $R^1$ | —CONH— | 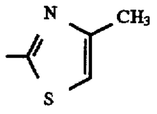 | H | 787 | |
| 3 | $R^1$ | —CONH— | 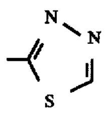 | H | 761 | |

TABLE 1-continued
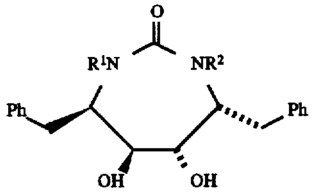
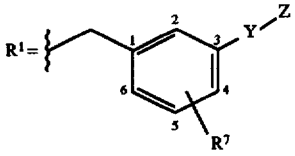
| Ex. No. | $R^2$ | Y | Z | $R^7$ | MS | MP |
|---|---|---|---|---|---|---|
| 4 | $R^1$ | —CONH— | 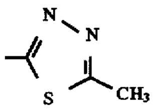 | H | 789 | |
| 5 | $R^1$ | —CONH— | 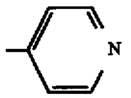 | H | 747 | 153–154 |
| 6 | $R^1$ | —CONH— | 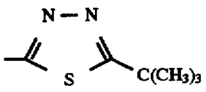 | H | | |
| 7 | $R^1$ | —CONH— | 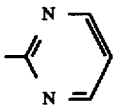 | H | 749 | 149–151 |
| 8 | $R^1$ | —CONH— | 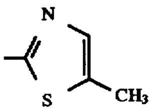 | H | 787.3 | |
| 9 | $R^1$ | —CONH— | 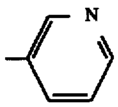 | H | 747 | 163–165 |
| 10 | $R^1$ | —CONH— | 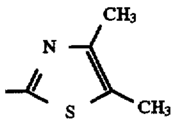 | H | 815 | 815 |
| 11 | $R^1$ | —CONH— | 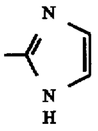 | H | 724 | 724 |
| 12 | $R^1$ | —CONH— | 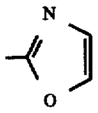 | H | | |

TABLE 1-continued
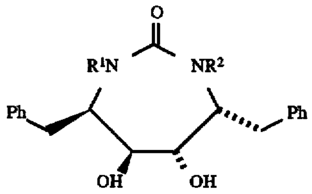
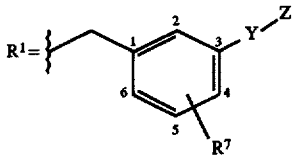
| Ex. No. | $R^2$ | Y | Z | $R^7$ | MS | MP |
|---|---|---|---|---|---|---|
| 13 | $R^1$ | —CONH— | 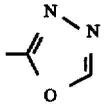 | H | | |
| 14 | $R^1$ | —CONH— | 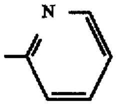 | H | 747 | 131–133 |
| 15 | $R^1$ | —CONH— | 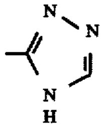 | H | | |
| 16 | $R^1$ | —CONH— | 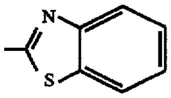 | H | 858 | |
| 17 | $R^1$ | —CONH— | 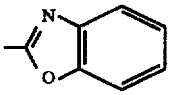 | H | | |
| 18 | $R^1$ | —CONH— | 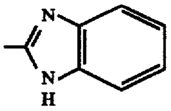 | H | 824 | |
| 19 | $R^1$ | —CONH— | 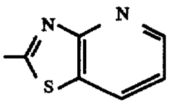 | H | | |
| 20 | $R^1$ | —CONH— | 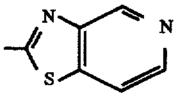 | H | | |
| 21 | $R^1$ | —CONH— | 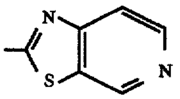 | H | | |
| 22 | $R^1$ | —CONH— | 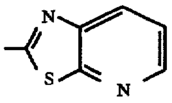 | H | | |

TABLE 1-continued
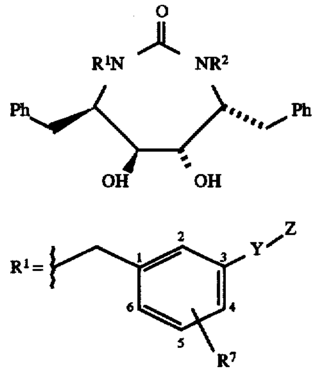
| Ex. No. | $R^2$ | Y | Z | $R^7$ | MS | MP |
|---|---|---|---|---|---|---|
| 23 | $R^1$ | −CONH− | 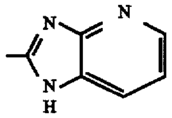 | H | | |
| 24 | $R^1$ | −CONH− | 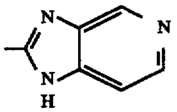 | H | | |
| 25 | $R^1$ | −CONH− | 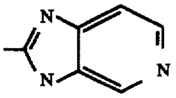 | H | | |
| 26 | $R^1$ | −CONH− | 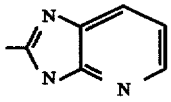 | H | | |
| 27 | $R^1$ | −CONH− | 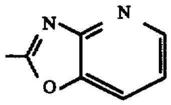 | H | | |
| 28 | $R^1$ | −CONH− | 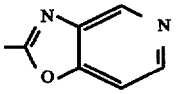 | H | | |
| 29 | $R^1$ | −CONH− | 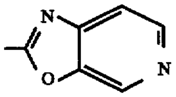 | | | |
| 30 | $R^1$ | −CONH− | 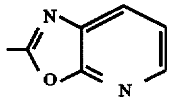 | H | | |
| 31 | $R^1$ | −CONH− | 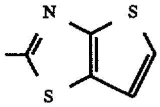 | H | | |
| 32 | $R^1$ | −CONH− | 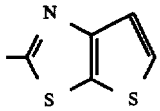 | H | | |

TABLE 1-continued
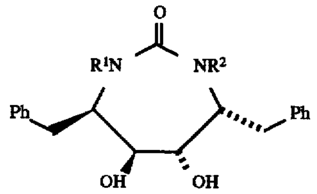
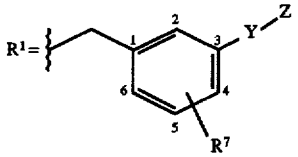
| Ex. No. | R² | Y | Z | R⁷ | MS | MP |
|---|---|---|---|---|---|---|
| 33 | R¹ | —CONH— | 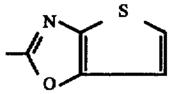 | H | | |
| 34 | R¹ | —CONH— | 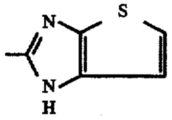 | H | | |
| 35 | R¹ | —CONH— | 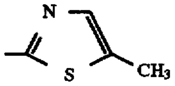 | 4-F | 823 | 137 |
| 36 | R¹ | —CONH— | 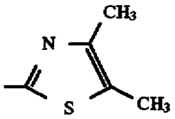 | 4-F | 851 | |
| 37 | R¹ | —CONH— | 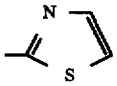 | 2-F | | |
| 38 | R¹ | —CONH— | 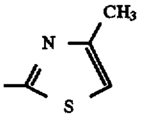 | 4-F | 823 | 181 |
| 39 | cyclopropylmethyl | —CONH— | 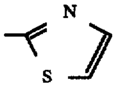 | H | 597.3 | |
| 40 | cyclopropylmethyl | —CONH— | 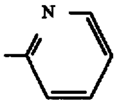 | H | 591 | |
| 41 | cyclopropylmethyl | —CONH— | 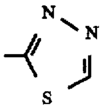 | H | 598 | |
| 42 | cyclopropylmethyl | —CONH— | 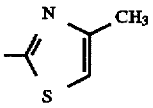 | H | 611 | |

TABLE 1-continued
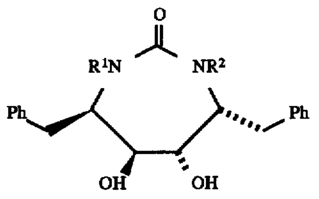
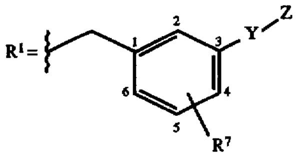
| Ex. No. | $R^2$ | Y | Z | $R^7$ | MS | MP |
|---|---|---|---|---|---|---|
| 43 | cyclopropylmethyl | —CONH— | 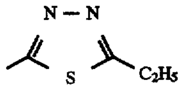 | H | 626 | |
| 44 | cyclopropylmethyl | —CONH— | 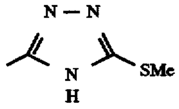 | H | 627 | |
| 45 | cyclopropylmethyl | —CONH— | 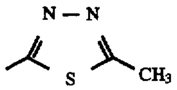 | H | 612 | |
| 46 | cyclopropylmethyl | —CONH— | 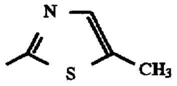 | H | 611 | |
| 47 | cyclopropylmethyl | —CONH— | 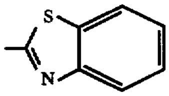 | H | 647 | |
| 48 | cyclopropylmethyl | —CONH— | 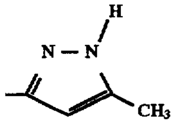 | H | 594 | |
| 49 | cyclopropylmethyl | —CONH— | 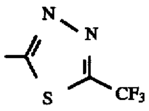 | H | 666 | |
| 50 | cyclopropylmethyl | —CONH— | 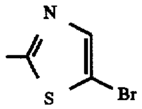 | H | 675 | |
| 51 | cyclopropylmethyl | —CONH— | 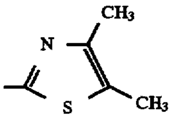 | H | 625 | |
| 52 | n-butyl | —CONH— | 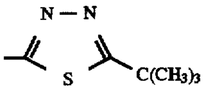 | H | 656.5 | 119.5 |

TABLE 1-continued
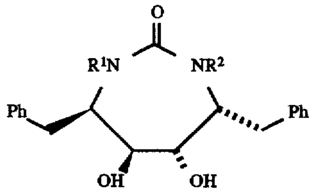
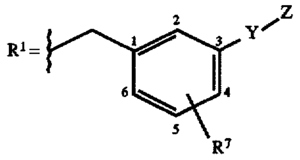
| Ex. No. | $R^2$ | Y | Z | $R^7$ | MS | MP |
|---|---|---|---|---|---|---|
| 53 | n-butyl | −CONH− | 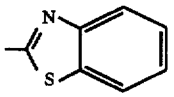 | H | 648 | |
| 54 | (4-fluorophenyl)-methyl) | −CONH− | 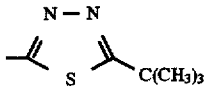 | H | 708 | 69–71 |
| 55 | 2-naphthylmethyl | −CONH− | 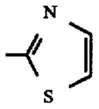 | H | 683.3 | 168–172 |
| 56 | n-butyl | −CONH− | 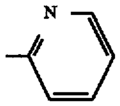 | H | 593.5 | 66.5 |
| 57 | (4-fluorophenyl)-methyl | −CONH− | 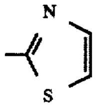 | H | 651.2 | 239 |
| 58 | (4-bromophenyl)-methyl | −CONH− | 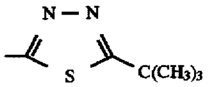 | H | 768 | 218–220 |
| 59 | 3-pyridylmethyl | −CONH− | 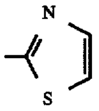 | H | | |
| 60 | cyclopropylmethyl | −CONH− | 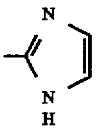 | H | 580.3 | |
| 61 | 3-carboxybenzyl | −CONH− | 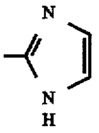 | H | 660.3 | |
| 62 | benzyl | −CONH− | 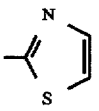 | H | 632 | |

TABLE 1-continued
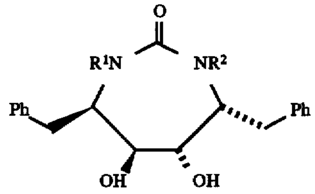
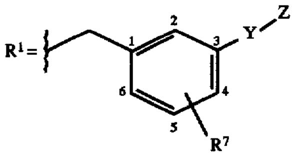
| Ex. No. | $R^2$ | Y | Z | $R^7$ | MS | MP |
|---|---|---|---|---|---|---|
| 63 | benzyl | —CONH— | 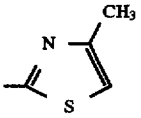 | H | 646 | |
| 64 | benzyl | —CONH— | 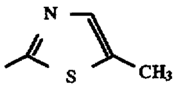 | H | 646 | |
| 65 | benzyl | —CONH— | 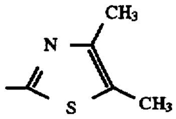 | H | 660 | |
| 66 | benzyl | —CONH— | 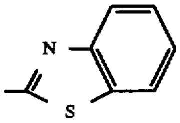 | H | 682 | |
| 67 | benzyl | —CONH— | 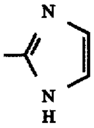 | H | 616.3 | |
| 68 | benzyl | —CONH— | 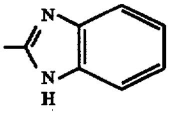 | H | 666.3 | |
| 69 | cyclopropylmethyl | —CONH— | 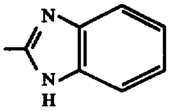 | H | 629 | |
| 70 | $R^1$ | —$CH_2NH$— | 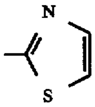 | H | 730 | |
| 71 | n-butyl | —CONH— | 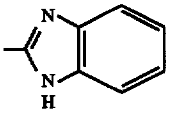 | H | 632 | 146 |

TABLE 1-continued
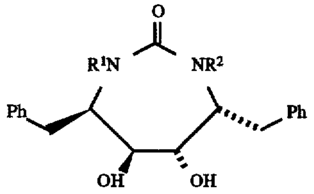
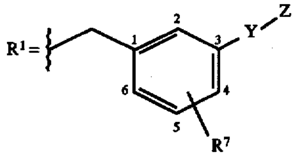
| Ex. No. | $R^2$ | Y | Z | $R^7$ | MS | MP |
|---|---|---|---|---|---|---|
| 72 | n-butyl | —CONH— | 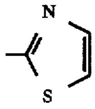 | H | 599.3 | |
| 73 | n-butyl | —CONH— | 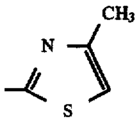 | H | 613.3 | |
| 74 | n-butyl | —CONH— | 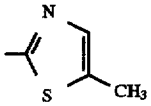 | H | 613.3 | |
| 75 | n-butyl | —CONH— | 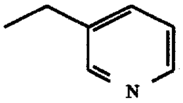 | H | | |
| 76 | n-butyl | —CONH— | 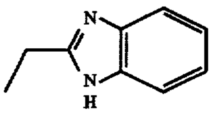 | H | | |
| 77 | $R^1$ | —CONH— | 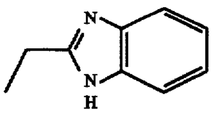 | H | | |
| 78 | 3-carboxybenzyl | —CONH— | 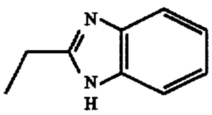 | H | | |
| 79 | n-$C_5H_{11}$ | —CONH— | 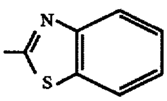 | H | 663 | 110 |
| 80 | n-$C_5H_{11}$ | —CONH— | 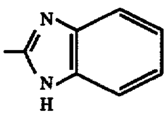 | H | 646.3 | 137–140 |
| 81 | 3-pyridylmethyl | —CONH— | 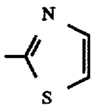 | H | | |

TABLE 1-continued
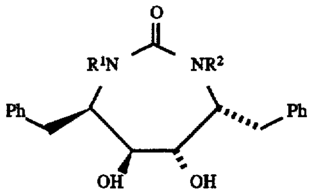
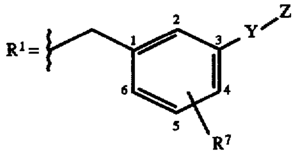
| Ex. No. | R² | Y | Z | R⁷ | MS | MP |
|---|---|---|---|---|---|---|
| 82 | 3-pyridylmethyl | —CONH— | 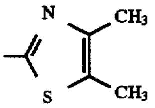 | H | | |
| 83 | 3-thienylmethyl | —CONH— | 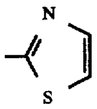 | H | | |
| 84 | 3-thienylmethyl | —CONH— | 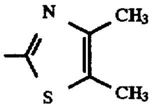 | H | | |
| 85 | $R^1$ | —CONH— | 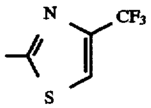 | H | | |
| 86 | 3-furanylmethyl | —CONH— | 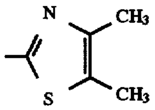 | H | 651 | amorphous |
| 87 | 3-furanylmethyl | —CONH— | 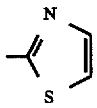 | H | 566 (M-56) | amorphous |
| 88 | 3-furanylmethyl | —CONH— | 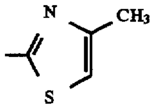 | H | 637 | amorphous |
| 89 | $R^1$ | —CONH— | 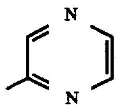 | H | 749 | 208 (d) |
| 90 | $R^1$ | —CONH— | 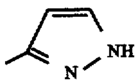 | H | 723 | 200 (d) |
| 91 | $R^1$ | —CONH— | 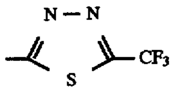 | H | 897 | 196.4 |

TABLE 1-continued
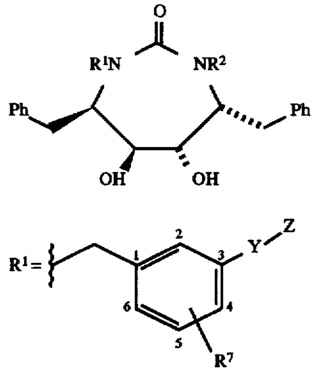
| Ex. No. | $R^2$ | Y | Z | $R^7$ | MS | MP |
| --- | --- | --- | --- | --- | --- | --- |
| 92 | $R^1$ | —CONH— | 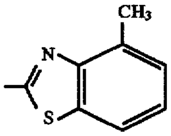 | H | 888 | 165 (d) |
| 93 | $R^1$ | —CONH— | 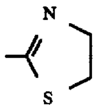 | H | 763 | 164.5 |
| 94 | (3-amino-5-indazolyl)methyl | —CONH— | 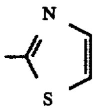 | H | | |
| 95 | (3-bromophenyl)methyl | —CONH— | 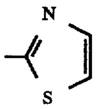 | H | 730 | 148–149 |
| 96 | (3-methoxyphenyl)methyl | —CONH— | 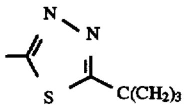 | H | 720.5 | 204–207 |
| 97 | (3-chlorophenyl)methyl | —CONH— | 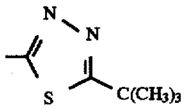 | H | 741 | 228–231 |
| 98 | (3-methoxyphenyl)methyl | —CONH— | 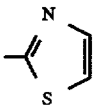 | H | 663.4 | 224–226 |
| 99 | (3,4-methylenedioxy-phenyl)methyl | —CONH— | 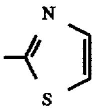 | H | | 215–216 |
| 100 | (3,4-methylenedioxy-phenyl)methyl | —CONH— | 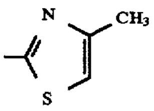 | H | | 265–266 |

TABLE 1-continued
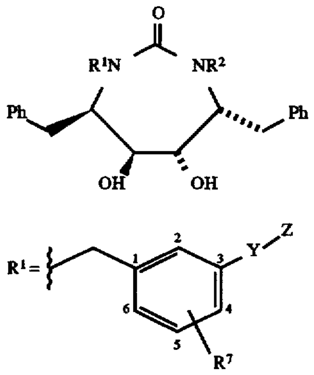
| Ex. No. | $R^2$ | Y | Z | $R^7$ | MS | MP |
|---|---|---|---|---|---|---|
| 101 | (3,4-methylenedioxy-phenyl)methyl | —CONH— | 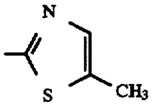 | H | | 247–248 |
| 102 | $R^1$ | —CONH— | 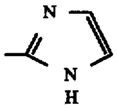 | H | 725.3 | |
| 103 | (3-carboxyphenyl)methyl | $-CH_2NH-$ | 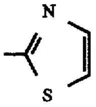 | H | | |
| 104 | $R^1$ | —NHCO— | 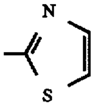 | H | | |
| 105 | $R^1$ | —NHCONH— | 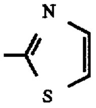 | H | | 207–208 |
| 106 | $R^1$ | —NHCO— | 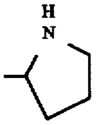 | H | | amorphous |
| 107 | $R^1$ | 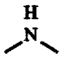 | 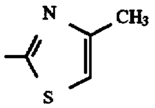 | H | 731.3 | 245–247 |
| 108 | cyclopropylmethyl | —CONH— | 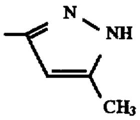 | H | 594.3 | |
| 109 | $R^1$ | $-CH_2S-$ | 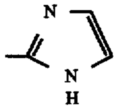 | H | | |

TABLE 1-continued
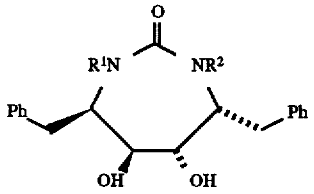
$R^1 =$ 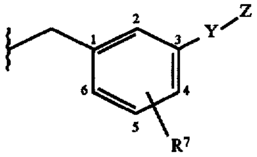
| Ex. No. | $R^2$ | Y | Z | $R^7$ | MS | MP |
|---|---|---|---|---|---|---|
| 110 | $R^1$ | $-CH_2O-$ | 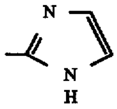 | H | | |
| 111 | $R^1$ | $-CH_2-$ | 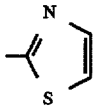 | H | | |
| 112 | $R^1$ | $-O-$ | 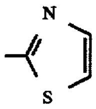 | H | | |
| 113 | $R^1$ | $-O-$ | 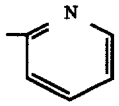 | H | | |
| 114 | $R^1$ | $-NHCONH-$ | 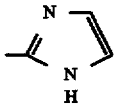 | H | | |
| 115 | $R^1$ | $-NHCONH-$ | 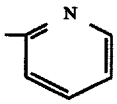 | H | | |
| 116 | $R^1$ | $-CONH-$ | 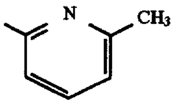 | H | 775 | 135–136 |
| 117 | $R^1$ | $-CONH-$ | 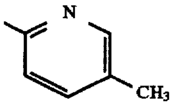 | H | 775 | 132–133 |
| 118 | $R^1$ | $-CONH-$ | 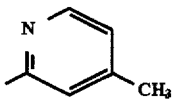 | H | 775 | 139–140 |
| 119 | $R^1$ | $-CONH-$ | 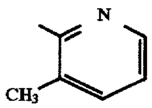 | H | 775 | 142–143 |

TABLE 1-continued

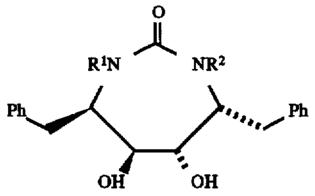

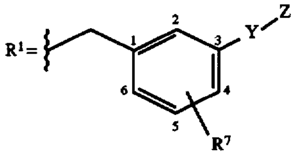

| Ex. No. | $R^2$ | Y | Z | $R^7$ | MS | MP |
|---|---|---|---|---|---|---|
| 120 | n-butyl | —CONH— | 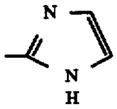 | H | 582.3 | |
| 121 | n-pentyl | —CONH— | 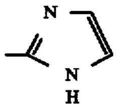 | H | 596.3 | 132–135 |
| 122 | 3-methylbutyl | —CONH— | 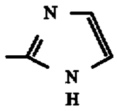 | H | | |
| 123 | 2-methylpropyl | —CONH— | 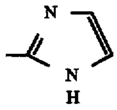 | H | | |

TABLE 2

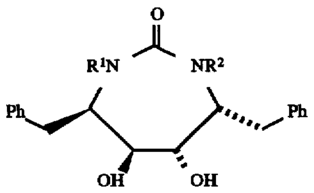

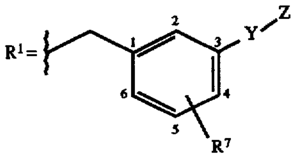

| Ex. No. | $R_2$ | Y | Z | $R_7$ | MS | MP |
|---|---|---|---|---|---|---|
| 230 | $R_1$ | —CONH— | 5-methyl-6H-1,3,4-thiadiazine | H | 817 | 150–153 |
| 231 | 3,3-dimethyl-allyl | —CONH— | 2-benzimidazole | H | 644 | |
| 232 | 2-methyl-allyl | —CONH— | 2-benzimidazole | H | 670 | 153–155 |
| 233 | 3-furanyl-methyl | —CONH— | 2-dihydrothiazole | H | 625 | amorphous |
| 234 | 3-furanyl-methyl | —CONH— | 5-methyl-2-thiazole | H | 637 | amorphous |
| 235 | 3-furanyl-methyl | —CONH— | 3-tetrahydrofuran | H | 610 | amorphous |

TABLE 2-continued

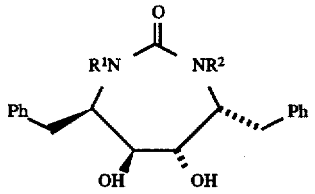

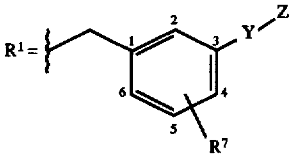

| Ex. No. | $R_2$ | Y | Z | $R_7$ | MS | MP |
|---|---|---|---|---|---|---|
| 236 | $R_1$ | —CONH— | 4,6-dimethyl-2-pyridine | H | 803 | 166–170 |
| 237 | $R_1$ | —CONH— | 5-chloro-2-pyridine | H | 816 | 261–265 |
| 238 | 3-amino-5-indazolyl-methyl | —CONH— | 5-methyl-2-thiazole | H | 702.3 | 179–181 |
| 239 | 5-indazolyl-methyl | —CONH— | 2-thiazole | H | 673.3 | 167–169 |
| 240 | 3-amino-5-indazolyl-methyl | —CONH— | 4-methyl-2-thiazole | H | 702.3 | 161–163 |
| 241 | 3-amino-5-indazolyl-methyl | —CONH— | 4,5-dimethyl-thiazole | H | 716.3 | 150–152 |
| 242 | 5-indazolyl-methyl | —CONH— | 6-methyl-2-pyridine | H | 681.3 | 147–149 |
| 243 | 3-methoxy-benzyl | —CONH— | 2-thiazole | H | 663.4 | 224–226 |
| 244 | $R_1$ | —CONH— | 3,4-methylenedioxy-phenyl | H | | |
| 245 | $R_1$ | —CONH— | 2-hydroxy-phenyl | H | 794 ($M + NH_4$) | |
| 246 | 3-azido-4-fluoro-benzyl | —CONH— | 2-benzimidazole | H | 725.6 | >200 (d) |
| 247 | 3-amino-4-fluoro-benzyl | —CONH— | 2-benzimidazole | H | 699.5 | 163–166 |
| 248 | $R_1$ | —CONH— | 2-benzimidazole | 4-F | 861.7 | 240–243 |
| 249 | 3-(2-thiazole)amino-carbonyl-benzyl | —CONH— | 2-imidazole | H | 742.3 | |
| 250 | $R_1$ | —CONH— | 1-methyl-2-benzimidazole | H | 853.4 | |
| 251 | 3-(2-hydroxy-isopropyl)benzyl | —CONH— | 2-pyridine | H | 702 ($M + NH_4$) | 215–216 |
| 252 | 3-(2-hydroxy-isopropyl)benzyl | —CONH— | 6-methyl-2-pyridine | H | | 217–219 |
| 253 | 3-(2-hydroxy-isopropyl)benzyl | —CONH— | 5-methyl-2-pyridine | H | | 185–186 |
| 254 | 3-(2-hydroxy-isopropyl)benzyl | —CONH— | 2-benzimidazole | H | | 140–141 |
| 255 | 3-(2-hydroxy-isopropyl)benzyl | —CONH— | 2-imidazole | H | | 75–77 |
| 256 | 3,4-ethylenedioxy-benzyl | —CONH— | 2-benzimidazole | H | 724.3 | 155–157 |
| 257 | 3,4-ethylenedioxy-benzyl | —CONH— | 2-imidazole | H | 624.3 | 147–149 |
| 258 | 3-trifluoramethyl-benzyl | —CONH— | 2-thiazole | H | 718 ($M + NH_4$) | |
| 259 | 2,4-difluoro-benzyl | —CONH— | 1-isoquinoline | H | 713 | 230–233 |
| 260 | $R_1$ | —CONH— | 1-isoquinoline | H | 847 | 202–203 |
| 261 | $R_1$ | —CONH— | 2-quinoline | H | 847 | 276–278 |
| 262 | 3-methoxy-benzyl | —CONH— | 2-guinoline | H | 707 | 229–231 |
| 263 | 3-furanyl-methyl | —CONH— | 2-pyridine | H | 617 | amorphous |
| 264 | 5-bromo-3-furanyl-methyl | —CONH— | 2-pyridine | H | 703 | amorphous |
| 265 | 3-furanyl-methyl | —CONH— | 2-benzimidazole | H | 656 | amorphous |
| 266 | 3-furanyl-methyl | —CONH— | 2-imidazole | H | 606 | amorphous |
| 267 | 3-thienyl-methyl | —CONH— | 2-benzimidazole | H | 672 | amorphous |
| 268 | 3-thienyl-methyl | —CONH— | 2-imidazole | H | 622 | amorphous |
| 269 | 5-bromo-3-furanyl methyl | —CONH— | 2-imidazole | H | 684 | amorphous |

TABLE 2-continued

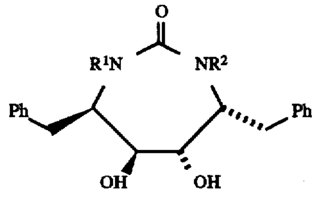

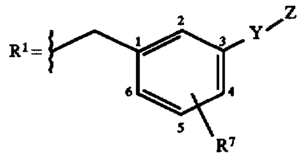

| Ex. No. | $R_2$ | Y | Z | $R_7$ | MS | MP |
|---|---|---|---|---|---|---|
| 270 | n-butyl | —CONH— | 5-methyl-2-pyridine | H | 607 | 103–106 |
| 271 | n-butyl | —CONH— | 6-methyl-2-pyridine | H | 607 | 97–100 |
| 272 | n-butyl | —CONH— | 5,6-dimethyl-2-benzimidazole | H | 660 | 159–163 |
| 273 | n-butyl | —CONH— | 4-methyl-2-pyridine | H | 607 | 92–95 |
| 274 | $R_1$ | —CONH— | 5,6-dimethyl-2-benzimidazole | H | 881.1 | 228–232 |
| 275 | 3-(2-imidazole)-aminocarbonyl-benzyl | —CONH— | 5,6-dimethyl-2-benzimidazole | H | 803.2 | 196–200 |
| 276 | 3-(2-imidazole)-aminocarbonyl-benzyl | —CONH— | 2-benzimidazole | H | 775.2 | 170–173 |
| 277 | 3-carboxy-benzyl | —CONH— | 5,6-dimethyl-2-benzimidazole | H | 738 | 211–215 |
| 278 | 3 carboxy-benzyl | —CONH— | 2-benzimidazole | H | 710 | 275–278 |
| 279 | 3-carbomethoxy-benzyl | —CONH— | 5,6-dimethyl-2-benzimidazole | H | 752 | 130–134 |
| 280 | 4,4,4-trifluoro-butyl | —CONH— | 2-benzimidazole | H | 686.3 | 147–151 |
| 281 | allyl | —CONH— | 2-benzimidazole | H | 616.4 | 131–135 |
| 282 | 3,3-dimethyl-allyl | —CONH— | 2-benzimidazole | H | 644.4 | 138–142 |
| 283 | 5-indazolyl-methyl | —CONH— | 2-benzimidazole | H | 706.4 | 190 |
| 284 | 4,4,4-trifluoro-butyl | —CONH— | 2-imidazole | H | 636.3 | 108 |
| 285 | 5-indazolyl-methyl | —CONH— | 5,6-dimethyl-2-benzimidazole | H | 734.4 | 198–201 |
| 286 | 5-indazolyl-methyl | —CONH— | 2-imidazole | H | 656 | 175–178 |
| 287 | 3-(2-pyridyl)methylaminocarbonyl-benzyl | —CONH— | 2-benzimidazole | H | 800.4 | 162.5 |
| 288 | 3-[2-(2-pyridyl)-ethyl]aminocarbonyl-benzyl | —CONH— | 2-benzimidazole | H | 814.4 | 152.5 |
| 289 | 3-(3-pyridyl)methylaminocarbonyl-benzyl | —CONH— | 2-benzimidazole | H | 800.3 | 164 |
| 290 | 3-(2-methoxy)ethylaminocarbonyl-benzyl | —CONH— | 2-benzimidazole | H | 767.3 | 152.5 |
| 291 | 3-(2-dimethylamino)-ethylaminocarbonyl-benzyl | —CONH— | 2-benzimidazole | H | 780.4 | 160.5 |
| 292 | 3-[2-(1-morpholinyl)-ethyl]aminocarbonyl-benzyl | —CONH— | 2-benzimidazole | H | 822.4 | 162.5 |
| 293 | 3-[2-(1-piperidyl)-ethyl]aminocarbonyl-benzyl | —CONH— | 2-benzimidazole | H | 820.5 | 160 |
| 294 | 3-(2-pyridylmethyl)aminocarbonyl-benzyl | —CONH— | 2-benzimidazole (HCl salt) | H | 800.6 | 186.5 |
| 295 | 3-[2-(2-pyridyl)-ethyl]aminocarbonyl-benzyl | —CONH— | 2-benzimidazole (HCl salt) | H | 814 | 182.5 |
| 296 | 3-(ethyl)aminocarbonyl-benzyl | —CONH— | 2-imidazole | H | 687.5 | 153.5 |

TABLE 2-continued

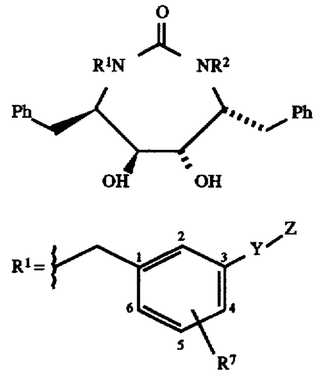

| Ex. No. | $R_2$ | Y | Z | $R_7$ | MS | MP |
|---|---|---|---|---|---|---|
| 297 | 3-(2-methoxy)ethylaminocarbonyl-benzyl | —CONH— | 2-imidazole | H | 717.6 | 147.5 |
| 298 | 3-(2-pyridylmethyl)aminocarbonyl-benzyl | —CONH— | 2-imidazole | H | 750.5 | 157.5 |
| 299 | 3-(2-pyridylmethyl)aminocarbonyl-benzyl | —CONH— | 2-imidazole | H | 382.9 (M + 2H) /2 | 119.5 |
| 300 | 3-amino-5-indazolyl-methyl | —CONH— | 2-benzimidazole | H | 721.4 | 197.5 |
| 301 | 3-amino-5-indazolyl-methyl | —CONH— | 2-imidazole | H | 336.3 (M + 2H) /2 | 177.5 |
| 302 | 3-(n-propyl)aminocarbonyl-benzyl | —CONH— | 2-imidazole | H | 701.6 | 156.5 |
| 303 | 3-(2-methoxy)ethylaminocarbonyl-benzyl | —CONH— | 2-imidazole | H | 731.6 | 136.5 |
| 304 | 3-(3-methoxy)propylaminocarbonyl-benzyl | —CONH— | 2-imidazole | H | 731.6 | 158.5 |
| 305 | 3-amino-5-indazolyl-methyl | —CONH— | 5,6-dimethyl-2-benzimidazole | H | 749.5 | 197.5 |
| 306 | 3-(n-butyl)aminocarbonyl-benzyl | —CONH— | 2-imidazole | H | 715.6 | 154.5 |
| 307 | 3-(n-hexyl)aminocarbonyl-benzyl | —CONH— | 2-imidazole | H | 743 | 136.5 |
| 308 | 3-(2-ethoxy-ethyl)aminocarbonyl-benzyl | —COHN— | 2-benzimidazole | H | 781.6 | 146 |
| 309 | 3-(n-pentyl)aminocarbonyl-benzyl | —CONH— | 2-imidazole | H | 729.7 | 140.5 |
| 310 | 3-amino-5-indazolyl-methyl | —CONH— | 4,5-dimethyl-2-imidazole | H | 699.4 | 190 |
| 311 | 3-(2-phenoxyethyl)aminocarbonyl-benzyl | —CONH— | 2-benzimidazole | H | 829.2 | 132 |
| 312 | 3-(2-phenoxyethyl)aminocarbonyl-benzyl | —CONH— | 2-imidazole | H | 779.2 | 138.5 |
| 313 | 3-(2-propoxyethyl)aminocarbonyl-benzyl | —CONH— | 2-benzimidazole | H | 795.3 | 140.5 |
| 314 | 3-(2-propoxyethyl)aminocarbonyl-benzyl | —CONH— | 2-imidazole | H | 745.4 | 128 |
| 315 | 3-amino-5-indazolyl-methyl | —CONH— | 5,6-dimethyl-2-benzimidazole | H | 749.3 | 197.5 |
| 316 | 3-methoxy-propyl | —CONH— | 2-pyridine | H | 609.4 | 80–82 |
| 317 | 3-methoxy-propyl | —CONH— | 4-methyl-2-pyridine | H | 623.4 | 84–86 |
| 318 | 3-methoxy-propyl | —CONH— | 5-methyl-2- | H | 623.5 | 86–88 |

TABLE 2-continued

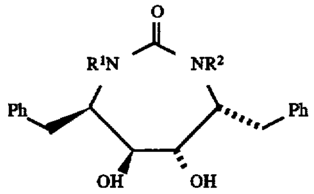

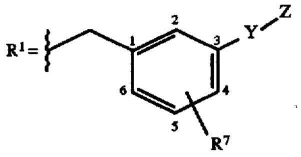

| Ex. No. | $R_2$ | Y | Z | $R_7$ | MS | MP |
|---|---|---|---|---|---|---|
| | | | pyridine | | | |
| 319 | 3-methoxy-propyl | −CONH− | 6-methyl-2-pyridine | H | 623.4 | 83–85 |
| 320 | 3-methoxy-propyl | −CONH− | 2-imidazole | H | 598.4 | 118–120 |
| 321 | 3-methoxy-propyl | −CONH− | 2-benzimidazole | H | 648.4 | 107–108.5 |
| 322 | 5-benzotriazole-methyl | −CONH− | 5-methyl-2-pyridine | H | 682.3 | 152–154 |
| 323 | 5-benzotriazole-methyl | −CONH− | 2-pyridine | H | 668.5 | 142–144 |
| 324 | 5-benzotriazole-methyl | −CONH− | 2-benzotriazole | H | 707.2 | 173–175 |
| 325 | 5-benzotriazole-methyl | −CONH− | 2-imidazole | H | 657.2 | 174–1.76 |
| 326 | 3-(2-pyridoxy)-benzyl | −CONH− | 2-benzimidazole | H | 759.5 | 126–128 |
| 327 | 3-(2-pyridoxy)-benzyl | −CONH− | 2-imidazole | H | 709.4 | 114–116 |
| 328 | 3-aminocarbonyl-benzyl | −CONH− | 2-benzimidazole | H | 709.4 | 158–160 |
| 329 | 3-aminocarbonyl-benzyl | −CONH− | 2-imidazole | H | 659.5 | 150–152 |
| 330 | 3-methoxyaminocarbonyl-benzyl | −CONH− | 2-imidazole | H | 689.6 | 145–147 |
| 331 | piperonyl | −CONH− | 4-methyl-2-pyridine | H | 685.3 | 112–113 |
| 332 | piperonyl | −CONH− | 5-methyl-2-pyridine | H | 685.3 | 251–253 |
| 333 | piperonyl | −CONH− | 6-methyl-2-pyridine | H | 685.3 | 263.5–265 |
| 334 | piperonyl | −CONH− | 2-pyridine | H | 671.3 | 230.5–232 |
| 335 | piperonyl | −CONH− | 2-benzimidazole | H | 710.3 | 235–237 |
| 336 | piperonyl | −CONH− | 2-imidazole | H | 660.3 | 231–234 |
| 337 | 3-(2-pyridylmethyl)amino-benzyl | −CONH− | 2-pyridine | H | 733 | |
| 338 | 3-(n-propyl)amino-benzyl | −CONH− | 2-pyridine | H | 684 | 122–125 |
| 339 | 3-(2-pyridyl)ureido-benzyl | −CONH− | 2-pyridine | H | 762.2 | 138–140 |
| 340 | 3-(6-methyl-2-pyridyl)ureido-benzyl | −CONH− | 6-methyl-2-pyridine | H | 790.3 | >170 (d) |
| 341 | 3-amino-benzyl | −CONH− | 6-methyl-2-pyridine | H | 656.4 | >200 (d) |
| 342 | 3-amino-benzyl | −CONH− | 2-benzimidazole | H | 681.3 | >130 (d) |
| 343 | 3-amino-benzyl | −CONH− | 2-pyrazine | H | 643.3 | 125–126 |
| 344 | 3-(carboethoxy)methylamino-benzyl | −CONH− | 2-pyrazine | H | 729.3 | 101–102 |
| 345 | 3-amino-benzyl | −CONH− | 2-imidazole | H | 631.5 | 141–143 |
| 346 | H | −CONH− | 2-benzimidazole | H | 576.7 | 183–185 |
| 347 | 3-dipropylamino-benzyl | −CONH− | 2-benzimidazole | H | 765.6 | 128–130 |
| 348 | 3-(carboethoxy)methylamino-benzyl | −CONH− | 2-benzimidazole | H | 767 | >175 |
| 349 | 3-(ethoxylcarbonyl)amino-benzyl | −CONH− | 2-benzimidazole | H | 753.4 | 144–147 |

TABLE 2-continued

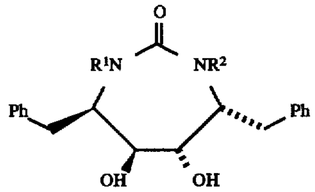

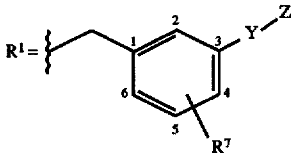

| Ex. No. | $R_2$ | Y | Z | $R_7$ | MS | MP |
|---|---|---|---|---|---|---|
| 350 | 3-amino-benzyl | —CONH— | 2-imidazole (2HCl salt) | H | | 198–201 |
| 351 | 3-methylamino-benzyl | —CONH— | 2-imidazole | H | 645.4 | |
| 352 | 2,3,5,6-tetra-fluoro-4-methoxy-benzyl | —CONH— | 2-imidazole | H | 718.2 | >220 |
| 353 | 3-(L-Ala-L-Ala)amino-benzyl | —CONH— | 2-imidazole | H | 773.4 | >150 (d) |
| 354 | $R_1$ | —CONH— | 5-methyl-3 isoxazole | H | 755 | |
| 355 | 2-methyl-allyl | —CONH— | 2-imidazole | H | 580 | |
| 356 | 3,3-dimethyl-allyl | —CONH— | 2-imidazole | H | 594 | |
| 357 | 3-amino-benzyl | —CONH— | 5,6-dimethyl-2-benzimidazole | H | 709.6 | 175 |
| 358 | 3-amino-benzyl | —CONH— | 5-carbomethoxy-2-benzimidazole | H | 739.7 | 195 |
| 359 | 3-amino-benzyl | —CONH— | 5-carboxy-2-bezimidazole | H | 725.6 | 210–215 (d) |
| 360 | 5-indazoly-methyl | —CONH— | 5-methyl-2-pyridine | H | 681.3 | 139–141 |
| 361 | 5-indazoly-methyl | —CONH— | 2-pyridine | H | 667.4 | 150–152 |
| 362 | 3-amino-4-fluoro-benzyl | —CONH— | 2-benzimidazole | 4-F | 717.5 | 162–164 |
| 363 | 3-amino-4-fluoro-benzyl | —CONH— | 2-imidazole | H | 649 | 153–155 |
| 364 | $R_1$ | —CONH— | 5-methylthio-3-1,2,3-triazole | H | 819.0 | 215–217 |
| 365 | 3-(3-hydroxy)propyl-benzyl | —CONH— | 2-benzimidazole | H | 724 | 144–149 |
| 366 | $R_1$ | —CONH— | 4,6-dichloro-2-pyridine | H | 885 | 238–241 |
| 367 | $R_1$ | —CONH— | 2-pyrazine | H | 749 | 146–148 |
| 368 | $R_1$ | —CONH— | 5-bromo-2-pyridine | H | 905 | 162–164 |
| 369 | $R_1$ | —CONH— | 4-methyl-pyrimidine | H | 777 | 154–159 |
| 370 | $R_1$ | —CONH— | 4-methyl-2-oxazole | H | 755 | 155–157 |
| 371 | 3,5-dimethoxy-benzyl | —CONH— | 2-pyrazine | H | 688 | 151–153 |
| 372 | 3,5-dimethoxy-benzyl | —CONH— | 5-methyl-2-pyridine | H | 701 | 236–238 |
| 373 | 3,5-dimethoxy-benzyl | —CONH— | 6-methyl-2-pyridine | H | 701 | 207–209 |
| 374 | 3,5-dimethoxy-benzyl | —CONH— | 2-pyridine | H | 687 | 215–218 |
| 375 | 3-methoxy-benzyl | —CONH— | 2-pyrazine | H | 658 | 112 (d) |
| 376 | 3-methoxy-benzyl | —CONH— | 5-methyl-2-pyridine | H | 671 | 238–240 |
| 377 | 3-methoxy-benzyl | —CONH— | 6-methyl-2-pyridine | H | 671 | 243–245 |
| 378 | 3-methoxy-benzyl | —CONH— | 2-pyridine | H | 657 | 223–225 |
| 379 | 3-amino-benzyl | —CONH— | 5-methyl-2-pyridine | H | 656 | 230–232 |
| 380 | 3-nitro-benzyl | —CONH— | 2-pyridine | H | 672 | 235–238 |
| 381 | $R_1$ | —CONH— | 5-trifluoromethyl-2-pyridine | H | | |
| 382 | 3-amino-benzyl | —CONH— | 4,5-dimethyl-2-imidazole | H | | |

TABLE 2-continued

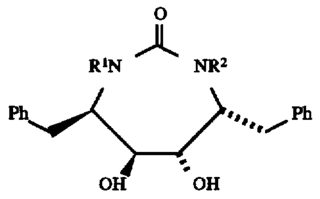

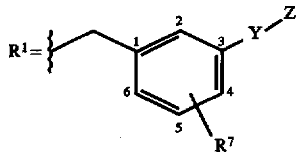

| Ex. No. | $R_2$ | Y | Z | $R_7$ | MS | MP |
|---|---|---|---|---|---|---|
| 383 | 3-(2-thiazoloxy)-benzyl | —CONH— | 2-benzimidazole | H | | amorphous |
| 384 | 3-(2-thiazoloxy)-benzyl | —CONH— | 2-imidazole | H | | amorphous |
| 385 | 3-(2-pyridyl)-benzyl | —CONH— | 2-benzimidazole | H | 743.5 | 156–160 |
| 386 | 3-(3-pyridyl)-benzyl | —CONH— | 2-benzimidazole | H | 743.5 | 175–180 |
| 387 | 1-phenyl-4-pyrazoylmethyl | —CONH— | 2-benzimidazole | H | 732.4 | 163–168 |
| 388 | 2-methyl-allyl | —CONH— | 2-pyridine | H | 591 | 162 |
| 389 | 4-chloro-benzyl | —CONH— | 2-quinoline | H | 711 | 215–218 |
| 390 | 5-indazolyl-methyl | —CONH— | 2-quinoline | H | 717.4 | 218–221 |
| 391 | benzyl | —CONH— | 2-quinoline | H | 677.3 | 198–200 |
| 392 | cyclopropyl-methyl | —CONH— | 2-quinoline | H | 641 | 208–210 |
| 393 | 3-amino-benzyl | —CONH— | 2-quinoline | H | 346.9 (M + 2H) /2 | 225–227 |
| 394 | 3-dimethylamino-benzyl | —CONH— | 2-benzimidazole | H | 709 | |
| 395 | 3-dimethylamino-benzyl | —CONH— | 2-imidazole | H | 330.4 (M + H)/ 2 | 258–259 |
| 396 | isopentyl | —CONH— | 2-benzimidazole | H | 646 | 166–168 |
| 397 | isobutyl | —CONH— | 2-benzimidazole | H | 632 | 170–172 |
| 398 | 5-indazolyl-methyl | —CONH— | 5,6-dimethyl-2-benzimidazole | 4-$NH_2$ | 749 | amorphous |
| 399 | 3-acetyl-benzyl | —CONH— | 2-quinoline | 4-$NH_2$ | 734 | 208–210 |
| 400 | 3-acetyl-benzyl | —CONH— | 2-imidazole | 4-$NH_2$ | 673 | 194 |
| 401 | 3-acetoxime-benzyl | —CONH— | 2-imidazole | 4-$NH_2$ | 688 | amorphous |
| 402 | 3-cyano-benzyl | —CONH— | 2-imidazole | 4-$NH_2$ | 656 | amorphous |
| 403 | H | —CONH— | 2-imidazole | H | 526.5 | 152–155 |
| 404 | H | —CONH— | 5,6-dimethyl-2-bezimidazole | H | 604.6 | 189–191 |
| 405 | methyl | —CONH— | 2-benzimidazole | H | 590.6 | 145–148 |
| 406 | methyl | —CONH— | 2-imidazole | H | 540.5 | 127–130 |
| 407 | 3-pyridylmethyl | —CONH— | 2-benzimidazole | H | 667.5 | 152–155 |
| 408 | isopentyl | —CONH— | 2-pyridine | H | 607 | |
| 409 | $R_1$ | —CONH— | 2-benzimidazole | 4-$NH_2$ | 855 | 290 |
| 410 | 3-amino-benzyl | —CONH— | 2-imidazole | 4-$NH_2$ | 646 | 168–172 |
| 411 | 3-amino-benzyl | —CONH— | 2-benzimidazole | 4-$NH_2$ | 696 | 139–146 |
| 412 | 3-amino-benzyl | —CONH— | 5,6-dimethyl-2-bezimidazole | 4-$NH_2$ | 724 | amophous |
| 413 | 3-acetyl-benzyl | —CONH— | 2-benzimidazole | 4-$NH_2$ | 723 | amorphous |
| 414 | 3-acetyl-benzyl | —CONH— | 5,6-dimethyl-2-bezimidazole | 4-$NH_2$ | 751 | amorphous |
| 415 | 3-(2-hydroxy-isopropyl)-benzyl | —CONH— | 2-benzimidazole | 4-$NH_2$ | 739 | amorphous |
| 416 | 6-hydroxymethyl-3-pyridyl-methyl | —CONH— | 2-benzimidazole | H | | |
| 417 | 6-chloro-3-pyridyl-methyl | —CONH— | 2-imidazole | H | 651 | amorphous |
| 418 | $R_1$ | —CONH— | 1-isonicotinyl-2-benzimidazole | H | 1035 | |
| 419 | 3-methoxyaminocarbonyl-benzyl | —CONH— | 2-benzimidazole | H | 739.6 | 152–154 |
| 420 | 3-methylaminocarbonyl- | —CONH— | 2-imidazole | H | 673.6 | 147–149 |

TABLE 2-continued

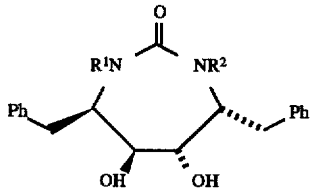

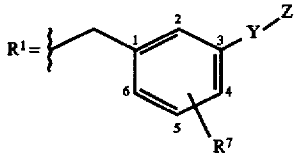

| Ex. No. | $R_2$ | Y | Z | $R_7$ | MS | MP |
|---|---|---|---|---|---|---|
| | benzyl | | | | | |
| 421 | 3-(2-pyridoxy)-benzyl | —CONH— | 2-pyrazine | H | 721.6 | 95–97 |
| 422 | 3-methylaminocarbonyl-benzyl | —CONH— | 2-pyrazine | H | 685.6 | 121–123 |
| 423 | 3-aminocarbonyl-benzyl | —CONH— | 2-pyrazine | H | 671.6 | 124–126 |
| 424 | 3-methoxyaminocarbonyl-benzyl | —CONH— | 2-pyrazine | H | 701.6 | 105–107 |
| 425 | 3-methoxyaminocarbonyl-benzyl | —CONH— | 2-benzimidazole | H | 723.6 | 105–107 |
| 426 | 4-bromo-3-amino-benzyl | —CONH— | 2-imidazole | H | 711.3 | 152–154 |
| 427 | 4-methoxy-3-amino-benzyl | —CONH— | 2-imidazole | H | 661.4 | 141–143 |
| 428 | 4-bromo-3-amino-benzyl | —CONH— | 2-benzimidazole | H | 761.2 | 154–156 |
| 429 | 4-methoxy-3-amino-benzyl | —CONH— | 2-benzimidazole | H | 711.4 | 206–208 |
| 430 | 5-benzoxazolonyl-methyl | —CONH— | 2-benzimidazole | H | 723.3 | 178–180 |
| 431 | 3-amino-benzyl | —CONH— | 2-imidazole | 4-$CH_3O$ | 661.3 | 142–144 |
| 432 | 3-amino-benzyl | —CONH— | 2-benzimidazole | 4-$CH_3O$ | 711.3 | 152–154 |
| 433 | $R_1$ | —CONH— | 1-(4-dimethylamino)benzoyl-2-benzimidazole | H | 1120 | |
| 434 | 3-(2-benzimidazole)aminocarbony-benzyl | —CONH— | 1-(4-dimethylamino)benzoyl-2-benzimidazole | H | 973 | |
| 435 | 3-(1-pyrazolyl)-benzyl | —CONH— | 2-benzimidazole | H | 732.4 | 163–168 |
| 436 | 3-amino-benzyl | —CONH— | 5-methyl-3-isoxazole | H | 646.4 | 193–200 |
| 437 | 3-amino-benzyl | —CONH— | 5-ethylthio-1,3,4-thiadiazole | H | 709 | 141–142 |
| 438 | 3-amino-benzyl | —CONH— | 1,3,4-thiadiazole | H | 649.3 | 223-225 |
| 439 | 3-amino-benzyl | —CONH— | 5-t-butyl-1,3,4-thiadiazole | H | 705.3 | 178–180 |
| 440 | 3-amino-benzyl | —CONH— | 5-methylthio-1,3,4-triazole | H | 678 | 230–232 |
| 441 | 3-amino-benzyl | —CONH— | 1-methyl-3-pyrazole | H | 645.3 | 245–247 |
| 442 | 3-amino-benzyl | —CONH— | 2-imidazole | H | 649.3 | 178–180 |
| 443 | 2-methyl-4-thiazolylmethyl | —CONH— | 2-benzimidazole | H | 687.5 | 172–174 |
| 444 | 3-pyridylmethyl | —CONH— | 2-imidazole | H | 617.4 | 162–164 |
| 445 | 3-amino-benzyl | —CONH— | 4-methyl-2-imidazole | H | 645.3 | 196–198 |
| 446 | 3-(1-pyrazolyl)-benzyl | —CONH— | 2-imidazole | H | 682.3 | 151–153 |
| 447 | $R_1$ | —CONH— | 4-methyl-2-imidazole | H | 753.8 | 189–191 |
| 448 | $R_1$ | —CONH— | 5-amino-2- | H | 855.4 | 226–228 |

TABLE 2-continued

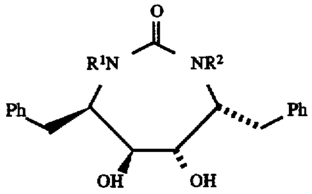

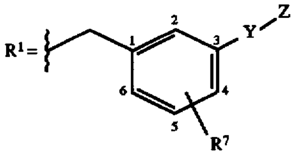

| Ex. No. | $R_2$ | Y | Z | $R_7$ | MS | MP |
|---|---|---|---|---|---|---|
| 449 | $R_1$ | −CONH− | benzimidazole 5-dimethylamino-2-bezimidazole | H | 911.2 | 205–207 |
| 450 | 4-amino-benzyl | −CONH− | 2-imidazole | H | 631.4 | 158–161 |
| 451 | 3-amino-4-methyl-benzyl | −CONH− | 2-imidazole | H | 645.4 | 151–153 |
| 452 | 3-gycinamido-4-fluoro-benzyl | −CONH− | 2-imidazole | H | 706.2 | 155–157 |
| 453 | 3-isobutylamino-carbonyl-benzyl | −CONH− | 2-benzimidazole | H | 765 | |
| 454 | R1 | −CONH− | 2-imidazole | 4-F | 761.2 | 175–180 |
| 455 | 3-amino-4-chloro-benzyl | −CONH− | 2-benzimidazole | H | 715.3 | 148–149 |
| 456 | 3-amino-4-chloro-benzyl | −CONH− | 2-imidazole | H | 665.3 | 142–143 |
| 457 | 4-amino-3-methoxy-benzyl | −CONH− | 2-benzimidazole | H | 711.3 | 146–147 |
| 458 | 4-amino-3-methoxy-benzyl | −CONH− | 2-imidazole | H | 661.3 | 149–150 |
| 459 | 3-amino-4-trifluoromethyl-benzyl | −CONH− | 2-benzimidazole | H | 749.3 | 148–150 |
| 460 | 3-amino-4-trifluoromethyl-benzyl | −CONH− | 2-imidazole | H | | 138–139 |
| 461 | 3-(N,N-dimethyl)glycinamido-benzyl | −CONH− | 2-imidazole | H | 716 | 137–142 |
| 462 | 3-isopentylaminocarbony l-benzyl | −CONH− | 2-benzimidazole | H | 779 | |
| 463 | 3-cyclobutylaminocarbon yl-benzyl | −CONH− | 2-benzimidazole | H | 763 | |
| 464 | $R_1$ | −CONH− | 2-pyrimid-4-one | H | | |
| 465 | $R_1$ | −CONH− | 4-pyrimid-2-one | H | | |
| 466 | 3-aminobenzyl | −CONH− | 2-ethyl3-pyrazole | H | 659 | |
| 467 | 3-aminobenzyl | −CONH− | 5-uracil | H | 675 | |
| 468 | 3-cyclopentylaminocarbo nyl-benzyl | −CONH− | 2-benzimidazole | H | 777 | |
| 469 | 3-(2-pyridyl)methylaminoca rbonyl-benzyl | −CONH− | 2-benzimidazole | H | 800 | |
| 470 | 3-(2-hydroxy)ethylaminocar bonyl-benzyl | −CONH− | 2-benzimidazole | H | 753 | |
| 471 | 3-aminobenzyl | −CONH− | 6-coumarin | H | 709.3 | 240–242 |
| 472 | 3-(2-hydroxyisopropyl)-benzyl | −CONH− | 2-imidazole | 4-$NH_2$ | 689 | amorphous |
| 473 | 3-glycinamido-benzyl | −CONH− | 2-imidazole | H | 688.32 | >173 |
| 474 | $R_1$ | −CONH− | 1-methyl-4-pyrimid-2-one | H | | |
| 475 | 3-(1-hydroxy)ethyl-benzyl | −CONH− | 2-benzimidazole | 4-$NH_2$ | 725 | amorphous |
| 476 | $R_1$ | −CONH− | 4,5-dimethyl-2- | H | 815.3 | |

TABLE 2-continued

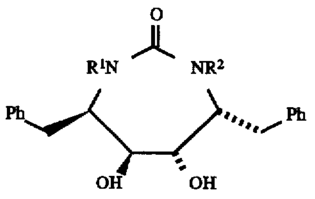

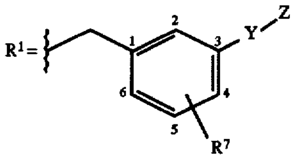

| Ex. No. | $R_2$ | Y | Z | $R_7$ | MS | MP |
|---|---|---|---|---|---|---|
| | | | thiazole | | | |
| 477 | benzyl | −CONH− | 5,6-dimethyl-2-benzimidazole | H | | |
| 478 | 3-(2-benzimidazolyl)aminocarbonyl-benzyl | −CONH− | 5,6-dimethyl-2-benzimidazole | H | | |
| 479 | 3-(2-benzimidazolylmethyl) aminocarbonyl-benzyl | −CONH− | 5,6-dimethyl-2-benzimidazole | H | | |
| 480 | cyclopropylmethyl | −CONH− | 5,6-dimethyl-2-benzimidazole | H | | |
| 481 | $R_1$ | −CONH− | Ph | $4-NH_2$ | | |
| 482 | cyclopropylmethyl | −CONH− | 5-nitro-2-thiazole | H | | |
| 483 | 3-amino-benzyl | −NHCO− | 4-imidazolin-2-one | H | | |
| 484 | $R_1$ | −NHCO− | 4-imidazolin-2-one | H | | |
| 485 | 3-amino-benzyl | −NHCO− | 4-pyridine (2HCl salt) | H | 642 | 208 (d) |
| 486 | $R_1$ | −NHCO− | 4-pyridine (2HCl salt) | H | 747 | 205 (d) |
| 487 | 3-methoxy-benzyl | −O− | 2-thiazole | H | 636.2 | |
| 488 | 3-amino-5-indazolyl-methyl | −O− | 2-pyridine | H | 655.4 | 119–121 |
| 489 | 5-indazolyl-methyl | −O− | 2-pyridine | H | 640.5 | 107–109 |
| 490 | 3-amino-benzyl | −O− | 2-pyridine | H | 615.6 | 156–158 |
| 491 | 3-amino-benzyl | −O− | 2-thiazole | H | 621.6 | 78–79 |
| 492 | 3-carbomethoxy-benzyl | −NHCONH− | 2-pyridine | H | 700.4 | |
| 493 | 5-indazolyl-methyl | −NHCONH− | 2-imidazole | H | 671.3 | 173–175 |
| 530 | R1 | $-CH_2NH-$ | 2-thiazole | H | | |
| 531 | 3-(2-hydroxy-isopropyl)-benzyl | −CONH− | 4-methyl-2-pyridyl | H | | |
| 532 | cyclopropyl-methyl | $SO_2NH$ | 2-benzimidazole | H | | |
| 533 | 5-indazolyl-methyl | $SO_2NH$ | 2-imidazole | H | | |
| 534 | n-butyl | $SO_2NH$ | 2-imidazole | H | | |
| 535 | 4-fluoro-3-amino-benzyl | CONH | 2-imidazole | F | | |
| 536 | iso-butyl | CONH | 2-pyridine | H | | |

TABLE 3
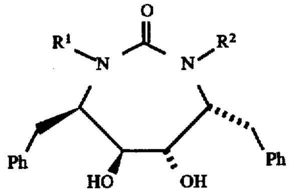
| Ex. No. | $R_2$ | $R_1$ | MS | MP |
|---|---|---|---|---|
| 500 | 3-thienyl-methyl | 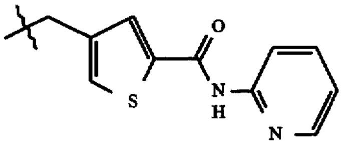 | 639 | amorphous |
| 501 | 3-thienyl-methyl | 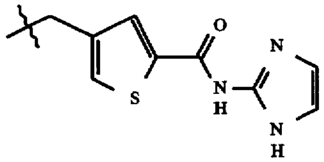 | 628 | amorphous |
| 502 | $R_1$ | 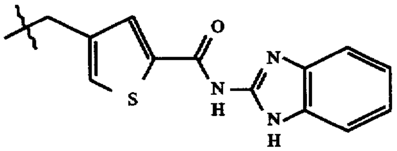 | 838 | amorphous |
| 503 | 3-thienyl-methyl | 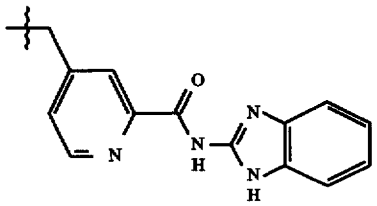 | 673 | amorphous |
| 537 | R1 | 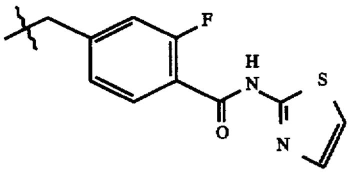 | | |

TABLE 4

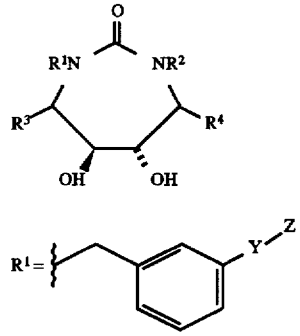

| Ex. No. | $R_2$ | Y | Z | $R_3$ | $R_4$ | MS | MP |
|---|---|---|---|---|---|---|---|
| 504 | $R_1$ | —CONH— | 2-imidazole | i-butyl | i-butyl | 691 | |
| 505 | $R_1$ | —CONH— | 2-benzimidazole | i-butyl | i-butyl | 757 | |
| 506 | $R_1$ | —CONH— | 2-benzimidazole | n-hexyl | n-hexyl | 813 | 171–175 |
| 507 | $R_1$ | —CONH— | 2-benzimidazole | benzyl | n-hexyl | 819 | 188–191 |
| 508 | $R_1$ | —CONH— | 2-benzimidazole | benzyl | ethyl | 763 | 197–201 |
| 509 | $R_1$ | —CONH— | 2-benzimidazole | benzyl | i-butyl | 791 | 202–207 |
| 510 | $R_1$ | —CONH— | 2-benzimidazole | ethyl | ethyl | 701 | >250 |
| 511 | 3-carbomethoxy-benzyl | —CONH— | 2-benzimidazole | 4-methoxy-benzyl | 4-methoxy-benzyl | 784 | |
| 512 | 3-carbomethoxy-benzyl | —CONH— | 2-pyridine | i-butyl | i-butyl | 617 | |
| 513 | 3-carbomethoxy-benzyl | —CONH— | 2-imidazole | i-butyl | i-butyl | 606 | |
| 514 | $R_1$ | —CONH— | 2-benzimidazole | 3,4-ethylidene-benzyl | 3,4-ethylidene-benzyl | 942 | 227–232 |
| 515 | 3-(2-imidazolyl)aminocarbonyl-benzyl | —CONH— | 2-benzimidazole | i-butyl | i-butyl | 707 | |
| 516 | $R_1$ | —CONH— | 2-benzimidazole | cyclohexylmethyl | cyclohexylmethyl | 837 | 225–227 |
| 517 | 3-carbomethoxy-benzyl | —CONH— | 2-benzimidazole | 4-methoxy-benzyl | 4-methoxy-benzyl | 784 | |
| 518 | $R_1$ | —CONH— | 2-benzimidazole | 4-benzyloxy-benzyl | 4-benzyloxy-benzyl | 1037 | |
| 519 | $R_1$ | —CONH— | 2-benzimidazole | 4-hydroxy-benzyl | 4-hydroxy-benzyl | 857 | 203–205 |
| 520 | $R_1$ | —CONH— | 2-imidazole | 4-benzyloxy-benzyl | 4-benzyloxy-benzyl | 937 | |
| 521 | $R_1$ | —CONH— | 2-imidazole | 4-hydroxy-benzyl | 4-hydroxy-benzyl | 757 | |
| 522 | $R_1$ | —O— | 2-thiazole | 3,4-ethylidene-benzyl | 3,4-ethylidene-benzyl | 821 | 176–179 |
| 523 | $R_1$ | —O— | 2-thiazole | 1,4-benzoxazin-6-yl-methyl | 1,4-benzoxazin-6-yl-methyl | 848 | 144–145 |

TABLE 5

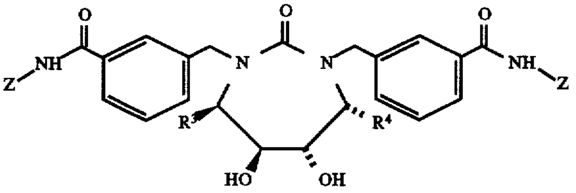

| Ex. No. | Z | $R^3$=$R^4$ | MS | MP |
|---|---|---|---|---|
| 201 | 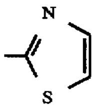 | 3-methoxybenzyl | | |

TABLE 5-continued
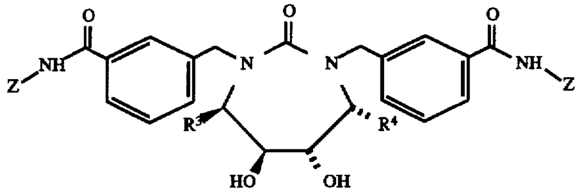
| Ex. No. | Z | $R^3 = R^4$ | MS | MP |
|---|---|---|---|---|
| 202 | 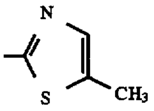 | 3-methoxybenzyl | | |
| 203 | 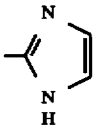 | 3-methoxybenzyl | | |
| 204 | 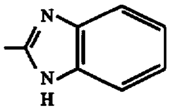 | 3-methoxybenzyl | | |
| 205 | 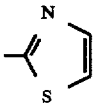 | 4-methoxybenzyl | | |
| 206 | 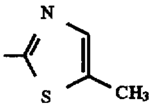 | 4-methoxybenzyl | 847 | |
| 207 | 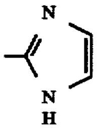 | 4-methoxybenzyl | | |
| 208 | 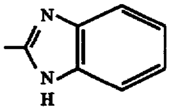 | 4-methoxybenzyl | 885 | |
| 209 | 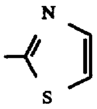 | 4-methylthiobenzyl | | |
| 210 | 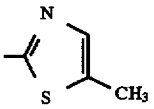 | 4-methylthiobenzyl | | |
| 211 | 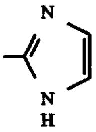 | 4-methylthiobenzyl | | |

TABLE 5-continued

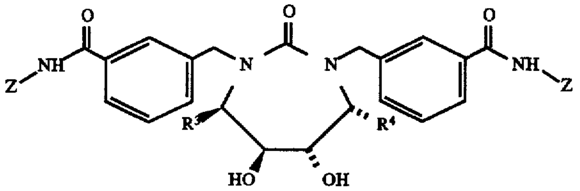

| Ex. No. | Z | $R^3 = R^4$ | MS | MP |
|---|---|---|---|---|
| 212 | 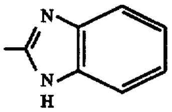 | 3-methylthiobenzyl | | |
| 213 | 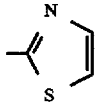 | 4-N,N-dimethylamino benzyl | | |
| 214 | 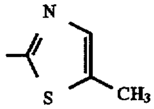 | 4-N,N-dimethylamino benzyl | | |
| 215 | 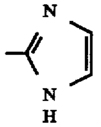 | 4-N,N-dimethylamino benzyl | | |
| 216 | 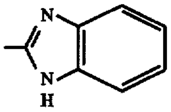 | 4-N,N-dimethylamino benzyl | 911 | 198–203 |
| 217 | 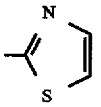 | 4-(4-pyridinylmethoxy) benzyl | | |
| 218 | 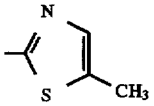 | 4-(4-pyridinylmethoxy) benzyl | | |
| 219 | 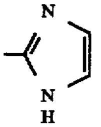 | 4-(4-pyridinylmethoxy) benzyl | | |
| 220 | 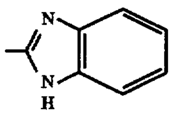 | 4-(4-pyridinylmethoxy) benzyl | | |

Dosage and Formulation

The antiviral compounds of this invention can be administered as treatment for retroviral infections by any means that produces contact of the active agent with the agent's site of action, the retroviral protease, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The compounds of the present invention can be administered in oral dosage forms as tablets, capsules (each of which includes sustained release or timed release formulations), pills, powders, granules, elixirs, tinctures, suspensions, syrups, and emulsions. The compounds of the present invention may also be administered in intravenous (bolus or infusion), intraperitoneal, subcutaneous, or intramuscular form, all using dosage forms well known to those of ordinary skill in the pharmaceutical arts. An effective amount of the compound desired can be administered for the inhibition of HIV and the treatment of HIV infection.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses may range from about 1 to about 10 mg/kg/minute during a constant rate infusion. Compounds of the present invention may be administered in a single daily dose, or the total daily dosage may be administered in divided doses of two, three, or four times daily.

The compounds for the present invention may also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as a pharmaceutically acceptable carrier or carrier materials) suitably selected with respect to the intended form of administration, that is, oral tablets, capsules, elixirs, syrups and the like, and consistent with conventional pharmaceutical practices.

For instance, for oral administration in the dosage unit form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid dosage form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (compositions suitable for administration) contain from about 1 milligram to about 100 milligrams of active ingredient per dosage unit. In these pharmaceutical compositions the active ingredient will ordinarily be present in an amount of about 0.5–95% by weight based on the total weight of the dosage unit.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of formula (I) of the present invention may be administered in combination with a second therapeutic agent, such as a second HIV inhibitory agent or other therapeutic agent for treatment of HIV associated disease conditions. The compound of formula (I) and such second therapeutic agent can be administered separately or as a physical combination in a single dosage unit, in any dosage form and by various routes of administration, as described above. The compound of formula (I) may be formulated together with the second therapeutic agent in a single dosage unit (that is, combined together, for example, in one capsule, tablet, powder, or liquid). When the compound of formula (I) and the second therapeutic agent are not formulated together in a single dosage unit, the compound of formula (I) and the second therapeutic agent may be administered essentially at the same time, or in any order; for example, the compound of formula (I) may be administered first, followed by administration of the second agent. When not administered at the same time, it is preferable that the administration of the compound of formula (I) and the second therapeutic agent occurs on the same day and, more preferably within about one hour apart.

The present invention also includes pharmaceutical kits useful, for example, for the treatment of HIV infection, which comprise one or more containers containing a pharmaceutical composition comprising a therapeutically effective amount of a compound of formula (I). Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of the formula (I):

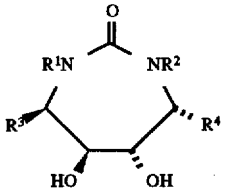

(I)

or a pharmaceutically acceptable salt form thereof wherein:

$R^1$ is $—CH_2—X—Y—Z$;

X is selected from:

$C_1$–$C_4$ alkyl, aryl substituted with 0–2 $R^7$, wherein said aryl group is phenyl or naphthyl, $C_3$–$C_6$ cycloalkyl, or a heterocycle selected from the group consisting of pyridine, thiophene, furan, thiazole, indazole, thieno[2,3-c]pyrazole and thieno[3,2-c]pyrazole, said heterocycle being substituted with 0–2 $R^7$;

Y is selected from:

$—(CH_2)_nO—$,
$—(CH_2)_nS—$,
$—(CH_2)_nNH—$,
$—(CH_2)_nC(=O)NH—$,
$—(CH_2)_nSO_2NH—$
$—(CH_2)_mNHC(=O)—$,
$—(CH_2)_nNHCO_2—$,
$—(CH_2)_mOC(=O)\ NH—$,
$—(CH_2)_nNHC(=O)\ NH—$,
$—(CH_2)_nC(=NH)\ NH—$;

n is 0–2;

m is 1–2;

Z is selected from:

2-, 3-, or 4-pyridinyl, substituted with 0–1 $R^5$ and 0–1 $R^6$;

2-pyrimidinyl, substituted with 0–1 $R^5$ and 0–1 $R^6$;

2-pyrazinyl, substituted with 0–1 $R^5$ and 0–1 $R^6$;

4-pyrimidon-2-yl or 2-pyrimidon-4-yl, substituted with 0–1 $R^5$ and 0–1 $R^6$;

6H-1,3,4-thiadiazin-2-yl, substituted with 0–1 $R^5$ and 0–1 $R^6$;

5-uracilyl, substituted with 0–1 $R^5$ and 0–1 $R^6$;

2-, 3-, or 4-quinolinyl, substituted with 0–1 $R^5$ and 0–1 $R^6$;

1-, 3-, or 4-isoquinolinyl, substituted with 0–1 $R^5$ and 0–1 $R^6$;

5- or 6-coumarinyl, substituted with 0–1 $R^5$ and 0–1 $R^6$;

3-tetrahydrofuranyl, substituted with 0–1 $R^5$ and 0–1 $R^6$;

2- or 3-pyrrolidinyl, substituted with 0–1 $R^5$ and 0–1 $R^6$;

2-imidazolidon-4-yl, substituted with 0–1 $R^5$ and 0–1 $R^6$;

or

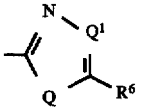 or 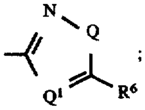 ;

Q is O, S or NH;

$Q^1$ is $CR^5$ or N;

$R^2$ is selected from:

$R^1$;

—$CH_2$—X—$Y^1$—$Z^1$;
hydrogen;
($C_3$–$C_6$ cycloalkyl)methyl substituted with 0–2 $R^7$;
$C_1$–$C_6$ alkyl substituted with 0–2 $R^7$;
$C_3$–$C_6$ alkenyl substituted with 0–2 $R^7$;
$C_3$–$C_6$ alkynyl substituted with 0–2 $R^7$;
benzyl substituted with 0–5 $R^9$;
2-naphthylmethyl substituted with 0–2 $R^9$;
2- or 3-thienylmethyl, 2- or 3-furanylmethyl, or 2-, 3- or 4-pyridinylmethyl, said thienyl, furanyl or pyridinyl being substituted with 0–2 $R^9$; or
5- or 6-indazolylmethyl, 5-benzotriazolylmethyl, 5-benzoxazolonylmethyl, 6-benzoxazolonylmethyl, 5-benzimidazolylmethyl, 5-benzoxazolylmethyl, or 5-benzisoxazolylmethyl, said indazolyl, benzimidazolyl, benzoxazolyl and benzisoxazolyl being substituted with 0–1 $R^{10}$;

$Y^1$ is selected from:
—$(CH_2)_nO(CH_2)_m$—,
—$(CH_2)_nS(CH_2)_m$—,
—$(CH_2)_nNH(CH_2)_m$—,
—$(CH_2)_nC(=O)$ $NH(CH_2)_m$—,
—$(CH_2)_nSO_2NH(CH_2)_m$—
—$(CH_2)_mNHC(=O)(CH_2)_m$—,
$(CH_2)_nNHCO_2(CH_2)_m$—,
—$(CH_2)_mOC(=O)NH(CH_2)_m$—,
—$(CH_2)_nNHC(=O)NH(CH_2)_m$—, or
—$(CH_2)_nC(=NH)NH(CH_2)_m$—;

$Z^1$ is selected from:
hydrogen;
$C_1$–$C_5$ alkyl substituted with 0–2 $R^7$;
$C_2$–$C_5$ alkenyl substituted with 0–2 $R^7$;
$C_2$–$C_5$ alkynyl substituted with 0–2 $R^7$;
$C_3$–$C_6$ cycloalkyl substituted with 0–2 $R^7$;
aryl substituted with 0–2 $R^9$, wherein said aryl group is phenyl or naphthyl;
2-, 3-, or 4-pyridinyl, substituted with 0–1 $R^5$ and 0–1 $R^6$;
2-pyrimidinyl, substituted with 0–1 $R^5$ and 0–1 $R^6$;
2-pyrazinyl, substituted with 0–1 $R^5$ and 0–1 $R^6$;
4-pyrimidon-2-yl- or 2-pyrimidon-4-yl, substituted with 0–1 $R^5$ and 0–1 $R^6$;
6H-1,3,4-thiadiazin-2-yl, substituted with 0–1 $R^5$ and 0–1 $R^6$;
5-uracilyl, substituted with 0–1 $R^5$ and 0–1 $R^6$;
2-, 3-, or 4-quinolinyl, substituted with 0–1 $R^5$ and 0–1 $R^6$;
1-, 3-, or 4-isoquinolinyl, substituted with 0–1 $R^5$ and 0–1 $R^6$;
5- or 6-coumarinyl, substituted with 0–1 $R^5$ and 0–1 $R^6$;
3-tetrahydrofuranyl, substituted with 0–1 $R^5$ and 0–1 $R^6$;
2- or 3-pyrrolidinyl, substituted with 0–1 $R^5$ and 0–1 $R^6$;
2-imidazolidon-4-yl, substituted with 0–1 $R^5$ and 0–1 $R^6$;
or

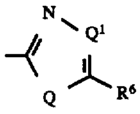 or 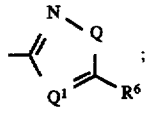 ;

$R^3$ and $R^4$ are independently selected from:
benzyl, 4-fluorobenzyl, 2-pyrrolylmethyl, 3-methoxybenzyl, 4-methoxybenzyl, ethyl, isobutyl, cyclohexylmethyl, n-hexyl, 4-nitrobenzyl, 4-aminobenzyl, 3-hydroxybenzyl, 4-hydroxybenzyl, 4-benzyloxybenzyl, 4-thiomethylbenzyl, 2-thienylmethyl, 3-thienylmethyl, 2-thiazolylmethyl, 4-pyridylmethyl 3,4-methylenedioxybenzyl, 3,4 -ethylenedioxybenzyl, 1,4-benzoxazin-6-yl-methyl, 4-N,N-dimethylaminobenzyl or 2-naphthylmethyl;

$R^5$ and $R^6$ are independently selected from:
hydrogen, halogen, —CN, —$NO_2$, —OH, —$CO_2R^8$, —$CONHR^8$, —$NR^{11}R^{12}$, —$SR^8$, —$SO_mR^{13}$, $C_1$–$C_4$ haloalkyl, $C_2$–$C_4$ haloalkoxy, $C_1$–$C_4$ alkoxy, $C_1$–$C_6$ alkyl, $C_2$–$C_4$ alkenyl, $C_2$–$C_4$ alkynyl, phenoxy, $C_3$–$C_{10}$ cycloalkyl, $C_3$–$C_6$ cycloalkylmethyl, $C_7$–$C_{10}$ arylalkyl wherein said aryl group is phenyl or naphthyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, —CN, —$NO_2$, —$NR^{11}R^{12}$, —$CF_3$, $C_1$–$C_4$ alkyl, $C_1$–$C_4$ alkoxy or —OH, or
alternatively, $R^5$ and $R^6$, when substituents on adjacent carbons, can be taken together with the carbon atoms to which they are attached to form a 5–6 membered fused carbocyclic or heterocyclic ring system wherein said fused heterocyclic ring is selected from pyridine, thiophene, pyrimidine, pyrazine, or pyridazine, said carbocyclic or heterocyclic ring system being optionally substituted with 1–3 groups independently selected from: Cl, F, Br, —CN, —$NO_2$, —$CF_3$, —$CO_2R^8$, —$COR^8$, —$OCOR^8$, —$NR^{11}R^{12}$, —$CONHR^8$, $C_1$–$C_4$ alkyl, $C_1$–$C_4$ alkoxy or —OH;

$R^7$ is selected from: hydrogen, halogen, —CN, —$NO_2$, —$OR^8$, $C_1$–$C_4$ haloalkyl, $C_2$–$C_4$ haloalkoxy, —$CO_2R^8$, —$COR^8$, —$CONHR^8$, —$NR^{11}R^{12}$, —$OCOR^8$, $C_1$–$C_6$ alkyl, phenyl substituted with 0–2 $R^{10}$, or
a 5- or 6-membered heterocycle selected from pyridinyl, furanyl, thienyl, pyrrolyl, pyrazolyl, imidazolyl, indolyl, oxazolidinyl, thiazolyl, 1,3,4-thiadiazolyl, oxazolyl, or 1,3,4-oxadiazolyl heteroatoms independently selected from oxygen, nitrogen;

$R^8$ is hydrogen, $C_1$–$C_4$ alkyl, phenyl substituted with 0–2 $R^{10}$, or a 5- or 6-membered heterocycle selected from pyridinyl, furanyl, thienyl, pyrrolyl, pyrazolyl, imidazolyl indolyl, oxazolidinyl, thiazolyl, 1,3,4-thiadiazolyl, oxazolyl, or 1,3,4-oxadiazoyl heteroatoms independently selected from oxygen, nitrogen;

$R^9$ is selected from: $C_1$–$C_3$ alkyl, $OR^8$, $NR^{11}R^{12}$, hydroxymethyl, CN, F, Cl, Br, $CF_3$, —$CO_2R^8$, —$COR^8$, —$CONHR^{11}$, —CH(NOH), —C(=NOH)$CH_3$, —C(=NOH)$NH_2$, —NHC(=O)$NHR^{11}$, —NHC(O)$OR^{11}$, —$COH(R^8)_2$, methylenedioxy, ethylenedioxy, phenyl substituted with 0–2 $R^{10}$, or
a 5- or 6-membered heterocycle selected from pyridinyl, furanyl, thienyl, pyrrolyl, pyrazolyl, imidazolyl, indolyl, oxazolidinyl, thiazolyl, 1,3,4-thiadiazolyl, oxazolyl, or 1,3,4-oxadiazolyl heteroatoms independently selected from oxygen, nitrogen;

$R^{10}$ is selected from: $C_1$–$C_3$ alkyl, $OR^8$, $NR^{11}R^{12}$, F, Cl, Br, —$COR^8$, —$CO_2R^8$, —$CH_2OR^8$, or —$CH_2C(=O)R^8$;

$R^{11}$ is selected from: hydrogen or $C_1$–$C_4$ alkyl;

$R^{12}$ is selected from: hydrogen, $C_1$–$C_4$ alkyl, glycinyl, alanyl, alanyl-alanyl, phenylglycinyl, phenylalanyl or N-methylglycinyl, N,N-dimethylglycinyl;

$R^{13}$ is selected from: hydrogen, phenyl, benzyl, $C_1$–$C_6$ alkyl or $C_3$–$C_6$ alkoxyalkyl.

2. A compound of claim 1, of formula (II):

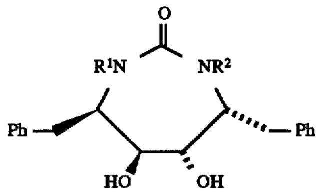

(II)

or a pharmaceutically acceptable salt form thereof, wherein:

$R^1$ is

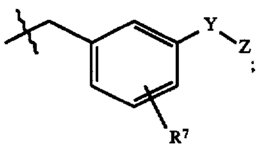

;

Y is selected from:

—$(CH_2)_n$O—,
—$(CH_2)_n$S—,
—$(CH_2)_n$NH—,
—$(CH_2)_n$CONH—,
—$(CH_2)_n$$SO_2$NH—
—$(CH_2)_n$OCONH—,
—$(CH_2)_n$NHCONH—,
—$(CH_2)_n$C(=NH) NH—;

n is 0–2;

m is 1–2;

Z is a heterocycle selected from:

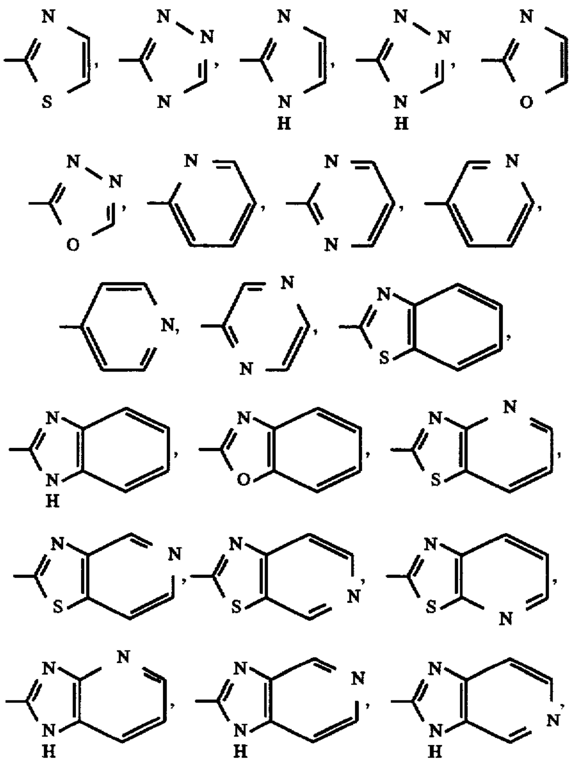

-continued

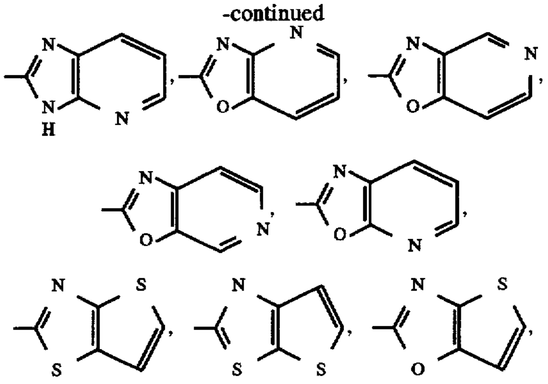

and

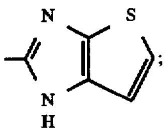

;

said heterocycle being substituted with 0–1 $R^5$ and 0–1 $R^6$;

$R^2$ is selected from:

$R^1$, —$CH_2$—X—$Y^1$—Z, cyclopropylmethyl, allyl, 3,3-dimethylallyl, 2-methylallyl, n-propyl, 3-methylbutyl, 2-methylpropyl, n-butyl, n-pentyl, iso-pentyl, 4,4,4-trifluorobutyl, 3-methoxypropyl, benzyl, 2-naphthylmethyl, 3-methoxybenzyl, 4-methoxybenzyl, 3-hydroxybenzyl, 4-hydroxybenzyl, 3-hydroxymethylbenzyl, 4-hydroxymethylbenzyl, 3-(2-hydroxy-isopropyl) benzyl, 3 -(hydroxypropyl)benzyl, 3-(1-hydroxy) ethylbenzyl, 3,5-dimethoxybenzyl, 3-nitrobenzyl, 3-acetylbenzyl, 3-cyanobenzyl, 3-aminobenzyl, 4-aminobenzyl, 3-N-ethylaminobenzyl, 3-N-butylaminobenzyl, 3-N,N-dimethylaminobenzyl, 3-N-propylaminobenzyl, 3-N,N-dipropylaminobenzyl, 3-N-methylaminobenzyl, 4-N-methylaminobenzyl, 4-N-ehtylaminobenzyl, 4-N,N-dimethylaminobenzyl, 4-N-butylaminobenzyl, 3-(2-pyridylmethyl) aminobenzyl, 3-(carboethoxymethyl)aminobenzyl, 3-(ethoxycarbonyl)aminobenzyl, 3-amino-4-fluorobenzyl, 4-fluorobenzyl, 4-chlorobenzyl, 3-azido-4-fluoro-benzyl, 3-trifluorobenzyl, 2,4-difluorobenzyl, 3-formaldoximebenzyl, cyclopentylmethyl, 3-carbomethoxybenzyl, 3-carboxybenzyl, 3-N-methylaminocarbonylbenzyl, 3-glycylaminobenzyl, 3-N,N-dimethylaminocarbonylbenzyl, 3-N,N-diethylaminobenzyl, 3-alanylaminobenzyl, 3-(L-alanyl-L-alanyl)aminobenzyl, 3-phenylalanylaminobenzyl, 3-(N-methylglycyl) aminobenzyl, 3-($H_2$NC(=NOH))benzyl, 3-($CH_3$C(=NOH))benzyl, 3-(2-pyridyl)benzyl, 5-benzimidazolylmethyl, 5-benzotriazolylmethyl, 5-indazolylmethyl, 6-indazolylmethyl, 2-amino-5-benzoxazolylmethyl, 3-amino-5-benzisoxazolylmethyl, 3-amino-5-indazolylmethyl, 3-methylamino-5-indazolylmethyl, 3-ethylamino-5-indazolylmethyl, 3-methyl-5-indazolylmethyl, 3-methoxy-5-indazolylmethyl, 3-chloro-5-indazolylmethyl, 3,4-methylenedioxybenzyl, 3,4-ethylenedioxybenzyl, 3,4-dihydroxybenzyl, 2-pyridinylmethyl, 2-furanylmethyl, 3-furanylmethyl, 5-bromo-3-furanylmethyl, 1-phenyl-4-pyrazoylmethyl, 3-(1-pyrazolyl)benzyl, 2-thienylmethyl, 3-pyridinylmethyl, 2-pyridinylethyl, 3-pyridinylethyl, 4-pyridinylethyl, 6-hydroxymethyl-3-pyridyl-methyl, 6-chloro-3-pyridyl-methyl, 5-benzoxazolylmethyl, 5-thiazolylmethyl, 5-thiazolylethyl 2-methyl-4-thiazolylmethyl or 3-thienylmethyl;

$Y^1$ is selected from:

$-(CH_2)_nO(CH_2)_m-$, $-(CH_2)_nS(CH_2)_m-$, $-(CH_2)_nNH(CH_2)_m-$, $-(CH_2)_nCONH(CH_2)_m-$, $-(CH_2)_nSO_2NH(CH_2)_m-$ $-(CH_2)_nOCONH(CH_2)_m-$, $-(CH_2)_nNHCONH(CH_2)_m-$, $-(CH_2)_nC(=NH)NH(CH_2)_m-$;

$R^5$ and $R^6$ are independently selected from: hydrogen, halogen, $NO_2$, CN, $CF_3$, $C_1$–$C_4$ alkoxy, $C_1$–$C_6$ alkyl, or phenyl, said phenyl being optionally substituted with 1–3 groups selected independently from: Cl, F, Br, CN, $NO_2$, $CF_3$, $OCH_3$ or OH;

$R^7$ is selected from: hydrogen, halogen, —CN, $-NO_2$, —OH, $CF_3$, $OCH_3$, $CO_2H$, $CO_2R^8$, $COR^8$ or $C_1$–$C_6$ alkyl;

$R^8$ is H or $C_1$–$C_4$ alkyl.

3. A compound of claim 2, or a pharmaceutically acceptable salt form thereof, wherein:

$R^1$ is

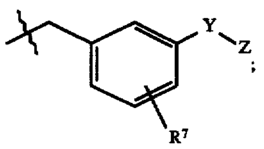

Y is $-(CH_2)_nO-$ or $-(CH_2)_nCONH-$;

n is 0;

m is 1–2;

Z is a heterocycle selected from:

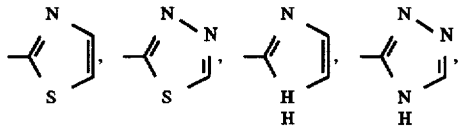

,

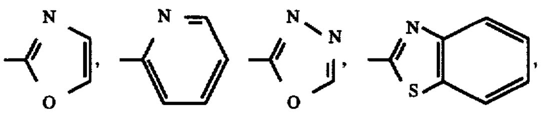

,

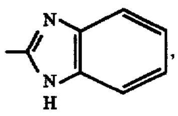

, and

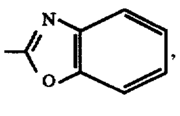

, said heterocycle substituted with 0–1 $R^5$ and 0–1 $R^6$;

$R^2$ is selected from:

$R^1$, $-CH_2-X-y^1-Z$, cyclopropylmethyl, 3,3-dimethylallyl, 2-methylallyl, 3-methylbutyl, 2-methylpropyl, n-butyl, n-pentyl, iso-pentyl, 4,4,4-trifluorobutyl, 3-methoxypropyl, benzyl, 2-naphthylmethyl, 3-methoxybenzyl, 4-methoxybenzyl, 3-hydroxybenzyl, 4-hydroxybenzyl, 3-hydroxymethylbenzyl, 4-hydroxymethylbenzyl, 3-(2-hydroxy-isopropyl) benzyl, 3-(hydroxylpropyl)benzyl, 3-(1-hydroxy) ethylbenzyl, 3-acetylbenzyl, 3-cyanobenzyl, 3-aminobenzyl, 4-aminobenzyl, 3-N-ethylaminobenzyl, 3-N-butylaminobenzyl, 3-N,N-dimethylaminobenzyl, 3-N-propylaminobenzyl, 3-N,N-dipropylaminobenzyl, 3-N-methylaminobenzyl, 4-N-methylaminobenzyl, 4-N-ethylaminobenzyl, 4-N,N-dimethylaminobenzyl, 4-N-butylaminobenzyl, 3-(2-pyridylmethyl) aminobenzyl, 3-(carboethoxymethyl)aminobenzyl, 3-(ethoxycarbonyl)aminobenzyl, 3-amino-4-fluorobenzyl, 4-fluorobenzyl, 4-chlorobenzyl, 3-azido-4-fluoro-benzyl, 3-trifluorobenzyl, 2,4-difluorobenzyl, 3-formaldoximebenzyl, cyclopentylmethyl, 3-carbomethoxybenzyl, 3-carboxybenzyl, 3-N-methylaminocarbonylbenzyl, 3-glycylaminobenzyl, 3-N,N-dimethylaminocarbonylbenzyl, 3-N,N-diethylaminobenzyl, 3-alanylaminobenzyl, 3-(L-alanyl-L-alanyl)aminobenzyl, 3-phenylalanylaminobenzyl, 3-(N-methylglycyl) aminobenzyl, 3-($H_2NC(=NOH)$)benzyl, 3-($CH_3C(=NOH)$)benzyl, 3-(2-pyridyl)benzyl, 5-benzimidazolylmethyl, 5-benzotriazolylmethyl, 5-indazolylmethyl, 6-indazolylmethyl, 2-amino-5-benzoxazolylmethyl, 3-amino-5-benzisoxazolylmethyl, 3-amino-5-indazolylmethyl, 3-methylamino-5-indazolylmethyl, 3-ethylamino-5-indazolylmethyl, 3-methyl-5-indazolylmethyl, 3-methoxy-5-indazolylmethyl, 3-chloro-5-indazolylmethyl, 3,4-methylenedioxybenzyl, 3,4-ethylenedioxybenzyl, 3,4-dihydroxybenzyl, 2-pyridinylmethyl, 2-furanylmethyl, 3-furanylmethyl, 5-bromo-3-furanylmethyl, 1-phenyl-4-pyrazoylmethyl, 3-(1 -pyrazolyl)benzyl, 2-thienylmethyl, 3-pyridinylmethyl, 2-pyridinylethyl, 3-pyridinylethyl, 4-pyridinylethyl, 6-hydroxymethyl-3-pyridyl-methyl, 6-chloro-3-pyridyl-methyl, 5-benzoxazolylmethyl, 5-thiazolylmethyl, 5-thiazolylethyl 2-methyl-4-thiazolylmethyl or 3-thienylmethyl;

$Y^1$ is selected from:

$-(CH_2)_nO(CH_2)_m-$, $-(CH_2)_nCONH(CH_2)_m-$;

$R^5$ and $R^6$ are independently selected from: halogen, $NO_2$, CN, $CF_3$, $C_1$–$C_6$ alkyl, or phenyl, said phenyl being optionally substituted with 1–3 groups independently selected from: Cl, F, Br, CN, $NO_2$, $CF_3$, $OCH_3$ or OH; and $R^7$ is selected from: hydrogen, halogen, —CN, $-NO_2$, —OH, $CF_3$, $OCH_3$, or $C_1$–$C_6$ alkyl.

4. A compound of claim 3, or a pharmaceutically acceptable salt form thereof, wherein:

$R^1$ is

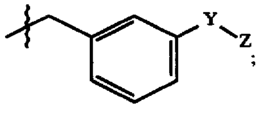

Y is —CONH—;

Z is selected from:

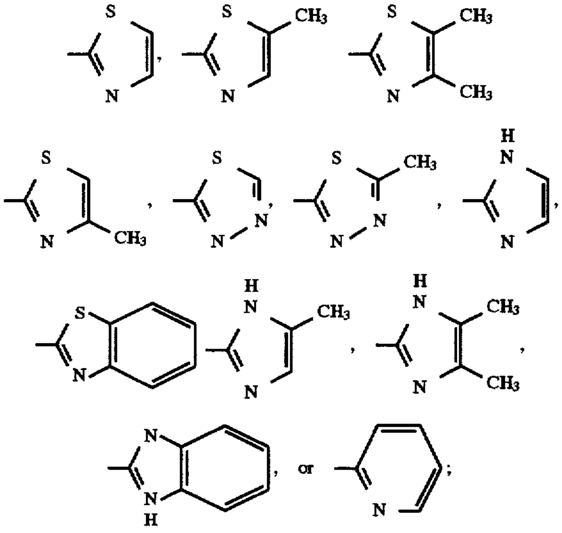

$R^2$ is selected from:

$R^1$, cyclopropylmethyl, 3,3-dimethylallyl, 2-methylallyl, 3-methylbutyl, 2-methylpropyl, n-butyl, n-pentyl, iso-pentyl, 3-methoxypropyl, benzyl, 3-(2-hydroxy-isopropyl)benzyl, 3-acetylbenzyl, 3-aminobenzyl, 4-aminobenzyl, 3-N-ethylaminobenzyl, 3—N,N-dimethylaminobenzyl, 3-N-methylaminobenzyl, 4-N-methylaminobenzyl, 3-hydroxymethylbenzyl, 4-hydroxymethylbenzyl, 2-naphthylmethyl, 3-(2-pyridylmethyl)aminobenzyl, 3-amino-4-fluoro-benzyl, 4-fluorobenzyl, 4-chlorobenzyl, 3-trifluorobenzyl, 3-glycylaminobenzyl, 3-alanylaminobenzyl, 3-(L-alanyl-L-alanyl)aminobenzyl, 3-phenylalanylaminobenzyl, 3-(N-methylglycyl)aminobenzyl, 3-(2-pyridyl)benzyl, 5-indazolylmethyl, 3-amino-5-indazolylmethyl, 3-methylamino-5-indazolylmethyl, 3-methyl-5-indazolylmethyl, 3,4-methylenedioxybenzyl, 3,4-ethylenedioxybenzyl, 3-furanylmethyl, 3-(1-pyrazolyl)benzyl, 3-pyridinylmethyl or 3-thienylmethyl.

5. A compound of claim 1, or a pharmaceutically acceptable salt form thereof, selected from:

the compound of formula (I) wherein $R^3$ and $R^4$ are isobutyl, $R^1$ and $R^2$ are 3-(2-thiazolylaminocarbonyl)phenylmethyl;

the compound of formula (I) wherein $R^3$ and $R^4$ are 4-fluorobenzyl, $R^1$ and $R^2$ are 3-(2-thiazolylaminocarbonyl)phenylmethyl;

the compound of formula (I) wherein $R^3$ and $R^4$ are 3-methoxybenzyl, $R^1$ and $R^2$ are 3-(2-thiazolylaminocarbonyl)phenylmethyl;

the compound of formula (I) wherein $R^3$ and $R^4$ are 3-methoxybenzyl, $R^1$ is cyclopropylmethyl and $R^2$ is (2-thiazolylaminocarbonyl)phenylmethyl;

the compound of formula (I) wherein $R^3$ and $R^4$ are 4-methoxybenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ is benzyl and $R^2$ is (2-thiazolylaminocarbonyl)phenylmethyl;

the compound of formula (I) wherein $R^3$ and $R^4$ are 4-methoxybenzyl, $R^1$2-naphthylmethyl and $R^2$ is (2-thiazolylaminocarbonyl)phenylmethyl;

the compound of formula (I) wherein $R^3$ and $R^4$ are 4-hydroxybenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ is benzyl and $R^2$ is (2-thiazolylaminocarbonyl)phenylmethyl;

the compound of formula (I) wherein $R^3$ and $R^4$ are 4-(2-morpholinylethoxy)benzyl, $R^1$ and $R^2$ are 3-(2-thiazolylaminocarbonyl)phenylmethyl;

the compound of formula (I) wherein $R^3$ and $R^4$ are 4-methylthiobenzyl, $R^1$ and $R^2$ are 3-(2-thiazolylaminocarbonyl)phenylmethyl;

the compound of formula (I) wherein $R^3$ and $R^4$ are 4-methoxybenzyl, $R^1$ and $R^2$ are 3-(2-imidazolylaminocarbonyl)phenylmethyl;

the compound of formula (I) wherein $R^3$ and $R^4$ are 4-methoxybenzyl, $R^1$ and $R^2$ are 3-(2-benzothiazolylaminocarbonyl)phenylmethyl;

the compound of formula (I) wherein $R^3$ and $R^4$ are isobutyl, $R^1$ and $R^2$ are 3-(2-imidazolylaminocarbonyl)phenylmethyl;

the compound of formula (I) wherein $R^3$ and $R^4$ are 4-fluorobenzyl, $R^1$ and $R^2$ are 3-(2-imidazolylaminocarbonyl)phenylmethyl;

the compound of formula (I) wherein $R^3$ and $R^4$ are 3-methoxybenzyl, $R^1$ and $R^2$ are 3-(2-imidazolylaminocarbonyl)phenylmethyl;

the compound of formula (I) wherein $R^3$ and $R^4$ are 3-methoxybenzyl, $R^1$ is cyclopropylmethyl and $R^2$ is (2-imidazolylaminocarbonyl)phenylmethyl;

the compound of formula (I) wherein $R^3$ and $R^4$ are 4-methoxybenzyl, $R^1$ is benzyl and $R^2$ is (2-imidazolylaminocarbonyl)phenylmethyl;

the compound of formula (I) wherein $R^3$ and $R^4$ are 4-methoxybenzyl, $R^1$2-naphthylmethyl and $R^2$ is (2-imidazolylaminocarbonyl)phenylmethyl;

the compound of formula (I) wherein $R^3$ and $R^4$ are 4-hydroxybenzyl, $R^1$ and $R^2$ are 3-(2-imidazolylaminocarbonyl)phenylmethyl;

the compound of formula (I) wherein $R^3$ and $R^4$ are 4-(2-morpholinylethoxy)benzyl, $R^1$ and $R^2$ are 3-(2-imidazolylaminocarbonyl)phenylmethyl;

the compound of formula (I) wherein $R^3$ and $R^4$ are 4-methylthiobenzyl, $R^1$ and $R^2$ are 3-(2-imidazolylaminocarbonyl)phenylmethyl.

6. A compound of claim 2, or a pharmaceutically acceptable salt form thereof, selected from:

the compound of formula (II) wherein $R^1$ is 3-(2-thiazolylaminocarbonyl)phenylmethyl and $R^2$ is 3-(2-thiazolylaminocarbonyl)phenylmethyl;

the compound of formula (II) wherein $R^1$ is 3-(4-methyl-2-thiazolylaminocarbonyl)phenylmethyl and $R^2$ is 3-(4-methyl-2-thiazolylaminocarbonyl)phenylmethyl;

the compound of formula (II) wherein $R^1$ is 3-(1,3,4-thiadiazol-2-ylaminocarbonyl)phenylmethyl and $R^2$ is 3-(1,3,4-thiadiazol-2-ylaminocarbonyl)phenylmethyl;

the compound of formula (II) wherein $R^1$ is 3-(5-methyl-1,3,4-thiadiazol-2-ylaminocarbonyl)phenylmethyl and $R^2$ is 3-(5-methyl-1,3,4-thiadiazol-2-ylaminocarbonyl)phenylmethyl;

the compound of formula (II) wherein $R^1$ is 3-(5-t-butyl-1,3,4-thiadiazol-2-ylaminocarbonyl)phenylmethyl and $R^2$ is 3-(5-t-butyl-1,3,4-thiadiazol-2-ylaminocarbonyl)phenylmethyl;

the compound of formula (II) wherein $R^1$ is 3-(5-methyl-2-thiazolylaminocarbonyl)phenylmethyl and $R^2$ is 3-(5-methyl-2-thiazolylaminocarbonyl)phenylmethyl;

the compound of formula (II) wherein $R^1$ is 3-(4,5-dimethyl-2-thiazolylaminocarbonyl)phenylmethyl and $R^2$ is 3-(4,5-dimethyl-2-thiazolylaminocarbonyl) phenylmethyl;

the compound of formula (II) wherein $R^1$ is 3-(2-imidazolylaminocarbonyl)phenylmethyl and $R^2$ is 3-(2-imidazolylaminocarbonyl)phenylmethyl;

the compound of formula (II) wherein $R^1$ is 3-(2-pyridylaminocarbonyl)phenylmethyl and $R^2$ is 3-(2-pyridylaminocarbonyl)phenylmethyl;

the compound of formula (II) wherein $R^1$ is 3-(2-benzothiazolylaminocarbonyl)phenylmethyl and $R^2$ is 3-(2-benzothiazolylaminocarbonyl)phenylmethyl;

the compound of formula (II) wherein $R^1$ is 3-(2-benzimidazolylaminocarbonyl)phenylmethyl and $R^2$ is 3-(2-benzimidazolylaminocarbonyl)phenylmethyl;

the compound of formula (II) wherein $R^1$ is 3-(2-thiazolyloxy)phenylmethyl and $R^2$ is 3-(2-thiazolyloxy)phenylmethyl;

the compound of formula (II) wherein $R^1$ is 3-(2-pyridinyloxy)phenylmethyl and $R^2$ is 3-(2-pyridinyloxy)phenylmethyl;

the compound of formula (II) wherein $R^1$ is 3-[(3-methyl-2-pyridinyl)aminocarbonyl]phenylmethyl and $R^2$ is 3-[(3-methyl-2-pyridinyl)aminocarbonyl]phenylmethyl;

the compound of formula (II) wherein $R^1$ is 3-[(4-methyl-2-pyridinyl)aminocarbonyl]phenylmethyl and $R^2$ is 3-[(4-methyl-2-pyridinyl)aminocarbonyl]phenylmethyl;

the compound of formula (II) wherein $R^1$ is 3-[(5-methyl-2-pyridinyl)aminocarbonyl]phenylmethyl and $R^2$ is 3-[(5-methyl-2-pyridinyl)aminocarbonyl]phenylmethyl;

the compound of formula (II) wherein $R^1$ is 3-[(6-methyl-2-pyridinyl)aminocarbonyl]phenylmethyl and $R^2$ is 3-[(6-methyl-2-pyridinyl)aminocarbonyl]phenylmethyl;

the compound of formula (II) wherein $R^1$ is cyclopropylmethyl and $R^2$ is 3-(2-thiazolylaminocarbonyl) phenylmethyl;

the compound of formula (II) wherein $R^1$ is n-butyl and $R^2$ is 3-(2-thiazolylaminocarbonyl)phenylmethyl;

the compound of formula (II) wherein $R^1$ is benzyl and $R^2$ is 3-(2-thiazolylaminocarbonyl)phenylmethyl;

the compound of formula (II) wherein $R^1$ is 2-naphthylmethyl and $R^2$ is 3-(2-thiazolylaminocarbonyl)phenylmethyl;

the compound of formula (II) wherein $R^1$ is (3-n-butylaminobenzyl and $R^2$ is 3-(2-thiazolylaminocarbonyl)phenylmethyl;

the compound of formula (II) wherein $R^1$ is 3-aminobenzyl and $R^2$ is 3-(2-thiazolylaminocarbonyl) phenylmethyl;

the compound of formula (II) wherein $R^1$ is 4-aminobenzyl and $R^2$ is 3-(2-thiazolylaminocarbonyl) phenylmethyl;

the compound of formula (II) wherein $R^1$ is 4-N-methylaminobenzyl and $R^2$ is 3-(2-thiazolylaminocarbonyl)phenylmethyl;

the compound of formula (II) wherein $R^1$ is 3-N-methylaminobenzyl and $R^2$ is 3-(2-thiazolylaminocarbonyl)phenylmethyl;

the compound of formula (II) wherein $R^1$ is 3-N-ethylaminobenzyl and $R^2$ is 3-(2-thiazolylaminocarbonyl)phenylmethyl;

the compound of formula (II) wherein $R^1$ is 3—N,N-dimethylaminobenzyl and $R^2$ is 3-(2-thiazolylaminocarbonyl)phenylmethyl;

the compound of formula (II) wherein $R^1$ is 5-indazolylmethyl and $R^2$ is 3-(2-thiazolylaminocarbonyl)phenylmethyl;

the compound of formula (II) wherein $R^1$ is 3-amino-5-indazolylmethyl and $R^2$ is 3-(2-thiazolylaminocarbonyl)phenylmethyl;

the compound of formula (II) wherein $R^1$ is 3-methyl-5-indazolylmethyl and $R^2$ is 3-(2-thiazolylaminocarbonyl)phenylmethyl;

the compound of formula (II) wherein $R^1$ is 3,4-methylenedioxybenzyl and $R^2$ is 3-(2-thiazolylaminocarbonyl)phenylmethyl;

the compound of formula (II) wherein $R^1$ is 3-pyridinylmethyl and $R^2$ is 3-(2-thiazolylaminocarbonyl)phenylmethyl;

the compound of formula (II) wherein $R^1$ is 3-furanylmethyl and $R^2$ is 3-(2-thiazolylaminocarbonyl)phenylmethyl;

the compound of formula (II) wherein $R^1$ is 3-thienylmethyl and $R^2$ is 3-(2-thiazolylaminocarbonyl)phenylmethyl;

the compound of formula (II) wherein $R^1$ is cyclolpropylmethyl and $R^2$ is 3-(4-methyl-2-thiazolylaminocarbonyl)phenylmethyl the compound of formula (II) wherein $R^1$ is n-butyl and $R^2$ is 3-(4-methyl-2-thiazolylaminocarbonyl) phenylmethyl;

the compound of formula (II) wherein $R^1$ is benzyl and $R^2$ is 3-(4-methyl-2-thiazolylaminocarbonyl) phenylmethyl;

the compound of formula (II) wherein $R^1$ is 2-nalphthylmethyl and $R^2$ is 3-(4-methyl-2-thiazolylaminocarbonyl)phenylmethyl;

the compound of formula (II) wherein $R^1$ is (3-n-butylamino)benzyl and $R^2$ is 3-(4-methyl-2-thiazolylaminocarbonyl)phenylmethyl;

the compound of formula (II) wherein $R^1$ is 3-aminobenzyl and $R^2$ is 3-(4-methyl-2-thiazolylaminocarbonyl)phenylmethyl;

the compound of formula (II) wherein $R^1$ is 4-aminobenzyl and $R^2$ is 3-(4-methyl-2-thiazolylaminocarbonyl)phenylmethyl;

the compound of formula (II) wherein $R^1$ is 4-N-methylaminobenzyl and $R^2$ is 3-(4-methyl-2-thiazolylaminocarbonyl)phenylmethyl;

the compound of formula (II) wherein $R^1$ is 3-N-methylaminobenzyl and $R^2$ is 3-(4-methyl-2-thiazolylaminocarbonyl)phenylmethyl;

the compound of formula (II) wherein $R^1$ is 3-N-ethylaminobenzyl and $R^2$ is 3-(4-methyl-2-thiazolylaminocarbonyl)phenylmethyl;

the compound of formula (II) wherein $R^1$ is 3-N,N-dimethylaminobenzyl and $R^2$ is 3-(4-methyl-2-thiazolylaminocarbonyl)phenylmethyl;

the compound of formula (II) wherein $R^1$ is 5-indazolylmethyl and $R^2$ is 3-(4-methyl-2-thiazolylaminocarbonyl)phenylmethyl;

the compound of formula (II) wherein $R^1$ is 3-amino-5-indazolylmethyl and $R^2$ is 3-(4-methyl-2-thiazolylaminocarbonyl)phenylmethyl;

the compound of formula (II) wherein $R^1$ is 3-methyl-5-indazolylmethyl and $R^2$ is 3-(4-methyl-2-thiazolylaminocarbonyl)phenylmethyl;

the compound of formula (II) wherein $R^1$ is 3,4-methylenedioxybenzyl and $R^2$ is 3-(4-methyl-2-thiazolylaminocarbonyl)phenylmethyl;

the compound of formula (II) wherein $R^1$ is 3-pyridinylmethyl and $R^2$ is 3-(4-methyl-2-thiazolylaminocarbonyl)phenylmethyl;

the compound of formula (II) wherein $R^1$ is 3-furanylmethyl and $R^2$ is 3-(4-methyl-2-thiazolylaminocarbonyl)phenylmethyl;

the compound of formula (II) wherein $R^1$ is 3-thienylmethyl and $R^2$ is 3-(4-methyl-2-thiazolylaminocarbonyl)phenylmethyl;

the compound of formula (II) wherein $R^1$ is cyclopropylmethyl and $R^2$ is 3-(1,3,4-thiadiazol-2-ylaminocarbonyl)phenylmethyl;

the compound of formula (II) wherein $R^1$ is n-butyl and $R^2$ is 3-(1,3,4-thiadiazol-2-ylaminocarbonyl) phenylmethyl;

the compound of formula (II) wherein $R^1$ is benzyl and $R^2$ is 3-(1,3,4-thiadiazol-2-ylaminocarbonyl) phenylmethyl;

the compound of formula (II) wherein $R^1$ is 2-naphthylmethyl and $R^2$ is 3-(1,3,4-thiadiazol-2-ylaminocarbonyl)phenylmethyl;

the compound of formula (II) wherein $R^1$ is (3-n-butylamino)benzyl and $R^2$ is 3-(1,3,4-thiadiazol-2-ylaminocarbonyl)phenylmethyl;

the compound of formula (II) wherein $R^1$ is 3-aminobenzyl and $R^2$ is 3-(1,3,4-thiadiazol-2-ylaminocarbonyl)phenylmethyl;

the compound of formula (II) wherein $R^1$ is 4-aminobenzyl and $R^2$ is 3-(1,3,4-thiadiazol-2-ylaminocarbonyl)phenylmethyl;

the compound of formula (II) wherein $R^1$ is 4-N-methylaminobenzyl and $R^2$ is 3-(1,3,4-thiadiazol-2-ylaminocarbonyl)phenylmethyl;

the compound of formula (II) wherein $R^1$ is 3-N-methylaminobenzyl and $R^2$ is 3-(1,3,4-thiadiazol-2-ylaminocarbonyl)phenylmethyl;

the compound of formula (II) wherein $R^1$ is 3-N-ethylaminobenzyl and $R^2$ is 3-(1,3,4-thiadiazol-2-ylaminocarbonyl)phenylmethyl;

the compound of formula (II) wherein $R^1$ is 3-N,N-dimethylaminobenzyl and $R^2$ is 3-(1,3,4-thiadiazol-2-ylaminocarbonyl)phenylmethyl;

the compound of formula (II) wherein $R^1$ is 5-indazolylmethyl and $R^2$ is 3-(1,3,4-thiadiazol-2-ylaminocarbonyl)phenylmethyl;

the compound of formula (II) wherein $R^1$ is 3-amino-5-indazolylmethyl and $R^2$ is 3-(1,3,4-thiadiazol-2-ylaminocarbonyl)phenylmethyl;

the compound of formula (II) wherein $R^1$ is 3-methyl-5-indazolylmethyl and $R^2$ is 3-(1,3,4-thiadiazol-2-ylaminocarbonyl)phenylmethyl;

the compound of formula (II) wherein $R^1$ is 3,4-methylenedioxybenzyl and $R^2$ is 3-(1,3,4-thiadiazol-2-ylaminocarbonyl)phenylmethyl;

the compound of formula (II) wherein $R^1$ is 3-pyridinylmethyl and $R^2$ is 3-(1,3,4-thiadiazol-2-ylaminocarbonyl)phenylmethyl;

the compound of formula (II) wherein $R^1$ is 3-furanylmethyl and $R^2$ is 3-(1,3,4-thiadiazol-2-ylaminocarbonyl)phenylmethyl;

the compound of formula (II) wherein $R^1$ is 3-thienylmethyl and $R^2$ is 3-(1,3,4-thiadiazol-2-ylaminocarbonyl)phenylmethyl;

the compound of formula (II) wherein $R^1$ is cyclopropylmethyl and $R^2$ is 3-(5-methyl-1,3,4-thiadiazol-2-ylaminocarbonyl)phenylmethyl;

the compound of formula (II) wherein $R^1$ is n-butyl and $R^2$ is 3-(5-methyl-1,3,4-thiadiazol-2-ylaminocarbonyl) phenylmethyl;

the compound of formula (II) wherein $R^1$ is benzyl and $R^2$ is 3-(5-methyl-1,3,4-thiadiazol-2-ylaminocarbonyl) phenylmethyl;

the compound of formula (II) wherein $R^1$ is 2-naphthylmethyl and $R^2$ is 3-(5-methyl-1,3,4-thiadiazol-2-ylaminocarbonyl)phenylmethyl;

the compound of formula (II) wherein $R^1$ is (3-n-butylamino)benzyl and $R^2$ is 3-(5-methyl-1,3,4-thiadiazol-2-ylaminocarbonyl)phenylmethyl;

the compound of formula (II) wherein $R^1$ is 3-aminobenzyl and $R^2$ is 3-(5-methyl-1,3,4-thiadiazol-2-ylaminocarbonyl)phenylmethyl;

the compound of formula (II) wherein $R^1$ is 4-aminobenzyl and $R^2$ is 3-(5-methyl-1,3,4-thiadiazol-2-ylaminocarbonyl)phenylmethyl;

the compound of formula (II) wherein $R^1$ is 4N-methylaminobenzyl and $R^2$ is 3-(5-methyl-1,3,4-thiadiazol-2-ylaminocarbonyl)phenylmethyl;

the compound of formula (II) wherein $R^1$ is 3-N-methylaminobenzyl and $R^2$ is 3-(5-methyl-1,3,4-thiadiazol-2-ylaminocarbonyl)phenylmethyl;

the compound of formula (II) wherein $R^1$ is 3-N-ethylaminobenzyl and $R^2$ is 3-(5-methyl-1,3,4-thiadiazol-2-ylaminocarbonyl)phenylmethyl;

the compound of formula (II) wherein $R^1$ is 3-N,N-dimethylaminobenzyl and $R^2$ is 3-(5-methyl-1,3,4-thiadiazol-2-ylaminocarbonyl)phenylmethyl;

the compound of formula (II) wherein $R^1$ is 5-indazolylmethyl and $R^2$ is 3-(5-methyl-1,3,4-thiadiazol-2-ylaminocarbonyl)phenylmethyl;

the compound of formula (II) wherein $R^1$ is 3-amino-5-indazolylmethyl and $R^2$ is 3-(5-methyl-1,3,4-thiadiazol-2-ylaminocarbonyl)phenylmethyl;

the compound of formula (II) wherein $R^1$ is 3-methyl-5-indazolylmethyl and $R^2$ is 3-(5-methyl-1,3,4-thiadiazol-2-ylaminocarbonyl)phenylmethyl;

the compound of formula (II) wherein $R^1$ is 3,4-methylenedioxybenzyl and $R^2$ is 3-(5-methyl-1,3,4-thiadiazol-2-ylaminocarbonyl)phenylmethyl;

the compound of formula (II) wherein $R^1$ is 3-pyridinylmethyl and $R^2$ is 3-(5-methyl-1,3,4-thiadiazol-2-ylaminocarbonyl)phenylmethyl;

the compound of formula (II) wherein $R^1$ is 3-furanylmethyl and $R^2$ is 3-(5-methyl-1,3,4-thiadiazol-2-ylaminocarbonyl)phenylmethyl;

the compound of formula (II) wherein $R^1$ is 3-thienylmethyl and $R^2$ is 3-(5-methyl-1,3,4-thiadiazol-2-ylaminocarbonyl)phenylmethyl;

the compound of formula (II) wherein $R^1$ is cyclopropylmethyl and $R^2$ is 3-(5-t-butyl-1,3,4-thiadiazol-2-ylaminocarbonyl)phenylmethyl;

the compound of formula (II) wherein $R^1$ is n-butyl and $R^2$ is 3-(5-t-butyl-1,3,4-thiadiazol-2-ylaminocarbonyl) phenylmethyl;

the compound of formula (II) wherein $R^1$ is benzyl and $R^2$ is 3-(5-t-butyl-1,3,4-thiadiazol-2-ylaminocarbonyl) phenylmethyl;

the compound of formula (II) wherein $R^1$ is 2-naphthylmethyl and $R^2$ is 3-(5-t-butyl-1,3,4-thiadiazol-2-ylaminocarbonyl)phenylmethyl;

the compound of formula (II) wherein $R^1$ is n-butylaminobenzyl and $R^2$ is 3-(5-t-butyl-1,3,4-thiadiazol-2-ylaminocarbonyl)phenylmethyl;

the compound of formula (II) wherein $R^1$ is 3-aminobenzyl and $R^2$ is 3-(5-t-butyl-1,3,4-thiadiazol-2-ylaminocarbonyl)phenylmethyl;

the compound of formula (II) wherein $R^1$ is 4-aminobenzyl and $R^2$ is 3-(5-t-butyl-1,3,4-thiadiazol-2-ylaminocarbonyl)phenylmethyl;

the compound of formula (II) wherein $R^1$ is 4-N-methylaminobenzyl and $R^2$ is 3-(5-t-butyl-1,3,4-thiadiazol-2-ylaminocarbonyl)phenylmethyl;

the compound of formula (II) wherein $R^1$ is 3-N-methylaminobenzyl and $R^2$ is 3-(5-t-butyl-1,3,4-thiadiazol-2-ylaminocarbonyl)phenylmethyl;

the compound of formula (II) wherein $R^1$ is 3-N-ethylaminobenzyl and $R^2$ is 3-(5-t-butyl-1,3,4-thiadiazol-2-ylaminocarbonyl)phenylmethyl;

the compound of formula (II) wherein $R^1$ is 3-N,N-dimethylaminobenzyl and $R^2$ is 3-(5-t-butyl-1,3,4-thiadiazol-2-ylaminocarbonyl)phenylmethyl;

the compound of formula (II) wherein $R^1$ is 5-indazolylmethyl and $R^2$ is 3-(5-t-butyl-1,3,4-thiadiazol-2-ylaminocarbonyl)phenylmethyl;

the compound of formula (II) wherein $R^1$ is 3-amino-5-indazolylmethyl and $R^2$ is 3-(5-t-butyl-1,3,4-thiadiazol-2-ylaminocarbonyl)phenylmethyl;

the compound of formula (II) wherein $R^1$ is 3-methyl-5-indazolylmethyl and $R^2$ is 3-(5-t-butyl-1,3,4-thiadiazol-2-ylaminocarbonyl)phenylmethyl;

the compound of formula (II) wherein $R^1$ is 3,4-methylenedioxybenzyl and $R^2$ is 3-(5-t-butyl-1,3,4-thiadiazol-2-ylaminocarbonyl)phenylmethyl;

the compound of formula (II) wherein $R^1$ is 3-pyridinylmethyl and $R^2$ is 3-(5-t-butyl-1,3,4-thiadiazol-2-ylaminocarbonyl)phenylmethyl;

the compound of formula (II) wherein $R^1$ is 3-furanylmethyl and $R^2$ is 3-(5-t-butyl-1,3,4-thiadiazol-2-ylaminocarbonyl)phenylmethyl;

the compound of formula (II) wherein $R^1$ is 3-thienylmethyl and $R^2$ is 3-(5-t-butyl-1,3,4-thiadiazol-2-ylaminocarbonyl)phenylmethyl;

the compound of formula (II) wherein $R^1$ is cyclopropylmethyl and $R^2$ is 3-(5-methyl-2-thiazolylaminocarbonyl)phenylmethyl;

the compound of formula (II) wherein $R^1$ is n-butyl and $R^2$ is 3-(5-methyl-2-thiazolylaminocarbonyl) phenylmethyl;

the compound of formula (II) wherein $R^1$ is benzyl and $R^2$ is 3-(5-methyl-2-thiazolylaminocarbonyl) phenylmethyl;

the compound of formula (II) wherein $R^1$ is 2-naphthylmethyl and $R^2$ is 3-(5-methyl-2-thiazolylaminocarbonyl)phenylmethyl;

the compound of formula (II) wherein $R^1$ is (3-n-butylamino)benzyl and $R^2$ is 3-(5-methyl-2-thiazolylaminocarbonyl)phenylmethyl;

the compound of formula (II) wherein $R^1$ is 3-aminobenzyl and $R^2$ is 3-(5-methyl-2-thiazolylaminocarbonyl)phenylmethyl;

the compound of formula (II) wherein $R^1$ is 4-aminobenzyl and $R^2$ is 3-(5-methyl-2-thiazolylaminocarbonyl)phenylmethyl;

the compound of formula (II) wherein $R^1$ is 4-N-methylaminobenzyl and $R^2$ is 3-(5-methyl-2-thiazolylaminocarbonyl)phenylmethyl;

the compound of formula (II) wherein $R^1$ is 3-N-methylaminobenzyl and $R^2$ is 3-(5-methyl-2-thiazolylaminocarbonyl)phenylmethyl;

the compound of formula (II) wherein $R^1$ is 3-N-ethylaminobenzyl and $R^2$ is 3-(5-methyl-2-thiazolylaminocarbonyl)phenylmethyl;

the compound of formula (II) wherein $R^1$ is 3-N,N-dimethylaminobenzyl and $R^2$ is 3-(5-methyl-2-thiazolylaminocarbonyl)phenylmethyl;

the compound of formula (II) wherein $R^1$ is 5-indazolylmethyl and $R^2$ is 3-(5-methyl-2-thiazolylaminocarbonyl)phenylmethyl;

the compound of formula (II) wherein $R^1$ is 3-amino-5-indazolylmethyl and $R^2$ is 3-(5-methyl-2-thiazolylaminocarbonyl)phenylmethyl;

the compound of formula (II) wherein $R^1$ is 3-methyl-5-indazolylmethyl and $R^2$ is 3-(5-methyl-2-thiazolylaminocarbonyl)phenylmethyl;

the compound of formula (II) wherein $R^1$ is 3,4-methylenedioxybenzyl and $R^2$ is 3-(5-methyl-2-thiazolylaminocarbonyl)phenylmethyl;

the compound of formula (II) wherein $R^1$ is 3-pyridinylmethyl and $R^2$ is 3-(5-methyl-2-thiazolylaminocarbonyl)phenylmethyl;

the compound of formula (II) wherein $R^1$ is 3-furanylmethyl and $R^2$ is 3-(5-methyl-2-thiazolylaminocarbonyl)phenylmethyl;

the compound of formula (II) wherein $R^1$ is 3-thienylmethyl and $R^2$ is 3-(5-methyl-2-thiazolylaminocarbonyl)phenylmethyl;

the compound of formula (II) wherein $R^1$ is cyclopropylmethyl and $R^2$ is 3-(4,5-dimethyl-2-thiazolylaminocarbonyl)phenylmethyl;

the compound of formula (II) wherein $R^1$ is n-butyl and $R^2$ is 3-(4,5-dimethyl-2-thiazolylaminocarbonyl) phenylmethyl;

the compound of formula (II) wherein $R^1$ is benzyl and $R^2$ is 3-(4,5-dimethyl-2-thiazolylaminocarbonyl) phenylmethyl;

the compound of formula (II) wherein $R^1$ is 2-naphthylmethyl and $R^2$ is 3-(4,5-dimethyl-2-thiazolylaminocarbonyl)phenylmethyl;

the compound of formula (II) wherein $R^1$ is n-butylaminobenzyl and $R^2$ is 3-(4,5-dimethyl-2-thiazolylaminocarbonyl)phenylmethyl;

the compound of formula (II) wherein $R^1$ is 3-aminobenzyl and $R^2$ is 3-(4,5-dimethyl-2-thiazolylaminocarbonyl)phenylmethyl;

the compound of formula (II) wherein $R^1$ is 4-aminobenzyl and $R^2$ is 3-(4,5-dimethyl-2-thiazolylaminocarbonyl)phenylmethyl;

the compound of formula (II) wherein $R^1$ is 4-N-methylaminobenzyl and $R^2$ is 3-(4,5-dimethyl-2-thiazolylaminocarbonyl)phenylmethyl;

the compound of formula (II) wherein $R^1$ is 3-N-methylaminobenzyl and $R^2$ is 3-(4,5-dimethyl-2-thiazolylaminocarbonyl)phenylmethyl;

the compound of formula (II) wherein $R^1$ is 3-N-ethylaminobenzyl and $R^2$ is 3-(4,5-dimethyl-2-thiazolylaminocarbonyl)phenylmethyl;

the compound of formula (II) wherein $R^1$ is 3-N,N-dimethylaminobenzyl and $R^2$ is 3-(4,5-dimethyl-2-thiazolylaminocarbonyl)phenylmethyl;

the compound of formula (II) wherein $R^1$ is 5-indazolylmethyl and $R^2$ is 3-(4,5-dimethyl-2-thiazolylaminocarbonyl)phenylmethyl;

the compound of formula (II) wherein $R^1$ is 3-amino-5-indazolylmethyl and $R^2$ is 3-(4,5-dimethyl-2-thiazolylaminocarbonyl)phenylmethyl;

the compound of formula (II) wherein $R^1$ is 3-methyl-5-indazolylmethyl and $R^2$ is 3-(4,5-dimethyl-2-thiazolylaminocarbonyl)phenylmethyl;

the compound of formula (II) wherein $R^1$ is 3,4-methylenedioxybenzyl and $R^2$ is 3-(4,5-dimethyl-2-thiazolylaminocarbonyl)phenylmethyl;

the compound of formula (II) wherein $R^1$ is 3-pyridinylmethyl and $R^2$ is 3-(4,5-dimethyl-2-thiazolylaminocarbonyl)phenylmethyl;

the compound of formula (II) wherein $R^1$ is 3-furanylmethyl and $R^2$ is 3-(4,5-dimethyl-2-thiazolylaminocarbonyl)phenylmethyl;

the compound of formula (II) wherein $R^1$ is 3-thienylmethyl and $R^2$ is 3-(4,5-dimethyl-2-thiazolylaminocarbonyl)phenylmethyl;

the compound of formula (II) wherein $R^1$ is cyclopropylmethyl and $R^2$ is 3-(2-imidazolylaminocarbonyl)phenylmethyl;

the compound of formula (II) wherein $R^1$ is n-butyl and $R^2$ is 3-(2-imidazolylaminocarbonyl)phenylmethyl;

the compound of formula (II) wherein $R^1$ is n-pentyl and $R^2$ is 3-(2-imidazolylaminocarbonyl)phenylmethyl;

the compound of formula (II) wherein $R^1$ is 3-methylbutyl and $R^2$ is 3-(2-imidazolylaminocarbonyl)phenylmethyl;

the compound of formula (II) wherein $R^1$ is 2-methylpropyl and $R^2$ is 3-(2-imidazolylaminocarbonyl)phenylmethyl;

the compound of formula (II) whereran $R^1$ is benzyl and $R^2$ is 3-(2-imidazolylaminocarbonyl)phenylmethyl;

the compound of formula (II) wherein $R^1$ is 2-naphthylmethyl and $R^2$ is 3-(2-imidazolylaminocarbonyl)phenylmethyl;

the compound of formula (II) wherein $R^1$ is (3-n-butylamino)benzyl and $R^2$ is 3-(2-imidazolylaminocarbonyl)phenylmethyl;

the compound of formula (II) whereran $R^1$ is 3-aminobenzyl and $R^2$ is 3-(2-imidazolylaminocarbonyl)phenylmethyl;

the compound of formula (II) whereran $R^1$ is 4-aminobenzyl and $R^2$ is 3-(2-imidazolylaminocarbonyl)phenylmethyl;

the compound of formula (II) wherein $R^1$ is 4-N-methylaminobenzyl and $R^2$ is 3-(2-imidazolylaminocarbonyl)phenylmethyl;

the compound of formula (II) wherein $R^1$ is 3-N-methylaminobenzyl and $R^2$ is 3-(2-imidazolylaminocarbonyl)phenylmethyl;

the compound of formula (II) whereran $R^1$ is 3-N-ethylaminobenzyl and $R^2$ is 3-(2-imidazolylaminocarbonyl)phenylmethyl;

the compound of formula (II) wherein $R^1$ is 3-N,N-dimethylaminobenzyl and $R^2$ is 3-(2-imidazolylaminocarbonyl)phenylmethyl;

the compound of formula (II) wherein $R^1$ is 5-indazolylmethyl and $R^2$ is 3-(2-imidazolylaminocarbonyl)phenylmethyl;

the compound of formula (II) wherein $R^1$ is 3-amino-5-indazolylmethyl and $R^2$ is 3-(2-imidazolylaminocarbonyl)phenylmethyl;

the compound of formula (II) wherein $R^1$ is 3-methyl-5-indazolylmethyl and $R^2$ is 3-(2-imidazolylaminocarbonyl)phenylmethyl;

the compound of formula (II) wherein $R^1$ is 3,4-methylenedioxybenzyl and $R^2$ is 3-(2-imidazolylaminocarbonyl)phenylmethyl;

the compound of formula (II) wherein $R^1$ is 3-pyridinylmethyl and $R^2$ is 3-(2-imidazolylaminocarbonyl)phenylmethyl;

the compound of formula (II) wherein $R^1$ is 3-furanylmethyl and $R^2$ is 3-(2-imidazolylaminocarbonyl)phenylmethyl;

the compound of formula (II) wherein $R^1$ is 3-thienylmethyl and $R^2$ is 3-(2-imidazolylaminocarbonyl)phenylmethyl;

the compound of formula (II) wherein $R^1$ is cyclopropylmethyl and $R^2$ is 3-(2-pyridylaminocarbonyl)phenylmethyl;

the compound of formula (II) wherein $R^1$ is n-butyl and $R^2$ is 3-(2-pyridylaminocarbonyl)phenylmethyl;

the compound of formula (II) wherein $R^1$ is benzyl and $R^2$ is 3-(2-pyridylaminocarbonyl)phenylmethyl;

the compound of formula (II) wherein $R^1$ is 2-naphthylmethyl and $R^2$ is 3-(2-pyridylaminocarbonyl)phenylmethyl;

the compound of formula (II) wherein $R^1$ is (3-n-butylamino)benzyl and $R^2$ is 3-(2-pyridylaminocarbonyl)phenylmethyl;

the compound of formula (II) wherein $R^1$ is 3-aminobenzyl and $R^2$ is 3-(2-pyridylaminocarbonyl)phenylmethyl;

the compound of formula (II) wherein $R^1$ is 4-aminobenzyl and $R^2$ is 3-(2-pyridylaminocarbonyl)phenylmethyl;

the compound of formula (II) wherein $R^1$ is 4-N-methylaminobenzyl and $R^2$ is 3-(2-pyridylaminocarbonyl)phenylmethyl;

the compound of formula (II) wherein $R^1$ is 3-N-methylaminobenzyl and $R^2$ is 3-(2-pyridylaminocarbonyl)phenylmethyl;

the compound of formula (II) wherein $R^1$ is 3-N-ethylaminobenzyl and $R^2$ is 3-(2-pyridylaminocarbonyl)phenylmethyl;

the compound of formula (II) wherein $R^1$ is 3-N,N-dimethylaminobenzyl and $R^2$ is 3-(2-pyridylaminocarbonyl)phenylmethyl;

the compound of formula (II) wherein $R^1$ is 5-indazolylmethyl and $R^2$ is 3-(2-pyridylaminocarbonyl)phenylmethyl;

the compound of formula (II) wherein $R^1$ is 3-amino-5-indazolylmethyl and $R^2$ is 3-(2-pyridylaminocarbonyl) phenylmethyl;

the compound of formula (II) wherein $R^1$ is 3-methyl-5-indazolylmethyl and $R^2$ is 3-(2-pyridylaminocarbonyl) phenylmethyl;

the compound of formula (II) wherein $R^1$ is 3,4-methylenedioxybenzyl and $R^2$ is 3-(2-pyridylaminocarbonyl)phenylmethyl;

the compound of formula (II) wherein $R^1$ is 3-pyridinylmethyl and $R^2$ is 3-(2-pyridylaminocarbonyl)phenylmethyl;

the compound of formula (II) wherein $R^1$ is 3-furanylmethyl and $R^2$ is 3-(2-pyridylaminocarbonyl) phenylmethyl;

the compound of formula (II) wherein $R^1$ is 3-thienylmethyl and $R^2$ is 3-(2-pyridylaminocarbonyl) phenylmethyl;

the compound of formula (II) wherein $R^1$ is cyclopropylmethyl and $R^2$ is 3-(2-benzothiazolylaminocarbonyl) phenylmethyl;

the compound of formula (II) wherein $R^1$ is n-butyl and $R^2$ is 3-(2-benzothiazolylaminocarbonyl) phenylmethyl;

the compound of formula (II) wherein $R^1$ is benzyl and $R^2$ is 3-(2-benzothiazolylaminocarbonyl)phenylmethyl;

the compound of formula (II) wherein $R^1$ is 2-naphthylmethyl and $R^2$ is 3-(2-benzothiazolylaminocarbonyl)phenylmethyl;

the compound of formula (II) wherein $R^1$ is (3-n-butylamino)benzyl and $R^2$ is 3-(2-benzothiazolylaminocarbonyl)phenylmethyl;

the compound of formula (II) wherein $R^1$ is 3-aminobenzyl and $R^2$ is 3-(2-benzothiazolylaminocarbonyl)phenylmethyl;

the compound of formula (II) wherein $R^1$ is 4-aminobenzyl and $R^2$ is 3-(2-benzothiazolylaminocarbonyl)phenylmethyl;

the compound of formula (II) wherein $R^1$ is 4-N-methylaminobenzyl and $R^2$ is 3-(2-benzothiazolylaminocarbonyl)phenylmethyl;

the compound of formula (II) wherein $R^1$ is 3-N-methylaminobenzyl and $R^2$ is 3-(2-benzothiazolylaminocarbonyl)phenylmethyl;

the compound of formula (II) wherein $R^1$ is 3-N-ethylaminobenzyl and $R^2$ is 3-(2-benzothiazolylaminocarbonyl)phenylmethyl;

the compound of formula (II) wherein $R^1$ is 3-N,N-dimethylaminobenzyl and $R^2$ is 3-(2-benzothiazolylaminocarbonyl)phenylmethyl;

the compound of formula (II) wherein $R^1$ is 5-indazolylmethyl and $R^2$ is 3-(2-benzothiazolylaminocarbonyl)phenylmethyl;

the compound of formula (II) wherein $R^1$ is 3-amino-5-indazolylmethyl and $R^2$ is 3-(2-benzothiazolylaminocarbonyl)phenylmethyl;

the compound of formula (II) wherein $R^1$ is 3-methyl-5-indazolylmethyl and $R^2$ is 3-(2-benzothiazolylaminocarbonyl)phenylmethyl;

the compound of formula (II) wherein $R^1$ is 3,4-methylenedioxybenzyl and $R^2$ is 3-(2-benzothiazolylaminocarbonyl)phenylmethyl;

the compound of formula (II) wherein $R^1$ is 3-pyridinylmethyl and $R^2$ is 3-(2-benzothiazolylaminocarbonyl)phenylmethyl;

the compound of formula (II) wherein $R^1$ is 3-furanylmethyl and $R^2$ is 3-(2-benzothiazolylaminocarbonyl)phenylmethyl;

the compound of formula (II) wherein $R^1$ is 3-thienylmethyl and $R^2$ is 3-(2-benzothiazolylaminocarbonyl)phenylmethyl;

the compound of formula (II) wherein $R^1$ is cyclopropylmethyl and $R^2$ is 3-(2-benzimidazolylaminocarbonyl) phenylmethyl;

the compound of formula (II) wherein $R^1$ is n-butyl and $R^2$ is 3-(2-benzimidazolylaminocarbonyl) phenylmethyl;

the compound of formula (II) wherein $R^1$ is benzyl and $R^2$ is 3-(2-benzimidazolylaminocarbonyl)phenylmethyl;

the compound of formula (II) wherein $R^1$ is 2-naphthylmethyl and $R^2$ is 3-(2-benzimidazolylaminocarbonyl)phenylmethyl;

the compound of formula (II) wherein $R^1$ is (3-n-butylamino)benzyl and $R^2$ is 3-(2-benzimidazolylaminocarbonyl)phenylmethyl;

the compound of formula (II) wherein $R^1$ is 3-aminobenzyl and $R^2$ is 3-(2-benzimidazolylaminocarbonyl)phenylmethyl;

the compound of formula (II) wherein $R^1$ is 4-aminobenzyl and $R^2$ is 3-(2-benzimidazolylaminocarbonyl)phenylmethyl;

the compound of formula (II) wherein $R^1$ is 4-N-methylaminobenzyl and $R^2$ is 3-(2-benzimidazolylaminocarbonyl)phenylmethyl the compound of formula (II) wherein $R^1$ is 3-N-methylaminobenzyl and $R^2$ is 3-(2-benzimidazolylaminocarbonyl)phenylmethyl;

the compound of formula (II) wherein $R^1$ is 3-N-ethylaminobenzyl and $R^2$ is 3-(2-benzimidazolylaminocarbonyl)phenylmethyl;

the compound of formula (II) wherein $R^1$ is 3-N,N-dimethylaminobenzyl and $R^2$ is 3-(2-benzimidazolylaminocarbonyl)phenylmethyl;

the compound of formula (II) wherein $R^1$ is 5-indazolylmethyl and $R^2$ is 3-(2-benzimidazolylaminocarbonyl)phenylmethyl;

the compound of formula (II) wherein $R^1$ is 3-amino-5-indazolylmethyl and $R^2$ is 3-(2-benzimidazolylaminocarbonyl)phenylmethyl;

the compound of formula (II) wherein $R^1$ is 3-methyl-5-indazolylmethyl and $R^2$ is 3-(2-benzimidazolylaminocarbonyl)phenylmethyl;

the compound of formula (II) wherein $R^1$ is 3,4-methylenedioxybenzyl and $R^2$ is 3-(2-benzimidazolylaminocarbonyl)phenylmethyl;

the compound of formula (II) wherein $R^1$ is 3-pyridinylmethyl and $R^2$ is 3-(2-benzimidazolylaminocarbonyl)phenylmethyl;

the compound of formula (II) wherein $R^1$ is 3-furanylmethyl and $R^2$ is 3-(2-benzimidazolylaminocarbonyl)phenylmethyl;

the compound of formula (II) wherein $R^1$ is 3-thienylmethyl and $R^2$ is 3-(2-benzimidazolylaminocarbonyl)phenylmethyl;

the compound of formula (II) wherein $R^1$ is cyclopropylmethyl and $R^2$ is 3-(2-thiazolyloxy)phenylmethyl;

the compound of formula (II) wherein $R^1$ is n-butyl and $R^2$ is 3-(2-thiazolyloxy)phenylmethyl;

the compound of formula (II) wherein $R^1$ is benzyl and $R^2$ is 3-(2-thiazolyloxy)phenylmethyl;

the compound of formula (II) wherein $R^1$ is 2-naphthylmethyl and $R^2$ is 3-(2-thiazolyloxy) phenylmethyl;

the compound of formula (II) wherein $R^1$ is (3-n-butylamino)benzyl and $R^2$ is 3-(2-thiazolyloxy) phenylmethyl;

the compound of formula (II) wherein $R^1$ is 3-aminobenzyl and $R^2$ is 3-(2-thiazolyloxy) phenylmethyl;

the compound of formula (II) wherein $R^1$ is 4-aminobenzyl and $R^2$ is 3-(2-thiazolyloxy) phenylmethyl;

the compound of formula (II) wherein $R^1$ is 4-N-methylaminobenzyl and $R^2$ is 3-(2-thiazolyloxy) phenylmethyl;

the compound of formula (II) wherein $R^1$ is 3-N-methylaminobenzyl and $R^2$ is 3-(2-thiazolyloxy) phenylmethyl;

the compound of formula (II) wherein $R^1$ is 3-N- ethylaminobenzyl and $R^2$ is 3-(2-thiazolyloxy) phenylmethyl;

the compound of formula (II) wherein $R^1$ is 3-N,N-dimethylaminobenzyl and $R^2$ is 3-thiazolyloxy) phenylmethyl;

the compound of formula (II) wherein $R^1$ is 5-indazolylmethyl and $R^2$ is 3-thiazolyloxy) phenylmethyl;

the compound of formula (II) wherein $R^1$ is 3-amino-5-indazolylmethyl and $R^2$ is 3-(2-thiazolyloxy) phenylmethyl;

the compound of formula (II) wherein $R^1$ is 3-methyl-5-indazolylmethyl and $R^2$ is 3-(2-thiazolyloxy) phenylmethyl;

the compound of formula (II) wherein $R^1$ is 3,4-methylenedioxybenzyl and $R^2$ is 3-(2-thiazolyloxy) phenylmethyl;

the compound of formula (II) wherein $R^1$ is 3-pyridinylmethyl and $R^2$ is 3-thiazolyloxy) phenylmethyl;

the compound of formula (II) wherein $R^1$ is 3-furanylmethyl and $R^2$ is 3-(2-thiazolyloxy) phenylmethyl;

the compound of formula (II) wherein $R^1$ is 3-thienylmethyl and $R^2$ is 3-(2-thiazolyloxy) phenylmethyl;

the compound of formula (II) wherein $R^1$ is cyclopropylmethyl and $R^2$ is 3-[(3-methyl-2-pyridinyl) aminocarbonyl]phenylmethyl;

the compound of formula (II) wherein $R^1$ is n-butyl and $R^2$ is 3-[(3-methyl-2-pyridinyl)aminocarbonyl] phenylmethyl;

the compound of formula (II) wherein $R^1$ is benzyl and $R^2$ is 3-[(3-methyl-2-pyridinyl)aminocarbonyl] phenylmethyl;

the compound of formula (II) wherein $R^1$ is 2-naphthylmethyl and $R^2$ is 3-[(3-methyl-2-pyridinyl) aminocarbonyl]phenylmethyl;

the compound of formula (II) wherein $R^1$ is (3-n-butylamino)benzyl and $R^2$ is 3-[(3-methyl-2-pyridinyl) aminocarbonyl]phenylmethyl;

the compound of formula (II) wherein $R^1$ is 3-aminobenzyl and $R^2$ is 3-[(3-methyl-2-pyridinyl) aminocarbonyl]phenylmethyl;

the compound of formula (II) wherein $R^1$ is 4-aminobenzyl and $R^2$ is 3-[(3-methyl-2-pyridinyl) aminocarbonyl]phenylmethyl;

the compound of formula (II) wherein $R^1$ is 4-N-methylaminobenzyl and $R^2$ is 3-[(3-methyl-2-pyridinyl)aminocarbonyl]phenylmethyl;

the compound of formula (II) wherein $R^1$ is 3-N-methylaminobenzyl and $R^2$ is 3-[(3-methyl-2-pyridinyl)aminocarbonyl]phenylmethyl;

the compound of formula (II) wherein $R^1$ is 3-N-ethylaminobenzyl and $R^2$ is 3-[(3-methyl-2-pyridinyl) aminocarbonyl]phenylmethyl;

the compound of formula (II) wherein $R^1$ is 3-N,N-dimethylaminobenzyl and $R^2$ is 3-[(3-methyl-2-pyridinyl)aminocarbonyl]phenylmethyl;

the compound of formula (II) wherein $R^1$ is 5-indazolylmethyl and $R^2$ is 3-[(3-methyl-2-pyridinyl) aminocarbonyl]phenylmethyl;

the compound of formula (II) wherein $R^1$ is 3-amino-5-indazolylmethyl and $R^2$ is 3-[(3-methyl-2-pyridinyl) aminocarbonyl]phenylmethyl;

the compound of formula (II) wherein $R^1$ is 3-methyl-5-indazolylmethyl and $R^2$ is 3-[(3-methyl-2-pyridinyl) aminocarbonyl]phenylmethyl;

the compound of formula (II) wherein $R^1$ is 3,4-methylenedioxybenzyl and 3-[(3-methyl-2-pyridinyl) aminocarbonyl]phenylmethyl;

the compound of formula (II) wherein $R^1$ is 3-pyridinylmethyl and $R^2$ is 3-[(3-methyl-2-pyridinyl) aminocarbonyl]phenylmethyl;

the compound of formula (II) wherein $R^1$ is 3-furanylmethyl and $R^2$ is 3-[(3-methyl-2-pyridinyl) aminocarbonyl]phenylmethyl;

the compound of formula (II) wherein $R^1$ is 3-thienylmethyl and $R^2$ is 3-[(3-methyl-2-pyridinyl) aminocarbonyl]phenylmethyl;

the compound of formula (II) wherein $R^1$ is cyclopropylmethyl and $R^2$ is 3-(2-pyridinyloxy)phenylmethyl;

the compound of formula (II) wherein $R^1$ is n-butyl and $R^2$ is 3-(2-pyridinyloxy)phenylmethyl;

the compound of formula (II) wherein $R^1$ is benzyl and $R^2$ is 3-(2-pyridinyloxy)phenylmethyl;

the compound of formula (II) wherein $R^1$ is 2-naphthylmethyl and $R^2$ is 3-(2-pyridinyloxy) phenylmethyl;

the compound of formula (II) wherein $R^1$ is (3-n-butylamino)benzyl and $R^2$ is 3-(2-pyridinyloxy) phenylmethyl;

the compound of formula (II) wherein $R^1$ is 3-aminobenzyl and $R^2$ is 3-(2-pyridinyloxy) phenylmethyl;

the compound of formula (II) wherein $R^1$ is 4-aminobenzyl and $R^2$ is 3-(2-pyridinyloxy) phenylmethyl;

the compound of formula (II) wherein $R^1$ is 4-N-methylaminobenzyl and $R^2$ is 3-(2-pyridinyloxy) phenylmethyl;

the compound of formula (II) wherein $R^1$ is 3-N-methylaminobenzyl and $R^2$ is 3-(2-pyridinyloxy) phenylmethyl;

the compound of formula (II) wherein $R^1$ is 3-N-ethylaminobenzyl and $R^2$ is 3-(2-pyridinyloxy) phenylmethyl;

the compound of formula (II) wherein $R^1$ is 3-N,N-dimethylaminobenzyl and $R^2$ is 3-(2-pyridinyloxy) phenylmethyl;

the compound of formula (II) wherein $R^1$ is 5-indazolylmethyl and $R^2$ is 3-(2-pyridinyloxy) phenylmethyl;

the compound of formula (II) wherein $R^1$ is 3-amino-5-indazolylmethyl and $R^2$ is 3-(2-pyridinyloxy) phenylmethyl;

the compound of formula (II) wherein $R^1$ is 3-methyl-5-indazolylmethyl and $R^2$ is 3-(2-pyridinyloxy) phenylmethyl;

the compound of formula (II) wherein $R^1$ is 3,4-methylenedioxybenzyl and $R^2$ is 3-(2-pyridinyloxy) phenylmethyl;

the compound of formula (II) wherein $R^1$ is 3-pyridinylmethyl and $R^2$ is 3-(2-pyridinyloxy) phenylmethyl;

the compound of formula (II) wherein $R^1$ is 3-furanylmethyl and $R^2$ is 3-(2-pyridinyloxy) phenylmethyl;

the compound of formula (II) wherein $R^1$ is 3-thienylmethyl and $R^2$ is 3-(2-pyridinyloxy) phenylmethyl;

the compound of formula (II) wherein $R^1$ is cyclopropylmethyl and $R^2$ is 3-[(4-methyl-2-pyridinyl) aminocarbonyl]phenylmethyl;

the compound of formula (II) wherein $R^1$ is n-butyl and $R^2$ is 3-[(4-methyl-2-pyridinyl)aminocarbonyl] phenylmethyl;

the compound of formula (II) wherein $R^1$ is benzyl and $R^2$ is 3-[(4-methyl-2-pyridinyl)aminocarbonyl] phenylmethyl;

the compound of formula (II) wherein $R^1$ is 2-naphthylmethyl and $R^2$ is 3-[(4-methyl-2-pyridinyl) aminocarbonyl]phenylmethyl;

the compound of formula (II) wherein $R^1$ is (3-n-butylamino)benzyl and $R^2$ is 3-[(4-methyl-2-pyridinyl) aminocarbonyl]phenylmethyl;

the compound of formula (II) wherein $R^1$ is 3-aminobenzyl and $R^2$ is 3-[(4-methyl-2-pyridinyl) aminocarbonyl]phenylmethyl;

the compound of formula (II) wherein $R^1$ is 4-aminobenzyl and $R^2$ is 3-[(4-methyl-2-pyridinyl) aminocarbonyl]phenylmethyl;

the compound of formula (II) wherein $R^1$ is 4-N-methylaminobenzyl and $R^2$ is 3-[(4-methyl-2-pyridinyl)aminocarbonyl]phenylmethyl;

the compound of formula (II) wherein $R^1$ is 3-N-methylaminobenzyl and $R^2$ is 3-[(4-methyl-2-pyridinyl)aminocarbonyl]phenylmethyl;

the compound of formula (II) wherein $R^1$ is 3-N-ethylaminobenzyl and $R^2$ is 3-[(4-methyl-2-pyridinyl) aminocarbonyl]phenylmethyl;

the compound of formula (II) wherein $R^1$ is 3-N,N-dimethylaminobenzyl and $R^2$ is 3-[(4-methyl-2-pyridinyl)aminocarbonyl]phenylmethyl;

the compound of formula (II) wherein $R^1$ is 5-indazolylmethyl and $R^2$ is 3-[(4-methyl-2-pyridinyl) aminocarbonyl]phenylmethyl;

the compound of formula (II) wherein $R^1$ is 3-amino-5-indazolylmethyl and $R^2$ is 3-[(4-methyl-2-pyridinyl) aminocarbonyl]phenylmethyl;

the compound of formula (II) wherein $R^1$ is 3-methyl-5-indazolylmethyl and $R^2$ is 3-[(4-methyl-2-pyridinyl) aminocarbonyl]phenylmethyl;

the compound of formula (II) wherein $R^1$ is 3,4-methylenedioxybenzyl and $R^2$ is 3-[(4-methyl-2-pyridinyl)aminocarbonyl]phenylmethyl;

the compound of formula (II) wherein $R^1$ is 3-pyridinylmethyl and $R^2$ is 3-[(4-methyl-2-pyridinyl) aminocarbonyl]phenylmethyl;

the compound of formula (II) wherein $R^1$ is 3-furanylmethyl and $R^2$ is 3-[(4-methyl-2-pyridinyl) aminocarbonyl]phenylmethyl;

the compound of formula (II) wherein $R^1$ is 3-thienylmethyl and $R^2$ is 3-[(4-methyl-2-pyridinyl) aminocarbonyl]phenylmethyl;

the compound of formula (II) wherein $R^1$ is cyclopropylmethyl and $R^2$ is 3-[(5-methyl-2-pyridinyl) aminocarbonyl]phenylmethyl;

the compound of formula (II) wherein $R^1$ is n-butyl and $R^2$ is 3-[(5-methyl-2-pyridinyl)aminocarbonyl] phenylmethyl;

the compound of formula (II) wherein $R^1$ is benzyl and $R^2$ is 3-[(5-methyl-2-pyridinyl)aminocarbonyl] phenylmethyl;

the compound of formula (II) wherein $R^1$ is 2-naphthylmethyl and $R^2$ is 3-[(5-methyl-2-pyridinyl) aminocarbonyl]phenylmethyl;

the compound of formula (II) wherein $R^1$ is (3-n-butylamino)benzyl and $R^2$ is 3-[(5-methyl-2-pyridinyl) aminocarbonyl]phenylmethyl;

the compound of formula (II) wherein $R^1$ is 3-aminobenzyl and $R^2$ is 3-[(5-methyl-2-pyridinyl) aminocarbonyl]phenylmethyl;

the compound of formula (II) wherein $R^1$ is 4-aminobenzyl and $R^2$ is 3-[(5-methyl-2-pyridinyl) aminocarbonyl]phenylmethyl;

the compound of formula (II) wherein $R^1$ is 4-N-methylaminobenzyl and $R^2$ is 3-[(5-methyl-2-pyridinyl)aminocarbonyl]phenylmethyl;

the compound of formula (II) wherein $R^1$ is 3-N-methylaminobenzyl and $R^2$ is 3-[(5-methyl-2-pyridinyl)aminocarbonyl]phenylmethyl;

the compound of formula (II) wherein $R^1$ is 3-N-ethylaminobenzyl and $R^2$ is 3-[(5-methyl-2-pyridinyl) aminocarbonyl]phenylmethyl;

the compound of formula (II) wherein $R^1$ is 3-N,N-dimethylaminobenzyl and $R^2$ is 3-[(5-methyl-2-pyridinyl)aminocarbonyl]phenylmethyl;

the compound of formula (II) wherein $R^1$ is 5-indazolylmethyl and $R^2$ is 3-[(5-methyl-2-pyridinyl) aminocarbonyl]phenylmethyl;

the compound of formula (II) wherein $R^1$ is 3-amino-5-indazolylmethyl and $R^2$ is 3-[(5-methyl-2-pyridinyl) aminocarbonyl]phenylmethyl;

the compound of formula (II) wherein $R^1$ is 3-methyl-5-indazolylmethyl and $R^2$ is 3-[(5-methyl-2-pyridinyl) aminocarbonyl]phenylmethyl;

the compound of formula (II) wherein $R^1$ is 3,4-methylenedioxybenzyl and $R^2$ is 3-[(5-methyl-2-pyridinyl)aminocarbonyl]phenylmethyl;

the compound of formula (II) wherein $R^1$ is 3-pyridinylmethyl and $R^2$ is 3-[(5-methyl-2-pyridinyl) aminocarbonyl]phenylmethyl;

the compound of formula (II) wherein $R^1$ is 3-furanylmethyl and $R^2$ is 3-[(5-methyl-2-pyridinyl) aminocarbonyl]phenylmethyl;

the compound of formula (II) wherein $R^1$ is 3-thienylmethyl and $R^2$ is 3-[(5-methyl-2-pyridinyl) aminocarbonyl]phenylmethyl;

the compound of formula (II) wherein $R^1$ is cyclopropylmethyl and $R^2$ is 3-[(6-methyl-2-pyridinyl) aminocarbonyl]phenylmethyl;

the compound of formula (II) wherein $R^1$ is n-butyl and $R^2$ is 3-[(6-methyl-2-pyridinyl)aminocarbonyl] phenylmethyl;

the compound of formula (II) wherein $R^1$ is benzyl and $R^2$ is 3-[(6-methyl-2-pyridinyl)aminocarbonyl] phenylmethyl;

the compound of formula (II) wherein $R^1$ is 2-naphthylmethyl and $R^2$ is 3-[(6-methyl-2-pyridinyl) aminocarbonyl]phenylmethyl;

the compound of formula (II) wherein $R^1$ is (3-n-butylamino)benzyl and $R^2$ is 3-[(6-methyl-2-pyridinyl) aminocarbonyl]phenylmethyl;

the compound of formula (II) wherein $R^1$ is 3-aminobenzyl and $R^2$ is 3-[(6-methyl-2-pyridinyl) aminocarbonyl]phenylmethyl;

the compound of formula (II) wherein $R^1$ is 4-aminobenzyl and $R^2$ is 3-[(6-methyl-2-pyridinyl) aminocarbonyl]phenylmethyl;

the compound of formula (II) wherein $R^1$ is 4-N-methylaminobenzyl and $R^2$ is 3-[(6-methyl-2-pyridinyl)aminocarbonyl]phenylmethyl;

the compound of formula (II) wherein $R^1$ is 3-N-methylaminobenzyl and $R^2$ is 3-[(6-methyl-2-pyridinyl)aminocarbonyl]phenylmethyl;

the compound of formula (II) wherein $R^1$ is 3-N-ethylaminobenzyl and $R^2$ is 3-[(6-methyl-2-pyridinyl) aminocarbonyl]phenylmethyl;

the compound of formula (II) wherein $R^1$ is 3-N,N-dimethylaminobenzyl and $R^2$ is 3-[(6-methyl-2-pyridinyl)aminocarbonyl]phenylmethyl;

the compound of formula (II) wherein $R^1$ is 5-indazolylmethyl and $R^2$ is 3-[(6-methyl-2-pyridinyl) aminocarbonyl]phenylmethyl;

the compound of formula (II) wherein $R^1$ is 3-amino-5-indazolylmethyl and $R^2$ is 3-[(6-methyl-2-pyridinyl) aminocarbonyl]phenylmethyl;

the compound of formula (II) wherein $R^1$ is 3-methyl-5-indazolylmethyl and $R^2$ is 3-[(6-methyl-2-pyridinyl) aminocarbonyl]phenylmethyl;

the compound of formula (II) wherein $R^1$ is 3,4-methylenedioxybenzyl and $R^2$ is 3-[(6-methyl-2-pyridinyl)aminocarbonyl]phenylmethyl;

the compound of formula (II) wherein $R^1$ is 3-pyridinylmethyl and $R^2$ is 3-[(6-methyl-2-pyridinyl) aminocarbonyl]phenylmethyl;

the compound of formula (II) wherein $R^1$ is 3-furanylmethyl and $R^2$ is 3-[(6-methyl-2-pyridinyl) aminocarbonyl]phenylmethyl;

the compound of formula (II) wherein $R^1$ is 3-thienylmethyl and $R^2$ is 3-[(6-methyl-2-pyridinyl) aminocarbonyl]phenylmethyl.

7. A method for the treatment of HIV infection which comprises administering to a host in need of such treatment a therapeutically effective amount of a compound of claim 1.

8. A method for the treatment of HIV infection which comprises administering to a host in need of such treatment a therapeutically effective amount of a compound of claim 2.

9. A method for the treatment of HIV infection which comprises administering to a host in need of such treatment a therapeutically effective amount of a compound of claim 3.

10. A method for the treatment of HIV infection which comprises administering to a host in need of such treatment a therapeutically effective amount of a compound of claim 4.

11. A method for the treatment of HIV infection which comprises administering to a host in need of such treatment a therapeutically effective amount of a compound of claim 5.

12. A method for the treatment of HIV infection which comprises administering to a host in need of such treatment a therapeutically effective amount of a compound of claim 6.

13. A pharmaceutical composition comprising a pharmaceutically acceptable carrier and a therapeutically effective amount of a compound of claim 1.

14. A pharmaceutical composition comprising a pharmaceutically acceptable carrier and a therapeutically effective amount of a compound of claim 2.

15. A pharmaceutical composition comprising a pharmaceutically acceptable carrier and a therapeutically effective amount of a compound of claim 3.

16. A pharmaceutical composition comprising a pharmaceutically acceptable carrier and a therapeutically effective amount of a compound of claim 4.

17. A pharmaceutical composition comprising a pharmaceutically acceptable carrier and a therapeutically effective amount of a compound of claim 5.

18. A pharmaceutical composition comprising a pharmaceutically acceptable carrier and a therapeutically effective amount of a compound of claim 6.

* * * * *